US007053267B2

(12) United States Patent
Knauf et al.

(10) Patent No.: US 7,053,267 B2
(45) Date of Patent: May 30, 2006

(54) PLANT SEED OILS

(75) Inventors: Vic C. Knauf, Winters, CA (US); Gregory Thompson, Davis, CA (US)

(73) Assignee: Calgene LLC, Davis, CA (US)

( * ) Notice: Subject to any disclaimer, the term of this patent is extended or adjusted under 35 U.S.C. 154(b) by 338 days.

(21) Appl. No.: 10/100,121

(22) Filed: Mar. 18, 2002

(65) Prior Publication Data

US 2003/0097686 A1 May 22, 2003

Related U.S. Application Data

(60) Division of application No. 08/926,522, filed on Sep. 9, 1997, now Pat. No. 6,426,447, which is a continuation of application No. 08/458,173, filed on Jun. 2, 1995, now abandoned, which is a continuation-in-part of application No. 07/949,102, filed on Sep. 21, 1992, now abandoned, which is a continuation-in-part of application No. 07/762,762, filed on Sep. 16, 1991, now abandoned, which is a continuation-in-part of application No. 07/615,784, filed on Nov. 14, 1990, now abandoned, and a continuation-in-part of application No. PCT/US91/01746, filed on Mar. 14, 1991, and a continuation-in-part of application No. 07/494,106, filed on Mar. 16, 1990, now abandoned.

(51) Int. Cl.
*A01H 5/00* (2006.01)
*C12N 15/82* (2006.01)

(52) U.S. Cl. ...................................... 800/281; 800/298

(58) Field of Classification Search ................ 800/281, 800/298, 306; 435/419

See application file for complete search history.

(56) References Cited

U.S. PATENT DOCUMENTS 4,863,753 A 9/1989 Hunter et al.
5,110,728 A 5/1992 Kridl et al.
5,147,792 A 9/1992 Perchorowicz et al.
5,443,974 A * 8/1995 Hitz et al. .................. 800/264

FOREIGN PATENT DOCUMENTS

WO WO 92/20236 * 11/1992

OTHER PUBLICATIONS

Broun et al, Science 282: 1315-1317, Nov. 13, 1998.*
Van de Loo et al, PNAS, USA 92: 6743-6747, Jul. 1995.*
Doerks et al, TIG 14(6): 248-250, Jun. 1998.*
Smith et al, Nature Biotechnology 15: 1222-1223, Nov. 15, 1997.*
Brenner, S.E., TIG 15(4): 132-133, Apr. 1999.*
Bork et al, TIG 12(10): 425-427, Oct. 1996.*
DeLuca V,, AgBiotech News and Information 5(6): 225N-229N, 1993.*
Slabas et al, Plant Molecular Biology 19: 169-191, 1992.*
Ohlrogge et al, Biochimica et Biophysica Acta, 1082: 1-26, 1991.*
van de Loo et al, Chapter 3—Unusual Fatty Acids, in Lipids Metabolism in Plants, T. S. Moore, Jr., Ed., CRC Press, Bocan Raton, pp. 91-126, 1993.*
Ohlrogge, J. B., Plant Physiology 104: 821-826, 1994.*
Murphy et al, Industrial Crops and Products 3: 17-27, 1994.*
Pathak et al, Curent Science 67 (6): 470-472, 1994.*
Topfer et al, Science 268: 681-686, May 5, 1995.*
Bafor et al, JAOCS 67 (4): 217-225, Apr. 1990.*
Post-Beittenmiller, et al, Regulation of Plant Lipid Biosynthesis in Control of Plant Gene Expression, Verma, ed., CRC Press, 1993.*
Stuitje et al, Biochemistry and Molecular Biology of Membrane and Storage Lipids of Plants, Murata et al, eds, The American Society of Plant Physiologists, pp. 121-131, 1993.*
Adelman et al., "*In vitro* Deletional Mutagenesis for Bacterial Production of the 20,000-Dalton Form of Human Pituitary Growth Hormone," DNA, 1983, vol. 2, pp. 183-193.
Bach et al., "Medium-chain tryglycerides: an update," Am. J. Clin. Nat., 1982, vol. 36, pp. 950-962.
Beltz et al., "Isolation of Multigene Families and Determination of Homologies by Filter Hybridization Methods," Methods in Enzymology, 1983, Edited by Wu, Grossman and Moldane, vol. 100, pp. 266-285, Academic Press, New York.
Bhatty et al., "The proteins of rapeseed (*Brassica napus* L.) soluble in salt solutions," Can. J. Biochem., 1968, vol. 46, pp. 1191-1197.
Bolivar et al., "Construction and Characterization of New Cloning Vehicles II. A Multipurpose Cloning System," Gene, 1977, vol. 2, pp. 95-113.
Browse et al., "Fatty Acid Composition of Leaf Lipids Determined After Combined Digestion and Fatty Acid Methyl Ester Formation from Fresh Tissue," Anal. Biochem., 1986, vol. 152, pp. 141-145.

(Continued)

*Primary Examiner*—Elizabeth F. McElwain
(74) *Attorney, Agent, or Firm*—Gary M. Bond; Chunping Li; Arnold & Porter LLP

(57) ABSTRACT

By this invention, modification of the fatty acid composition of a plant seed may be achieved as a result of the activity of a DNA sequence foreign to the plant species to be modified. In particular, it has been found that a plant oil having a modified fatty acid composition can be obtained upon the expression of genes derived from plants of different species than the host plant, upon the expression of genes derived from bacteria, and from the transcription of anti-sense sequences which are complementary to endogenous genes of the plant host cell. In a preferred embodiment, transcription of the fatty acid modifying foreign DNA sequence is restricted to the developing seed tissues.

28 Claims, 99 Drawing Sheets

OTHER PUBLICATIONS

Cronan et al., "Derived Amino Acid Sequence and Identification of Active Site Residues of *Escherichia coli* β-Hydroxydecanoyl Thioester Dehydrase," J. Biol. Chem., 1988, vol. 263, pp. 4641-4646.
Ditta et al., "Broad host range DNA cloning system for Gram-negative bacteria: Construction of a gene bank of *Rhizobium meliloti*," PNAS USA, 1980, vol. 77, pp. 7347-7351.
Doolittle, R.F., "Of URFs and ORFs: A primer on how to analyze derived amino acid sequences," University Science Books, Mill Valley, CA, 1986.
Fixter et al., "Structure, Distribution and Function of Wax Esters in *Acinetobacter calcoaceticus*," J. Gen. Microbiol., 1986, vol. 132, pp. 3147-3157.
Frohman et al., "Rapid production of full-length cDNAs from rare transcripts: Amplification using a single gene-specific oligonucleotide primer," Proc. Nat. Acad. Sci., 1988, vol. 85, pp. 8998-9002.
Gould et al., "Use of the DNA polymerase chain reaction for homology probing: Isolation of partial cDNA or genomic clones encoding the iron-sulfur protein of succinate dehydrogenase from several species," PNAS USA, 1989, vol. 86, pp. 1934-1938.
Hirsch et al., "A Physical Map of pPH1Jl and pJB4Jl," Plasmid, 1984, vol. 12, pp. 139-141.
Holsters et al., "Transfection and Transformation of *Agrobacterium tumefaciens*," Mol. Gen. Genet., 1978, vol. 163, pp. 181-187.
Hood et al., "The hypervirulence of *Agrobacterium tumefaciens* A281 is Encoded in a Region of pTiBo542 Outside of T-DNA," J. Bacteriol., 1986, vol. 168(3), pp. 1291-1301.
Jaworski, et al., "A Cerulenin Insensitive Short Chain 3-Ketoacyl-Acyl Carrier Protein Synthase in *Spinacia oleracea* Leaves," Plant Physiol., 1989, vol. 90, pp. 41-44.
Khan et al., "Solubilization of Fatty Acid Synthase, Acyl-CoA Reductase, and Fatty Acyl-CoA Alcohol Transacylase from the Microsomes of *Euglena gracilis*," Arch. Biochem. Biophys., 1975, vol. 170, pp. 400-408.
Kolattukudy, P.E., "Cutin, Suberin, and Waxes", The Biochemistry of Plants, 1980, vol. 4, pp. 571-645, Edited by P. K. Stumpf, Academic Press, Inc.
Kolattukudy et al., "Acyl-CoA reductase and acyl-CoA: fatty alcohol acyl transferase in the microsomal preparation from the bovine meibomian gland," J. Lipid Res., 1986, vol. 27, pp. 404-411.
Lloyd, G.M., "Synthesis and translocation of lipids in the cell envelope membranes of *micrococcus cryophilus*: a comparison of polar and neutral lipids," Microbios., 1987, vol. 52, pp. 29-37.
Marsh et al., "The pIC plasmid and phage vectors with versatile cloning sites for recombinant selection by insertional inactivation," Gene, 1984, vol. 32, pp. 481-485.
McBride et al., "Improved binary vectors for *Agrobacterium*-mediated plant transformation," Plant Mol. Bio., 1990, vol. 14, pp. 269-276.
Messing, J. "New M13 Vectors for Cloning," Meth. in Enzymol., 1983, vol. 101, pp. 20-79, Edited by Wu, Grossman and Moldave, Academic Press, Inc.
Miyamoto et al., "Organization of the *lux* Structural Genes of *Vibrio harveyi*," J. Biol. Chem., 1988, vol. 263(26), pp. 13393-13399.
Oberfelder, R. "Immunoblotting: Comparison of Detection Methods," Focus, 1989, vol. 11(1), pp. 1-5, BRL/ Life Technologies, Inc.
Ohlrogge et al., "Studies on Biosynthesis of Waxes by Developing Jojoba Seed Tissue," Lipids, 1978, vol. 13(3), pp. 203-210.
Radke et al., "Transformation of *Brassica napus* L. using *Agrobacterium tumefaciens*: developmentally regulated expression of a reintroduced napin gene," Theor. Appl. Genet., 1988, vol. 75, pp. 685-694.
Rose et al., "The nucleotide sequence of a cDNA clone encoding acyl carrier protein (ACP) from *Brassica campestris* seeds," Nuc. Acids Res., 1987, vol. 15(17), p. 7197.
Thompson et al., "Primary structures of the precursor and mature forms of stearoyl-acyl carrier protein desaturase from safflower embryos and requirement of ferredoxin for enzyme activity," Proc. Natl. Acad. Sci. USA, 1991, vol. 88, pp. 2578-2582.
Tsay et al., "Isolation and Characterization of the β-Ketoacyl-acyl Carrier Protein Synthase III Gene (*fabH*) from *Escherichia coli* K-12," J. Biol. Chem., 1992, vol. 267(10), pp. 6807-6814.
Vieira et al., "The pUC plasmids, an M13mp7-derived system for insertion mutagenesis and sequencing with synthetic universal primers," Gene, 1982, vol. 19, pp. 259-268.

* cited by examiner

```
                                              HindIII
                                               |
  1 GCTCACTTGTGTGGTGGAGGAGAAAAACAGAACTCACAAAAAGCTTTGCGACTGCCAAGAACAACAACA   69
                                               42

 70 ACAACAAGATCAAGAAGAAGAAGAAGAAGATCAAAAATGGCTCTTCGAATCACTCCAGTGACCTTGCAA  138
                                          METAlaLeuArgIleThrProValThrLeuGln

         EcoRV                                     BglII           NcoI
           |                                         |               |
139 TCGGAGAGATATCGTTCGTTTTCGTTTCCTAAGAAGGCTAATCTCAGATCTCCCAAATTCGCCATGGCC  207
    SerGluArgTyrArgSerPheSerPheProLysLysAlaAsnLeuArgSerProLysPheAlaMETAla
           149                                       185             201

                                  HindII
                                    |
208 TCCACCCTCGGATCATCCACACCGAAGGTTGACAATGCCAAGAAGCCTTTTCAACCTCCACGAGAGGTT  276
    SerThrLeuGlySerSerThrProLysValAspAsnAlaLysLysProPheGlnProProArgGluVal
                                    238

277 CATGTTCAGGTGACGCACTCCATGCCACCACAGAAGATAGAGATTTTCAAATCCATCGAGGGTTGGGCT  345
    HisValGlnValThrHisSerMETProProGlnLysIleGluIlePheLysSerIleGluGlyTrpAla

346 GAGCAGAACATATTGGTTCACCTAAAGCCAGTGGAGAAATGTTGGCAAGCACAGGATTTCTTGCCGGAC  414
    GluGlnAsnIleLeuValHisLeuLysProValGluLysCysTrpGlnAlaGlnAspPheLeuProAsp
```

FIGURE 1A

```
415 CCTGCATCTGAAGGATTTGATGAACAAGTCAAGGAACTAAGGGCAAGAGCAAAGGAGATTCCTGATGAT 483
    ProAlaSerGluGlyPheAspGluGlnValLysGluLeuArgAlaArgAlaLysGluIleProAspAsp

484 TACTTTGTTGTTTTGGTTGGAGATATGATTACAGAGGAAGCCCTACCTACTTACCAAACAATGCTTAAT 552
    TyrPheValValLeuValGlyAspMETIleThrGluGluAlaLeuProThrTyrGlnThrMETLeuAsn

553 ACCCTAGATGGTGTACGTGATGAGACTGGGGCTAGCCTTACGCCTTGGGCTGTCTGGACTAGGGCTTGG 621
    ThrLeuAspGlyValArgAspGluThrGlyAlaSerLeuThrProTrpAlaValTrpThrArgAlaTrp

        PvuII                                                          AccI
        |                                                              |
622 ACAGCTGAAGAGAACAGGCATGGCGATCTTCTCCACACCTATCTCTACCTTTCTGGGCGGGTAGACATG 690
    ThrAlaGluGluAsnArgHisGlyAspLeuLeuHisThrTyrLeuTyrLeuSerGlyArgValAspMET
        626                                                            684

                                                    BamHI
                                                    |
691 AGGCAGATACAGAAGACAATTCAGTATCTCATTGGGTCAGGAATGGATCCTCGTACCGAAAACAGCCCC 759
    ArgGlnIleGlnLysThrIleGlnTyrLeuIleGlySerGlyMETAspProArgThrGluAsnSerPro
                                                    736

760 TACCTTGGGTTCATCTACACATCGTTTCAAGAGCGTGCCACATTTGTTTCTCACGGAAACACCGCCAGG 828
    TyrLeuGlyPheIleTyrThrSerPheGlnGluArgAlaThrPheValSerHisGlyAsnThrAlaArg
```

FIGURE 1B

```
     SphI
     |
829  CATGCAAAGGATCATGGGGACGTGAAACTGGCGCAAATTTGTGGTACAATCGCGTCTGACGAAAAGCGT  897
     HisAlaLysAspHisGlyAspValLysLeuAlaGlnIleCysGlyThrIleAlaSerAspGluLysArg
     833

                                                         ClaI
                                                         |
898  CACGAGACCGCTTATACAAAGATAGTCGAAAAGCTATTCGAGATCGATCCTGATGGCACCGTTCTTGCT  966
     HisGluThrAlaTyrThrLysIleValGluLysLeuPheGluIleAspProAspGlyThrValLeuAla
                                                         942

                        BglII
                        |
967  TTTGCCGACATGATGAGGAAAAAGATCTCGATGCCCGCACACTTGATGTACGATGGGCGTGATGACAAC 1035
     PheAlaAspMETMETArgLysLysIleSerMETProAlaHisLeuMETTyrAspGlyArgAspAspAsn
                        990

                                                      AccI
                                                      |
1036 CTCTTCGAACATTTCTCGGCGGTTGCCCAAAGACTCGGCGTCTACACCGCCAAAGACTACGCCGACATA 1104
     LeuPheGluHisPheSerAlaValAlaGlnArgLeuGlyValTyrThrAlaLysAspTyrAlaAspIle
                                                      1077

1105 CTGGAATTTCTGGTCGGGCGGTGGAAAGTGGCGGATTTGACCGGCCTATCTGGTGAAGGGCGTAAAGCG 1173
     LeuGluPheLeuValGlyArgTrpLysValAlaAspLeuThrGlyLeuSerGlyGluGlyArgLysAla
```

FIGURE 1C

```
                                                                    SacI
                                                                    |
1174 CAAGATTATGTTTGCGGGTTGCCACCAAGAATCAGAAGGCTGGAGGAGAGAGCTCAAGGGCGAGCAAAG 1242
     GlnAspTyrValCysGlyLeuProProArgIleArgArgLeuGluGluArgAlaGlnGlyArgAlaLys
                                                                    1228

                       PvuII
                       |
1243 GAAGGACCTGTTGTTCCATTCAGCTGGATTTTCGATAGACAGGTGAAGCTGTGAAGAAAAAAAAAACGA 1311
     GluGlyProValValProPheSerTrpIlePheAspArgGlnValLysLeu
                       1266

1312 GCAGTGAGTTCGGTTTCTGTTGGCTTATTGGGTAGACGTTAAAACCTATTTTAGATGTCTGTTTCGTGT 1380

1381 AATGTGGTTTTTTTTCTTCTAATCTTGAATCTGGTATTGTGTCGTTGAGTTCGCGTGTGTGTAAACTTG 1449

1450 TGTGGCTGTGGACATATTATAGAACTCGTTATGCCAATTTTGATGACGGTGGTTATCGTCTCCCCTGGT 1518

1519 GTTTTTTTATTGTTT 1533
```

FIGURE 1D

```
AAAAGAAAAA GGTAAGAAAA AAAACA ATG GCT CTC AAG CTC AAT CCT TTC CTT TCT     56
                             MET Ala Leu Lys Leu Asn Pro Phe Leu Ser

CAA ACC CAA AAG TTA CCT TCT TTC GCT CTT CCA CCA ATG GCC AGT ACC AGA TCT 110
Gln Thr Gln Lys Leu Pro Ser Phe Ala Leu Pro Pro MET Ala Ser Thr Arg Ser

CCT AAG TTC TAC ATG GCC TCT ACC CTC AAG TCT GGT TCT AAG GAA GTT GAG AAT 164
Pro Lys Phe Tyr MET Ala Ser Thr Leu Lys Ser Gly Ser Lys Glu Val Glu Asn

CTC AAG AAG CCT TTC ATG CCT CCT CGG GAG GTA CAT GTT CAG GTT ACC CAT TCT 218
Leu Lys Lys Pro Phe MET Pro Pro Arg Glu Val His Val Gln Val Thr His Ser

ATG CCA CCC CAA AAG ATT GAG ATC TTT AAA TCC CTA GAC AAT TGG GCT GAG GAG 272
MET Pro Pro Gln Lys Ile Glu Ile Phe Lys Ser Leu Asp Asn Trp Ala Glu Glu

AAC ATT CTG GTT CAT CTG AAG CCA GTT GAG AAA TGT TGG CAA CCG CAG GAT TTT 326
Asn Ile Leu Val His Leu Lys Pro Val Glu Lys Cys Trp Gln Pro Gln Asp Phe

TTG CCA GAT CCC GCC TCT GAT GGA TTT GAT GAG CAA GTC AGG GAA CTC AGG GAG 380
Leu Pro Asp Pro Ala Ser Asp Gly Phe Asp Glu Gln Val Arg Glu Leu Arg Glu
```

FIGURE 2A

```
AGA GCA AAG GAG ATT CCT GAT GAT TAT TTT GTT CTT TTG GTT GGA GAC ATG ATA    434
Arg Ala Lys Glu Ile Pro Asp Asp Tyr Phe Val Val Leu Val Gly Asp MET Ile

ACG GAA GAA GCC CTT CCC ACT TAT CAA ACA ATG CTG AAT ACC TTG GAT GGA GTT    488
Thr Glu Glu Ala Leu Pro Thr Tyr Gln Thr MET Leu Asn Thr Leu Asp Gly Val

CGG GAT GAA ACA GGT GCA AGT CCT ACT TCT TGG GCA ATT TGG ACA AGG GCA TGG    542
Arg Asp Glu Thr Gly Ala Ser Pro Thr Ser Trp Ala Ile Trp Thr Arg Ala Trp

ACT GCG GAA GAG AAT AGA CAT GGT GAC CTC CTC AAT AAG TAT CTC TAC CTA TCT    596
Thr Ala Glu Glu Asn Arg His Gly Asp Leu Leu Asn Lys Tyr Leu Tyr Leu Ser

GGA CGA GTG GAC ATG AGG CAA ATT GAG AAG ACA ATT CAA TAT TTG ATT GGT TCA    650
Gly Arg Val Asp MET Arg Gln Ile Glu Lys Thr Ile Gln Tyr Leu Ile Gly Ser

GGA ATG GAT CCA CGG ACA GAA AAC AGT CCA TAC CTT GGG TTC ATC TAT ACA TCA    704
Gly MET Asp Pro Arg Thr Glu Asn Ser Pro Tyr Leu Gly Phe Ile Tyr Thr Ser

TTC CAG GAA AGG GCA ACC TTC ATT TCT CAT GGG AAC ACT GCC CGA CAA GCC AAA    758
Phe Gln Glu Arg Ala Thr Phe Ile Ser His Gly Asn Thr Ala Arg Gln Ala Lys

GAG CAT GGA GAC ATA AAG TTG GCT CAA ATA TGT GGT ACA ATT GCT GCA GAT GAG    812
Glu His Gly Asp Ile Lys Leu Ala Gln Ile Cys Gly Thr Ile Ala Ala Asp Glu
```

FIGURE 2B

```
AAG CGC CAT GAG ACA GCC TAC ACA AAG ATA GTG GAA AAA CTC TTT GAG ATT GAT     866
Lys Arg His Glu Thr Ala Tyr Thr Lys Ile Val Glu Lys Leu Phe Glu Ile Asp

CCT GAT GGA ACT GTT TTG GCT TTT GCT GAT ATG ATG AGA AAG AAA ATT TCT ATG     920
Pro Asp Gly Thr Val Leu Ala Phe Ala Asp MET MET Arg Lys Lys Ile Ser MET

CCT GCA CAC TTG ATG TAT GAT GGC CGA GAT GAT AAT CTT TTT GAC CAC TTT TCA     974
Pro Ala His Leu MET Tyr Asp Gly Arg Asp Asp Asn Leu Phe Asp His Phe Ser

GCT GTT GCG CAG CGT CTT GGA GTC TAC ACA GCA AAG GAT TAT GCA GAT ATA TTG    1028
Ala Val Ala Gln Arg Leu Gly Val Tyr Thr Ala Lys Asp Tyr Ala Asp Ile Leu

GAG TTC TTG GTG GGC AGA TGG AAG GTG GAT AAA CTA ACG GGC CTT TCA GCT GAG    1082
Glu Phe Leu Val Gly Arg Trp Lys Val Asp Lys Leu Thr Gly Leu Ser Ala Glu

GGA CAA AAG GCT CAG GAC TAT GTT TGT CGG TTA CCT CCA AGA ATT AGA AGG CTG    1136
Gly Gln Lys Ala Gln Asp Tyr Val Cys Arg Leu Pro Pro Arg Ile Arg Arg Leu

GAA GAG AGA GCT CAA GGA AGG GCA AAG GAA GCA CCC ACC ATG CCT TTC AGC TGG    1190
Glu Glu Arg Ala Gln Gly Arg Ala Lys Glu Ala Pro Thr MET Pro Phe Ser Trp
```

FIGURE 2C

```
ATT TTC GAT AGG CAA GTG AAG CTG TAGGTGGCTA AAGTGCAGGA CGAAACCGAA ATGGTTAGTT  1254
Ile Phe Asp Arg Gln Val Lys Leu

TCACTCTTTT TCATGCCCAT CCCTGCAGAA TCAGAAGTAG AGGTAGAATT TTGTAGTTGC TTTTTTATTA 1324

CAAGTCCAGT TTAGTTTAAG GTCTGTGGAA GGGAGTTAGT TGAGGAGTGA ATTTAGTAAG TTGTAGATAC 1394

AGTTGTTTCT TGTGTTGTCA TGAGTATGCT GATAGAGAGC AGCTGTAGTT TTGTTGTTGT GTTCTTTTAT 1464

ATGGTCTCTT GTATGAGTTT CTTTTCTTTC CTTTTCTTCT TTCCTTTCCT CTCTCTCTCT CTCTCTCTCT 1534

CTCTTTTTCT CTTATCCCAA GTGTCTCAAG TATAATAAGC AAACGATCCA TGTGGCAATT TTGATGATGG 1604

TGATCAGTCT CACAACTTGA TCTTTTGTCT TCTATTGGAA ACACAGCCTG CTTGTTTGAA AAAA       1668
```

FIGURE 2D pCGN3235

```
TGAGAGATAG TGTGAGAGCA TTAGCCTTAG AGAGAGAGAG AGAGAGCTTG TGTCTGAAAG AATCCACAA

ATG GCA TTG AAG CTT AAC CCT TTG GCA TCT CAG CCT TAC AAC TTC CCT TCC TCG
MET Ala Leu Lys Leu Asn Pro Leu Ala Ser Gln Pro Tyr Asn Phe Pro Ser Ser

GCT CGT CCG CCA ATC TCT ACT TTC AGA TCT CCC AAG TTC CTC TGC CTC GCT TCT
Ala Arg Pro Pro Ile Ser Thr Phe Arg Ser Pro Lys Phe Leu Cys Leu Ala Ser

TCT TCT CCC GCT CTC AGC TCC AAG GAG GTT GAG AGT TTG AAG AAG CCA TTC ACA
Ser Ser Pro Ala Leu Ser Ser Lys Glu Val Glu Ser Leu Lys Lys Pro Phe Thr

CCA CCT AAG GAA GTG CAC GTT CAA GTC CTG CAT TCC ATG CCA CCC CAG AAG ATC
Pro Pro Lys Glu Val His Val Gln Val Leu His Ser MET Pro Pro Gln Lys Ile

GAG ATC TTC AAA TCC ATG GAA GAC TGG GCC GAG CAG AAC CTT CTA ACT CAG CTC
Glu Ile Phe Lys Ser MET Glu Asp Trp Ala Glu Gln Asn Leu Leu Thr Gln Leu

AAA GAC GTG GAG AAG TCG TCG CAG CCC CAG GAC TTC TTA CCC GAC CCT GCA TCC
Lys Asp Val Glu Lys Ser Trp Gln Pro Gln Asp Phe Leu Pro Asp Pro Ala Ser

GAT GGG TTC GAA GAT CAG GTT AGA GAG CTA AGA GAG AGG GCA AGA GAG CTC CCT
Asp Gly Phe Glu Asp Gln Val Arg Glu Leu Arg Glu Arg Ala Arg Glu Leu Pro

GAT GAT TAC TTC GTT GTT CTG GTG GGA GAC ATG ATC ACG GAA GAG GCG CTT CCG
Asp Asp Tyr Phe Val Val Leu Val Gly Asp MET Ile Thr Glu Glu Ala Leu Pro
```

FIGURE 3A

```
ACC TAT CAA ACC ATG TTG AAC ACT TTG GAT GGA GTG AGG GAT GAA ACT GGC GCT
Thr Tyr Gln Thr MET Leu Asn Thr Leu Asp Gly Val Arg Asp Glu Thr Gly Ala

AGC CCC ACT TCA TGG GCT ATT TGG ACA AGA GCT TGG ACT GCA GAA GAG AAC CGA
Ser Pro Thr Ser Trp Ala Ile Trp Thr Arg Ala Trp Thr Ala Glu Glu Asn Arg

CAC GGT GAT CTT CTC AAT AAG TAT CTT TAC TTG TCT GGA CGT GTT GAC ATG AGG
His Gly Asp Leu Leu Asn Lys Tyr Leu Tyr Leu Ser Gly Arg Val Asp MET Arg

CAG ATT GAA AAG ACC ATT CAG TAC TTG ATT GGT TCT GGA ATG GAT CCT AGA ACA
Gln Ile Glu Lys Thr Ile Gln Tyr Leu Ile Gly Ser Gly MET Asp Pro Arg Thr

GAG AAC AAT CCT TAC CTC GGC TTC ATC TAC ACT TCA TTC CAA GAA AGA GCC ACC
Glu Asn Asn Pro Tyr Leu Gly Phe Ile Tyr Thr Ser Phe Gln Glu Arg Ala Thr

TTC ATC TCT CAC GGA AAC ACA GCT CGC CAA GCC AAA GAG CAC GGA GAC CTC AAG
Phe Ile Ser His Gly Asn Thr Ala Arg Gln Ala Lys Glu His Gly Asp Leu Lys

CTA GCC CAA ATC TGC GGC ACA ATA GCT GCA GAC GAG AAG CGT CAT GAG ACA GCT
Leu Ala Gln Ile Cys Gly Thr Ile Ala Ala Asp Glu Lys Arg His Glu Thr Ala

TAC ACC AAG ATA GTT GAG AAG CTC TTT GAG ATT GAT CCT GAT GGT ACT GTG ATG
Tyr Thr Lys Ile Val Glu Lys Leu Phe Glu Ile Asp Pro Asp Gly Thr Val MET

GCG TTT GCA GAC ATG ATG AGG AAG AAA ATC TCG ATG CCT GCT CAC TTG ATG TAC
Ala Phe Ala Asp MET MET Arg Lys Lys Ile Ser MET Pro Ala His Leu MET Tyr
```

FIGURE 3B

GAT GGG CGG GAT GAA AGC CTC TTT GAC AAC TTC TCT TCT GTT GCT CAG AGG CTC
Asp Gly Arg Asp Glu Ser Leu Phe Asp Asn Phe Ser Ser Val Ala Gln Arg Leu

GGT GTT TAC ACT GCC AAA GAC TAT GCG GAC ATT CTT GAG TTT TTG GTT GGG AGG
Gly Val Tyr Thr Ala Lys Asp Tyr Ala Asp Ile Leu Glu Phe Leu Val Gly Arg

TGG AAG ATT GAG AGC TTG ACC GGG CTT TCA GGT GAA GGA AAC AAA GCG CAA GAG
Trp Lys Ile Glu Ser Leu Thr Gly Leu Ser Gly Glu Gly Asn Lys Ala Gln Glu

TAC TTG TGT GGG TTG ACT CCA AGA ATC AGG AGG TTG GAT GAG AGA GCT CAA GCA
Tyr Leu Cys Gly Leu Thr Pro Arg Ile Arg Arg Leu Asp Glu Arg Ala Gln Ala

AGA GCC AAG AAA GGA CCC AAG GTT CCT TTC AGC TGG ATA CAT GAC AGA GAA GTG
Arg Ala Lys Lys Gly Pro Lys Val Pro Phe Ser Trp Ile His Asp Arg Glu Val

CAG CTC TAA AAAGGAA CAAAGCTATG AAACCTTTTC ACTCTCCGTC GTCCCTCATT TGATCTATCT
Gln Leu

GCTCTTGAAA TTGGTGTAGA TTACTATGGT TTGTGATATT GTTCGTGGGT CTAGTTACAA AGTTGAGAAG

CAGTGATTTA GTAGCTTTGT TGTTTCCAGT CTTTAAATGT TTTTGTGTTT GCTCCTTTTA GTAAACTTGT

TGTAGTTAAA TCAGTTGAAC TGTTTGGTCT GT

FIGURE 3C

```
GAT GCC AAA ANG CCT CAC ATG CCT CCT AGA GAA GCT CAT GTG CAA AAG    48
Asp Ala Lys Xaa Pro His MET Pro Pro Arg Glu Ala His Val Gln Lys
 1               5                  10                  15

ACC CAT TCA ATK CCG CCT CAA AAG ATT GAG ATT TTC AAA TCC TTG GAG    96
Thr His Ser Xaa Pro Pro Gln Lys Ile Glu Ile Phe Lys Ser Leu Glu
            20                  25                  30

GGT TGG GCT GAG GAG AAT GTC TTG GTG CAT CTT AAA CCT GTG GAG AA    143
Gly Trp Ala Glu Glu Asn Val Leu Val His Leu Lys Pro Val Glu
        35                  40                  45
```

FIGURE 4

```
AGAGAGAGAG AGAGAGAGAG AGCTAAATTA AAAAAAAAAC CCAGAAGTGG GAAATCTTCC   60

CCATGAAATA ACGGATCCTC TTGCTACTGC TACTACTACT ACTACAAACT GTAGCCATTT  120

ATATAATTCT ATATAATTTT CAAC ATG GCC ACC ACC TCT TTA GCT TCC GCT TTC 174
                           Met Ala Thr Thr Ser Leu Ala Ser Ala Phe
                            1               5                  10

TGC TCG ATG AAA GCT GTA ATG TTG GCT CGT GAT GGC CGG GGC ATG AAA      222
Cys Ser Met Lys Ala Val Met Leu Ala Arg Asp Gly Arg Gly Met Lys
                15                  20                  25

CCC AGG AGC AGT GAT TTG CAG CTG AGG GCG GGA AAT GCG CCA ACC TCT      270
Pro Arg Ser Ser Asp Leu Gln Leu Arg Ala Gly Asn Ala Pro Thr Ser
            30                  35                  40

TTG AAG ATG ATC AAT GGG ACC AAG TTC AGT TAC ACG GAG AGC TTG AAA      318
Leu Lys Met Ile Asn Gly Thr Lys Phe Ser Tyr Thr Glu Ser Leu Lys
        45                  50                  55

AGG TTG CCT GAC TGG AGC ATG CTC TTT GCA GTG ATC ACA ACC ATC TTT      366
Arg Leu Pro Asp Trp Ser Met Leu Phe Ala Val Ile Thr Thr Ile Phe
    60                  65                  70
```

FIGURE 5A

```
TCG GCT GCT GAG AAG CAG TGG ACC AAT CTA GAG TGG AAG CCG AAG CCG      414
Ser Ala Ala Glu Lys Gln Trp Thr Asn Leu Glu Trp Lys Pro Lys Pro
75                  80                  85                  90

AAG CTA CCC CAG TTG CTT GAT GAC CAT TTT GGA CTG CAT GGG TTA GTT      462
Lys Leu Pro Gln Leu Leu Asp Asp His Phe Gly Leu His Gly Leu Val
                95                  100                 105

TTC AGG CGC ACC TTT GCC ATC AGA TCT TAT GAG GTG GGA CCT GAC CGC      510
Phe Arg Arg Thr Phe Ala Ile Arg Ser Tyr Glu Val Gly Pro Asp Arg
            110                 115                 120

TCC ACA TCT ATA CTG GCT GTT ATG AAT CAC ATG CAG GAG GCT ACA CTT      558
Ser Thr Ser Ile Leu Ala Val Met Asn His Met Gln Glu Ala Thr Leu
        125                 130                 135

AAT CAT GCG AAG AGT GTG GGA ATT CTA GGA GAT GGA TTC GGG ACG ACC      606
Asn His Ala Lys Ser Val Gly Ile Leu Gly Asp Gly Phe Gly Thr Thr
    140                 145                 150

CTA GAG ATG AGT AAG AGA GAT CTG ATG TGG GTT GTG AGA CGC ACG CAT      654
Leu Glu Met Ser Lys Arg Asp Leu Met Trp Val Val Arg Arg Thr His
155                 160                 165                 170
```

FIGURE 5B

```
GTT GCT GTG GAA CGG TAC CCT ACT TGG GGT GAT ACT GTA GAA GTA GAG      702
Val Ala Val Glu Arg Tyr Pro Thr Trp Gly Asp Thr Val Glu Val Glu
                175                 180                 185

TGC TGG ATT GGT GCA TCT GGA AAT AAT GGC ATG CGA CGT GAT TTC CTT      750
Cys Trp Ile Gly Ala Ser Gly Asn Asn Gly Met Arg Arg Asp Phe Leu
            190                 195                 200

GTC CGG GAC TGC AAA ACA GGC GAA ATT CTT ACA AGA TGT ACC AGC CTT      798
Val Arg Asp Cys Lys Thr Gly Glu Ile Leu Thr Arg Cys Thr Ser Leu
        205                 210                 215

TCG GTG CTG ATG AAT ACA AGG ACA AGG AGG TTG TCC ACA ATC CCT GAC      846
Ser Val Leu Met Asn Thr Arg Thr Arg Arg Leu Ser Thr Ile Pro Asp
    220                 225                 230

GAA GTT AGA GGG GAG ATA GGG CCT GCA TTC ATT GAT AAT GTG GCT GTC      894
Glu Val Arg Gly Glu Ile Gly Pro Ala Phe Ile Asp Asn Val Ala Val
235                 240                 245                 250

AAG GAC GAT GAA ATT AAG AAA CTA CAG AAG CTC AAT GAC AGC ACT GCA      942
Lys Asp Asp Glu Ile Lys Lys Leu Gln Lys Leu Asn Asp Ser Thr Ala
                255                 260                 265
```

FIGURE 5C

```
GAT TAC ATC CAA GGA GGT TTG ACT CCT CGA TGG AAT GAT TTG GAT GTC     990
Asp Tyr Ile Gln Gly Gly Leu Thr Pro Arg Trp Asn Asp Leu Asp Val
            270                 275                 280

AAT CAG CAT GTG AAC AAC CTC AAA TAC GTT GCC TGG GTT TTT GAG ACC    1038
Asn Gln His Val Asn Asn Leu Lys Tyr Val Ala Trp Val Phe Glu Thr
        285                 290                 295

GTC CCA GAC TCC ATC TTT GAG AGT CAT CAT ATT TCC AGC TTC ACT CTT    1086
Val Pro Asp Ser Ile Phe Glu Ser His His Ile Ser Ser Phe Thr Leu
    300                 305                 310

GAA TAC AGG AGA GAG TGC ACG AGG GAT AGC GTG CTG CGG TCC CTG ACC    1134
Glu Tyr Arg Arg Glu Cys Thr Arg Asp Ser Val Leu Arg Ser Leu Thr
315                 320                 325                     330

ACT GTC TCT GGT GGC TCG TCG GAG GCT GGG TTA GTG TGC GAT CAC TTG    1182
Thr Val Ser Gly Gly Ser Ser Glu Ala Gly Leu Val Cys Asp His Leu
                335                 340                 345

CTC CAG CTT GAA GGT GGG TCT GAG GTA TTG AGG GCA AGA ACA GAG TGG    1230
Leu Gln Leu Glu Gly Gly Ser Glu Val Leu Arg Ala Arg Thr Glu Trp
            350                 355                 360
```

FIGURE 5D

```
AGG CCT AAG CTT ACC GAT AGT TTC AGA GGG ATT AGT GTG ATA CCC GCA    1278
Arg Pro Lys Leu Thr Asp Ser Phe Arg Gly Ile Ser Val Ile Pro Ala
        365                 370                 375

GAA CCG AGG GTG TAACTAATGA AAGAAGCATC TGTTGAAGTT TCTCCCATGC        1330
Glu Pro Arg Val
    380

TGTTCGTGAG GATACTTTTT AGAAGCTGCA CTTTGCATTG CTTGTGCAGA ATCATGGTCT 1390

GTGGTTTTAG ATGTATATAA AAAATAGTCC TGTAGTCATG AAACTTAATA TCAGAAAAAT 1450

AACTCAATGG GTCAAGGTTA TCGAAGTAGT CATTTAAGCT TTGAAATATG TTTTGTATTC 1510

CTCGGCTTAA TCTGTAAGCT CTTTCTCTTG CAATAAAGTT CGCCTTTCAA T          1561
```

FIGURE 5E

```
AAAAAAGTAC AAACTGTATG GTAGCCATTT ACATATAACT ACTCTATAAT TTTCAAC ATG    60
                                                               Met
                                                                1

GTC ACC ACC TCT TTA GCT TCC GCT TTC TTC TCG ATG AAA GCT GTA ATG      108
Val Thr Thr Ser Leu Ala Ser Ala Phe Phe Ser Met Lys Ala Val Met
             5                  10                  15

TTG GCT CCT GAT GGC AGT GGC ATA AAA CCC AGG AGC AGT GGT TTG CAG      156
Leu Ala Pro Asp Gly Ser Gly Ile Lys Pro Arg Ser Ser Gly Leu Gln
         20                  25                  30

GTG AGG GCG GGA AAG GAA CAA AAC TCT TGC AAG ATG ATC AAT GGG ACC      204
Val Arg Ala Gly Lys Glu Gln Asn Ser Cys Lys Met Ile Asn Gly Thr
     35                  40                  45

AAG GTC AAA GAC ACG GAG GGC TTG AAA GGG CGC AGC ACA TTG CAT GGC      252
Lys Val Lys Asp Thr Glu Gly Leu Lys Gly Arg Ser Thr Leu His Gly
50                  55                  60                  65

TGG AGC ATG CCC CTT GAA TTG ATC ACA ACC ATC TTT TCG GCT GCT GAG      300
Trp Ser Met Pro Leu Glu Leu Ile Thr Thr Ile Phe Ser Ala Ala Glu
                 70                  75                  80
```

FIGURE 6A

```
AAG CAG TGG ACC AAT CTA GTT AGT AAG CCA CCG CAG TTG CTT GAT GAC       348
Lys Gln Trp Thr Asn Leu Val Ser Lys Pro Pro Gln Leu Leu Asp Asp
            85                  90                  95

CAT TTA GGT CTG CAT GGG CTA GTT TTC AGG CGC ACC TTT GCA ATC AGA       396
His Leu Gly Leu His Gly Leu Val Phe Arg Arg Thr Phe Ala Ile Arg
        100                 105                 110

TGC AGT GAG GTT GGA CCT GAC CGC TCC ACA TCC ATA GTG GCT GTT ATG       444
Cys Ser Glu Val Gly Pro Asp Arg Ser Thr Ser Ile Val Ala Val Met
    115                 120                 125

AAT TAC TTG CAG GAA GCT GCA TGT AAT CAT GCG GAG AGT CTG GGA CTT       492
Asn Tyr Leu Gln Glu Ala Ala Cys Asn His Ala Glu Ser Leu Gly Leu
130                 135                 140                 145

CTA GGA GAT GGA TTC GGT GAG ACA CTA GAG ATG AGT AGG AGA GAT CTG       540
Leu Gly Asp Gly Phe Gly Glu Thr Leu Glu Met Ser Arg Arg Asp Leu
                150                 155                 160

ATA TGG GTT GTG AGA CGC ACG CAT GTT GTT GTG GGA ACG TAC CCT GCT       588
Ile Trp Val Val Arg Arg Thr His Val Val Val Gly Thr Tyr Pro Ala
            165                 170                 175
```

FIGURE 6B

```
TGG GGC GAT ACT GTT GAA GTC GAG GCC TGG ATC GGT GCA GCT GGA AAC      636
Trp Gly Asp Thr Val Glu Val Glu Ala Trp Ile Gly Ala Ala Gly Asn
        180                 185                 190

ATT GGC ATG CGC CGC CAT TTT CTT GTC CGC GAC TGC AAA ACT GGC CAC      684
Ile Gly Met Arg Arg His Phe Leu Val Arg Asp Cys Lys Thr Gly His
    195                 200                 205

ATT CTT GCA AGA TGT ACC AGT GTT TCA GTG ATG ATG AAT ATG AGG ACA      732
Ile Leu Ala Arg Cys Thr Ser Val Ser Val Met Met Asn Met Arg Thr
210                 215                 220                     225

AGG AGA TTG TCC AAA ATT CCC CAA GAA GTT AGA GGG GAG ATT GAC CCT      780
Arg Arg Leu Ser Lys Ile Pro Gln Glu Val Arg Gly Glu Ile Asp Pro
                230                 235                 240

CTT TTC ATC GAA AAG TTT GCT GTC AAG GAA GGG GAA ATT AAG AAA TTA      828
Leu Phe Ile Glu Lys Phe Ala Val Lys Glu Gly Glu Ile Lys Lys Leu
            245                 250                 255

CAG AAG TTC AAT GAT AGC ACT GCA GAT TAC ATT CAA GGG GGT TGG ACT      876
Gln Lys Phe Asn Asp Ser Thr Ala Asp Tyr Ile Gln Gly Gly Trp Thr
        260                 265                 270
```

FIGURE 6C

```
CCG CGA TGG AAT GAT TTG GAT GTC AAT CAG CAC GTG AAC AAT ATC AAA      924
Pro Arg Trp Asn Asp Leu Asp Val Asn Gln His Val Asn Asn Ile Lys
    275                 280                 285

TAC GTT GGC TGG ATT TTT AAG AGC GTC CCA GAC TCT ATC TAT GAG AAT      972
Tyr Val Gly Trp Ile Phe Lys Ser Val Pro Asp Ser Ile Tyr Glu Asn
290                 295                 300                 305

CAT CAT CTT TCT AGC ATC ACT CTC GAA TAC AGG AGA GAG TGC ACA AGG     1020
His His Leu Ser Ser Ile Thr Leu Glu Tyr Arg Arg Glu Cys Thr Arg
                310                 315                 320

GGC AGA GCA CTG CAG TCC CTG ACC ACT GTT TGT GGT GGC TCG TCC GAA     1068
Gly Arg Ala Leu Gln Ser Leu Thr Thr Val Cys Gly Gly Ser Ser Glu
            325                 330                 335

GCT GGG ATC ATA TGT GAG CAC CTA CTC CAG CTT GAG GAT GGG TCT GAG     1116
Ala Gly Ile Ile Cys Glu His Leu Leu Gln Leu Glu Asp Gly Ser Glu
        340                 345                 350

GTT TTG AGG GGA AGA ACA GAT TGG AGG CCC AAG CGC ACC GAT AGT TTC     1164
Val Leu Arg Gly Arg Thr Asp Trp Arg Pro Lys Arg Thr Asp Ser Phe
    355                 360                 365
```

FIGURE 6D

```
GAA GGC ATT AGT GAG AGA TTC CCG CAG CAA GAA CCG CAT AAT TAAT        1210
Glu Gly Ile Ser Glu Arg Phe Pro Gln Gln Glu Pro His Asn
370                 375                 380

GACAGAAGCA TCAGATATAG TTTCTCCTGT GCTGTTCCTG AGAATGCATC TTACAAGTCG  1270

TGGTTTGGAT TGCTTGTGCA GAATCATGGT TTGTGCTTTC AGAAGTATAT CTAAATTAGT  1330

CCAAGTTATA TGACTCCATA TTGGAAAATA ACTCAATGAG TCGTGCTCTT GAAATGGTCT  1390

TTTAAGCTTT GAAATAAAGT TCCACTTAAT CCATGTAAAA AAAAA                  1435
```

FIGURE 6E

```
GGGTAACATG GCATAAACGT GAATAACTGC AACTCCAGTG TCACTTTCCC TTTCCTTTCC   60

ACCACCATCT CCTCCCTCGG TCCCATCGAC GGCAAACTCC ATAAAACCAC CACCACCTCT  120

TCAAATCAAC ACCTCTTCCG AACCACCACC ACCACCACCG CCGCCGGCAA CT ATG CTA  178
                                                          Met Leu
                                                           1

TCA CGA CCT CTT CCG ACC ACC GCC GCG GCG GCG ACC ACG ACG ACG AAT    226
Ser Arg Pro Leu Pro Thr Thr Ala Ala Ala Ala Thr Thr Thr Thr Asn
         5                  10                  15

AAT TGC AAT GGC GTC AAC TCC CGC GGC GCC TTA CCT CAT TCC CGA TCC    274
Asn Cys Asn Gly Val Asn Ser Arg Gly Ala Leu Pro His Ser Arg Ser
     20                  25                  30

GTT GGA TTC GCC TCG ATT CGG AAA CGA AGC ACC GGT TCC TTA TGC AAT    322
Val Gly Phe Ala Ser Ile Arg Lys Arg Ser Thr Gly Ser Leu Cys Asn
35                  40                  45                  50
```

FIGURE 7A

```
TCG CCG CCG CGG ACG GTG GCG CCG GTG ATG GCG GTG AGG ACC GGT GAG     370
Ser Pro Pro Arg Thr Val Ala Pro Val Met Ala Val Arg Thr Gly Glu
                55                  60                  65

CAA CCG ACC GGC GTT GCC GTC GGA TTG AAG GAG GCG GAG GCG GAG GTG     418
Gln Pro Thr Gly Val Ala Val Gly Leu Lys Glu Ala Glu Ala Glu Val
            70                  75                  80

GAG AAG AGC CTG GCG GAT CGG CTT CGG ATG GGG AGC TTG ACG GAA GAT     466
Glu Lys Ser Leu Ala Asp Arg Leu Arg Met Gly Ser Leu Thr Glu Asp
        85                  90                  95

GGA TTG TCG TAT AAG GAG AGG TTC ATC ATA AGG TGT TAT GAA GTC GGG     514
Gly Leu Ser Tyr Lys Glu Arg Phe Ile Ile Arg Cys Tyr Glu Val Gly
    100                 105                 110

ATT AAT AAG ACT GCA ACT GTT GAA ACC ATT GCT AAT CTA TTG CAG GAG     562
Ile Asn Lys Thr Ala Thr Val Glu Thr Ile Ala Asn Leu Leu Gln Glu
115                 120                 125                 130
```

FIGURE 7B

```
GTT GGA GGT AAT CAT GCT CAG AGT GTT GGA TTT TCA ACA GAC GGA TTT      610
Val Gly Gly Asn His Ala Gln Ser Val Gly Phe Ser Thr Asp Gly Phe
                135                 140                 145

GCC ACC ACG ACC ACT ATG CGA AAA TTG CAT CTC ATA TGG GTG ACT TCG      658
Ala Thr Thr Thr Thr Met Arg Lys Leu His Leu Ile Trp Val Thr Ser
            150                 155                 160

CGA ATG CAC ATT GAA ATT TAC AGA TAC CCC GCT TGG AGT GAT GTG GTT      706
Arg Met His Ile Glu Ile Tyr Arg Tyr Pro Ala Trp Ser Asp Val Val
        165                 170                 175

GAA ATC GAG ACT TGG TGT CAA AGT GAA GGA AGG ATT GGG ACT AGA CGT      754
Glu Ile Glu Thr Trp Cys Gln Ser Glu Gly Arg Ile Gly Thr Arg Arg
    180                 185                 190

GAT TGG ATT ATG AAA GAC CAT GCG AGT GGT GAA GTC ATT GGA AGG GCT      802
Asp Trp Ile Met Lys Asp His Ala Ser Gly Glu Val Ile Gly Arg Ala
195                 200                 205                 210
```

FIGURE 7C

```
ACA AGC AAA TGG GTG ATG ATG AAC GAG GAT ACT AGA AGA CTC CAG AAA     850
Thr Ser Lys Trp Val Met Met Asn Glu Asp Thr Arg Arg Leu Gln Lys
                215                 220                 225

GTC AAC GAT GAC GTC AGA GAC GAA TAT CTC GTT TTT TGT CCC AAG ACA     898
Val Asn Asp Asp Val Arg Asp Glu Tyr Leu Val Phe Cys Pro Lys Thr
            230                 235                 240

CCA AGA TTA GCA TTT CCT GAA AAG AAC ACT AGC AGC CTG AAG AAA ATA     946
Pro Arg Leu Ala Phe Pro Glu Lys Asn Thr Ser Ser Leu Lys Lys Ile
        245                 250                 255

GCA AAA CTA GAA GAC CCC GCC GAA TAT TCG ACG CTA GGG CTT GTG CCA     994
Ala Lys Leu Glu Asp Pro Ala Glu Tyr Ser Thr Leu Gly Leu Val Pro
    260                 265                 270

AGA AGA GCC GAT CTC GAT ATG AAC AAG CAT GTT AAC AAT GTT ACC TAC    1042
Arg Arg Ala Asp Leu Asp Met Asn Lys His Val Asn Asn Val Thr Tyr
275                 280                 285                 290
```

FIGURE 7D

```
ATT GGA TGG GTT CTT GAG AGC ATC CCA CAA GAA GTC ATC GAC ACT CAT    1090
Ile Gly Trp Val Leu Glu Ser Ile Pro Gln Glu Val Ile Asp Thr His
                295                 300                 305

GAA CTA CAA ACG ATT ACC CTA GAC TAC CGG CGG GAA TGC CAG CAT GAC    1138
Glu Leu Gln Thr Ile Thr Leu Asp Tyr Arg Arg Glu Cys Gln His Asp
            310                 315                 320

GAC ATA GTC GAT TCC CTC ACG AGT TCC GAG TCA CTA CTC GAC GAT GCC    1186
Asp Ile Val Asp Ser Leu Thr Ser Ser Glu Ser Leu Leu Asp Asp Ala
        325                 330                 335

GCC ATC TCG AAA CTC GAA GGA ACC AAC GGA TCT TCT GTT CCC AAA AAA    1234
Ala Ile Ser Lys Leu Glu Gly Thr Asn Gly Ser Ser Val Pro Lys Lys
    340                 345                 350

GAC GAA ACG GAT TTG AGC CGG TTT TTG CAT TTA CTA CGA TCA TCG GGC    1282
Asp Glu Thr Asp Leu Ser Arg Phe Leu His Leu Leu Arg Ser Ser Gly
355                 360                 365                     370
```

FIGURE 7E

```
GAT GGT CTC GAA CTA AAT AGG GGT CGC ACC GAG TGG AGA AAG AAA CCC    1330
Asp Gly Leu Glu Leu Asn Arg Gly Arg Thr Glu Trp Arg Lys Lys Pro
                375                 380                 385

GCG AAA AAA TGAGCAACAC CCTTCGGTTT GTTTAGCGTA CCCTTTTTTG            1379
Ala Lys Lys

CGTGTTTTCA ATCCATTTTT CATAATTCGC CTTTTAGGGN NNNGCCGTTT TTATGTAGCG 1439

TATTTGTTGT AGATGGACTA GGTTTTCGGA TTCTCGAACC GGATAGGTGC TATCTTTATC 1499

TTCCTATGTT TTGCTTGTAG AATGGTATGA ATAAACTAGT TTCGAAGTAA TGTTTTTGGT 1559

```
GCACAAACCA GGAAAAAAAA AACCCTCTCT CCCTAACCTA ACTCGCCATC GGAGAAATCT    60

CTGTCGACGG TGACGTTCGA GATCGTAACA ATC ATG CTA TCG AAA GGT GCT CCG    114
                                     Met Leu Ser Lys Gly Ala Pro
                                      1               5

GCG GCA CCG GCG GTG GCG GCG ATG TAC AAT GCC TCC GCC AAA GAC ACT     162
Ala Ala Pro Ala Val Ala Ala Met Tyr Asn Ala Ser Ala Lys Asp Thr
        10                  15                  20

ACT TTT GCC CTA ACT CAC TCC CGA TCG ATT GGT TCC GTC TCA ATT CGC     210
Thr Phe Ala Leu Thr His Ser Arg Ser Ile Gly Ser Val Ser Ile Arg
    25                  30                  35

AGA CGA TAC AAC GTG TTT TTG TGC AAT TCT TCG TCG TCG TCG AGA AAG     258
Arg Arg Tyr Asn Val Phe Leu Cys Asn Ser Ser Ser Ser Ser Arg Lys
40                  45                  50                  55

GTT TCT CCG TTG CTA GCG GTG GCG ACC GGA GAG CAG CCG AGC GGT GTT     306
Val Ser Pro Leu Leu Ala Val Ala Thr Gly Glu Gln Pro Ser Gly Val
                60                  65                  70
```

FIGURE 8A

```
GCT AGT TTA CGT GAG GCG GAT AAG GAG AAG AGC TTG GGG AAC CGG CTA      354
Ala Ser Leu Arg Glu Ala Asp Lys Glu Lys Ser Leu Gly Asn Arg Leu
             75                  80                  85

CGC TTG GGG AGC TTG ACG GAG GAT GGA TTA TCG TAT AAG GAG AAG TTC      402
Arg Leu Gly Ser Leu Thr Glu Asp Gly Leu Ser Tyr Lys Glu Lys Phe
         90                  95                 100

GTT ATA AGG TGT TAT GAA GTC GGA ATT AAC AAA ACT GCT ACG ATT GAA      450
Val Ile Arg Cys Tyr Glu Val Gly Ile Asn Lys Thr Ala Thr Ile Glu
    105                 110                 115

ACG ATT GCA AAT CTG TTG CAG GAG GTT GGA GGT AAT CAT GCT CAG GGT      498
Thr Ile Ala Asn Leu Leu Gln Glu Val Gly Gly Asn His Ala Gln Gly
120                 125                 130                     135

GTT GGA TTT TCT ACT GAT CGG TTT GCC ACA ACG ACC ACT ATG AGG AAA      546
Val Gly Phe Ser Thr Asp Gly Phe Ala Thr Thr Thr Thr Met Arg Lys
                140                 145                 150
```

FIGURE 8B

```
TTG CAT CTC ATA TGG GTT ACT GCA CGA ATG CAT ATT GAA ATA TAT AGA      594
Leu His Leu Ile Trp Val Thr Ala Arg Met His Ile Glu Ile Tyr Arg
            155                 160                 165

TAC CCT GCT TGG AGT GAT GTG ATT GAA ATT GAG ACT TGG GTT CAG GGT      642
Tyr Pro Ala Trp Ser Asp Val Ile Glu Ile Glu Thr Trp Val Gln Gly
        170                 175                 180

GAG GGG AAG GTC GGG ACC AGG CGT GAT TGG ATC CTC AAA GAC TAT GCC      690
Glu Gly Lys Val Gly Thr Arg Arg Asp Trp Ile Leu Lys Asp Tyr Ala
    185                 190                 195

AAT GGT GAG GTT ATT GGA AGG GCC ACA AGC AAA TGG GTG ATG ATG AAC      738
Asn Gly Glu Val Ile Gly Arg Ala Thr Ser Lys Trp Val Met Met Asn
200                 205                 210                 215

GAG GAT ACT AGA AGA TTG CAG AAA GTC AGT GAT GAT GTC AGA GAG GAG      786
Glu Asp Thr Arg Arg Leu Gln Lys Val Ser Asp Asp Val Arg Glu Glu
                220                 225                 230
```

FIGURE 8C

```
TAT TTA GTG TTT TGC CCC AGG ACA TTG AGA TTA GCA TTT CCT GAA GAG      834
Tyr Leu Val Phe Cys Pro Arg Thr Leu Arg Leu Ala Phe Pro Glu Glu
            235                 240                 245

AAC AAC AAT AGC ATG AAG AAA ATA CCA AAA CTG GAA GAT CCA GCT GAA      882
Asn Asn Asn Ser Met Lys Lys Ile Pro Lys Leu Glu Asp Pro Ala Glu
        250                 255                 260

TAT TCC AGG CTT GGA CTT GTG CCA AGG AGA TCC GAT TTG GAT ATG AAC      930
Tyr Ser Arg Leu Gly Leu Val Pro Arg Arg Ser Asp Leu Asp Met Asn
    265                 270                 275

AAA CAC GTT AAC AAT GTT ACC TAC ATC GGG TGG GCT CTA GAG AGC ATC      978
Lys His Val Asn Asn Val Thr Tyr Ile Gly Trp Ala Leu Glu Ser Ile
280                 285                 290                 295

CCA CCA GAA ATC ATC GAC ACC CAT GAA CTG CAA GCT ATT ACC TTA GAC     1026
Pro Pro Glu Ile Ile Asp Thr His Glu Leu Gln Ala Ile Thr Leu Asp
                300                 305                 310
```

FIGURE 8D

```
TAC AGA CGT GAA TGC CAA CGG GAT GAC ATA GTT GAT TCA CTC ACT AGC     1074
Tyr Arg Arg Glu Cys Gln Arg Asp Asp Ile Val Asp Ser Leu Thr Ser
            315                 320                 325

CGT GAA CCA CTC GGA AAT GCT GCA GGT GTC AAG TTT AAA GAA ATC AAT     1122
Arg Glu Pro Leu Gly Asn Ala Ala Gly Val Lys Phe Lys Glu Ile Asn
        330                 335                 340

GGA TCT GTT TCC CCC AAA AAG GAC GAA CAA GAT CTA AGC CGA TTT ATG     1170
Gly Ser Val Ser Pro Lys Lys Asp Glu Gln Asp Leu Ser Arg Phe Met
    345                 350                 355

CAT CTA CTG AGA TCA GCT GGC AGT GGT CTT GAA ATC AAC AGG TGT CGC     1218
His Leu Leu Arg Ser Ala Gly Ser Gly Leu Glu Ile Asn Arg Cys Arg
360                 365                 370                 375

ACC GAA TGG AGA AAG AAG CCA GCA AAA AGA TAAGCATATC TGATCCCTCG       1268
Thr Glu Trp Arg Lys Lys Pro Ala Lys Arg
                380                 385

ATTGTACCGT TTTACCGTTC CTGTTCAAAG TCTAGTTTCT TTTT                    1312
```

FIGURE 8E

```
TCAAC ATG GCC ACC ACC TCT TTA GCT TCT GCT TTC TGC TCG ATG AAA GCT     50
      Met Ala Thr Thr Ser Leu Ala Ser Ala Phe Cys Ser Met Lys Ala
       1               5                  10                  15

GTA ATG TTG GCT CGT GAT GGC AGG GGC ATG AAA CCC AGG AGC AGT GAT       98
Val Met Leu Ala Arg Asp Gly Arg Gly Met Lys Pro Arg Ser Ser Asp
                20                  25                  30

TTG CAG CTG AGG GCG GGA AAT GCA CAA ACC TCT TTG AAG ATG ATC AAT      146
Leu Gln Leu Arg Ala Gly Asn Ala Gln Thr Ser Leu Lys Met Ile Asn
            35                  40                  45

GGG ACC AAG TTC AGT TAC ACA GAG AGC TTG AAA AAG TTG CCT GAC TGG      194
Gly Thr Lys Phe Ser Tyr Thr Glu Ser Leu Lys Lys Leu Pro Asp Trp
        50                  55                  60

AGC ATG CTC TTT GCA GTG ATC ACG ACC ATC TTT TCG GCT GCT GAG AAG      242
Ser Met Leu Phe Ala Val Ile Thr Thr Ile Phe Ser Ala Ala Glu Lys
    65                  70                  75

CAG TGG ACC AAT CTA GAG TGG AAG CCG AAG CCG AAT CCA CCC CAG TTG      290
Gln Trp Thr Asn Leu Glu Trp Lys Pro Lys Pro Asn Pro Pro Gln Leu
80                  85                  90                  95
```

FIGURE 9A

```
CTT GAT GAC CAT TTT GGG CCG CAT GGG TTA GTT TTC AGG CGC ACC TTT     338
Leu Asp Asp His Phe Gly Pro His Gly Leu Val Phe Arg Arg Thr Phe
                100                 105                 110

GCC ATC AGA TCG TAT GAG GTG GGA CCT GAC CGC TCC ACA TCT ATA GTG     386
Ala Ile Arg Ser Tyr Glu Val Gly Pro Asp Arg Ser Thr Ser Ile Val
            115                 120                 125

GCT GTT ATG AAT CAC TTG CAG GAG GCT GCA CTT AAT CAT GCG AAG AGT     434
Ala Val Met Asn His Leu Gln Glu Ala Ala Leu Asn His Ala Lys Ser
        130                 135                 140

GTG GGA ATT CTA GGA GAT GGA TTC GGT ACG ACG CTA GAG ATG AGT AAG     482
Val Gly Ile Leu Gly Asp Gly Phe Gly Thr Thr Leu Glu Met Ser Lys
    145                 150                 155

AGA GAT CTG ATA TGG GTT GTG AAA CGC ACG CAT GTT GCT GTG GAA CGG     530
Arg Asp Leu Ile Trp Val Val Lys Arg Thr His Val Ala Val Glu Arg
160                 165                 170                 175
```

FIGURE 9B

```
TAC CCT GCT TGG GGT GAT ACT GTT GAA GTA GAG TGC TGG GTT GGT GCA      578
Tyr Pro Ala Trp Gly Asp Thr Val Glu Val Glu Cys Trp Val Gly Ala
                180                 185                 190

TCG GGA AAT AAT GGC AGG CGC CAT GAT TTC CTT GTC CGG GAC TGC AAA      626
Ser Gly Asn Asn Gly Arg Arg His Asp Phe Leu Val Arg Asp Cys Lys
            195                 200                 205

ACA GGC GAA ATT CTT ACA AGA TGT ACC AGT CTT TCG GTG ATG ATG AAT      674
Thr Gly Glu Ile Leu Thr Arg Cys Thr Ser Leu Ser Val Met Met Asn
        210                 215                 220

ACA AGG ACA AGG AGG TTG TCC AAA ATC CCT GAA GAA GTT AGA GGG GAG      722
Thr Arg Thr Arg Arg Leu Ser Lys Ile Pro Glu Glu Val Arg Gly Glu
    225                 230                 235

ATA GGG CCT GCA TTC ATT GAT AAT GTG GCT GTC AAG GAC GAG GAA ATT      770
Ile Gly Pro Ala Phe Ile Asp Asn Val Ala Val Lys Asp Glu Glu Ile
240                 245                 250                 255
```

FIGURE 9C

```
AAG AAA CCA CAG AAG CTC AAT GAC AGC ACT GCA GAT TAC ATC CAA GGA      818
Lys Lys Pro Gln Lys Leu Asn Asp Ser Thr Ala Asp Tyr Ile Gln Gly
                260                 265                 270

GGA TTG ACT CCT CGA TGG AAT GAT TTG GAT ATC AAT CAG CAC GTT AAC      866
Gly Leu Thr Pro Arg Trp Asn Asp Leu Asp Ile Asn Gln His Val Asn
            275                 280                 285

AAC ATC AAA TAC GTT GAC TGG ATT CTT GAG ACT GTC CCA GAC TCA ATC      914
Asn Ile Lys Tyr Val Asp Trp Ile Leu Glu Thr Val Pro Asp Ser Ile
        290                 295                 300

TTT GAG AGT CAT CAT ATT TCC AGC TTC ACT ATT GAA TAC AGG AGA GAG      962
Phe Glu Ser His His Ile Ser Ser Phe Thr Ile Glu Tyr Arg Arg Glu
    305                 310                 315

TGC ACG ATG GAT AGC GTG CTG CAG TCC CTG ACC ACT GTC TCC GGT GGC     1010
Cys Thr Met Asp Ser Val Leu Gln Ser Leu Thr Thr Val Ser Gly Gly
320                 325                 330                 335
```

FIGURE 9D

```
TCG TCG GAA GCT GGG TTA GTG TGC GAG CAC TTG CTC CAG CTT GAA GGT      1058
Ser Ser Glu Ala Gly Leu Val Cys Glu His Leu Leu Gln Leu Glu Gly
                340                 345                 350

GGG TCT GAG GTA TTG AGG GCA AAA ACA GAG TGG AGG CCT AAG CTT ACC      1106
Gly Ser Glu Val Leu Arg Ala Lys Thr Glu Trp Arg Pro Lys Leu Thr
            355                 360                 365

GAT AGT TTC AGA GGG ATT AGT GTG ATA CCC GCA GAA TCG AGT GTC          1151
Asp Ser Phe Arg Gly Ile Ser Val Ile Pro Ala Glu Ser Ser Val
        370                 375                 380

TAACTAACGA AAGAAGCATC TGATGAAGTT TCTCCTGTGC TGTTGTTCGT GAGGATGCTT  1211

TTTAGAAGCT GCAGTTTGCA TTGCTTGTGC AGAATCATGG CCTGTGGTTT TAGATATATA  1271

TCCAAAATTG TCCTATAGTC AAGAAACTTA ATATCAGAAA AATAACTCAA TGAGTCAAGG  1331
```

FIGURE 9E

```
TTATCGAAGT AGTCATGTAA GCTTTGAAAT ATGTTGTGTA TTCCTCGGCT TTATGTAATC  1391

TGTAAGCTCT TTCTCTTGCA ATAAATTTCG CCTTTCAATA ATAAAAAAAA AAAAAAAAGG  1451

TCGACTCGAG                                                         1461
```

FIGURE 9F

```
GCTCGCCTCC CACATTTTCT TCTTCGATCC CGAAAAG ATG TTG AAG CTC TCG TGT    55
                                        Met Leu Lys Leu Ser Cys
                                         1               5

AAT GCG ACT GAT AAG TTA CAG ACC CTC TTC TCG CAT TCT CAT CAA CCG    103
Asn Ala Thr Asp Lys Leu Gln Thr Leu Phe Ser His Ser His Gln Pro
            10                  15                  20

GAT CCG GCA CAC CGG AGA ACC GTC TCC TCC GTG TCG TGC TCT CAT CTG    151
Asp Pro Ala His Arg Arg Thr Val Ser Ser Val Ser Cys Ser His Leu
        25                  30                  35

AGG AAA CCG GTT CTC GAT CCT TTG CGA GCG ATC GTA TCT GCT GAT CAA    199
Arg Lys Pro Val Leu Asp Pro Leu Arg Ala Ile Val Ser Ala Asp Gln
    40                  45                  50

GGA AGT GTG ATT CGA GCA GAA CAA GGT TTG GGC TCA CTC GCG GAT CAG    247
Gly Ser Val Ile Arg Ala Glu Gln Gly Leu Gly Ser Leu Ala Asp Gln
55                  60                  65                  70

CTC CGA TTG GGT AGC TTG ACG GAG GAT GGT TTG TCG TAT AAG GAG AAG    295
Leu Arg Leu Gly Ser Leu Thr Glu Asp Gly Leu Ser Tyr Lys Glu Lys
                75                  80                  85

TTC ATC GTC AGA TCC TAC GAA GTG GGG AGT AAC AAG ACC GCC ACT GTC    343
Phe Ile Val Arg Ser Tyr Glu Val Gly Ser Asn Lys Thr Ala Thr Val
            90                  95                  100
```

FIGURE 10A

```
GAA ACC GTC GCT AAT CTT TTG CAG GAG GTG GGA TGT AAT CAT GCG CAG      391
Glu Thr Val Ala Asn Leu Leu Gln Glu Val Gly Cys Asn His Ala Gln
        105                 110                 115

AGC GTT GGA TTC TCG ACT GAT GGG TTT GCG ACA ACA CCG ACC ATG AGG      439
Ser Val Gly Phe Ser Thr Asp Gly Phe Ala Thr Thr Pro Thr Met Arg
    120                 125                 130

AAA CTG CAT CTC ATT TGG GTC ACT GCG AGA ATG CAT ATA GAG ATC TAC      487
Lys Leu His Leu Ile Trp Val Thr Ala Arg Met His Ile Glu Ile Tyr
135                 140                 145                 150

AAG TAC CCT GCT TGG GGT GAT GTG GTT GAG ATA GAG ACA TGG TGT CAG      535
Lys Tyr Pro Ala Trp Gly Asp Val Val Glu Ile Glu Thr Trp Cys Gln
                155                 160                 165

AGT GAA GGA AGG ATC GGG ACT AGG CGT GAT TGG ATT CTT AAG GAT GTT      583
Ser Glu Gly Arg Ile Gly Thr Arg Arg Asp Trp Ile Leu Lys Asp Val
            170                 175                 180

GCT ACG GGT GAA GTC ACT GGC CGT GCT ACA AGC AAG TGG GTG ATG ATG      631
Ala Thr Gly Glu Val Thr Gly Arg Ala Thr Ser Lys Trp Val Met Met
        185                 190                 195

AAC CAA GAC ACA AGA CGG CTT CAG AAA GTT TCT GAT GAT GTT CGG GAC      679
Asn Gln Asp Thr Arg Arg Leu Gln Lys Val Ser Asp Asp Val Arg Asp
    200                 205                 210
```

FIGURE 10B

```
GAG TAC TTG GTC TTC TGT CCT AAA GAA CTC AGA TTA GCA TTT CCT GAG    727
Glu Tyr Leu Val Phe Cys Pro Lys Glu Leu Arg Leu Ala Phe Pro Glu
215                 220                 225                 230

GAG AAT AAC AGA AGC TTG AAG AAA ATT CCG AAA CTC GAA GAT CCA GCT    775
Glu Asn Asn Arg Ser Leu Lys Lys Ile Pro Lys Leu Glu Asp Pro Ala
                235                 240                 245

CAG TAT TCG ATG ATT GGG CTT AAG CCT AGA CGA GCT GAT CTC GAC ATG    823
Gln Tyr Ser Met Ile Gly Leu Lys Pro Arg Arg Ala Asp Leu Asp Met
            250                 255                 260

AAC CAG CAT GTC AAT AAT GTC ACC TAT ATT GGA TGG GTT CTT GAG AGC    871
Asn Gln His Val Asn Asn Val Thr Tyr Ile Gly Trp Val Leu Glu Ser
        265                 270                 275

ATA CCT CAA GAG ATT GTA GAC ACG CAC GAA CTT CAG GTC ATA ACT CTG    919
Ile Pro Gln Glu Ile Val Asp Thr His Glu Leu Gln Val Ile Thr Leu
    280                 285                 290

GAT TAC AGA AGA GAA TGT CAA CAA GAC GAT GTG GTG GAT TCA CTC ACC    967
Asp Tyr Arg Arg Glu Cys Gln Gln Asp Asp Val Val Asp Ser Leu Thr
295                 300                 305                 310

ACT ACC ACC TCA GAG ATT GGT GGG ACC AAT GGC TCT GCA TCA TCA GGC   1015
Thr Thr Thr Ser Glu Ile Gly Gly Thr Asn Gly Ser Ala Ser Ser Gly
                315                 320                 325
```

FIGURE 10C

```
ACA CAG GGG CAA AAC GAT AGC CAG TTC TTA CAT CTC TTA AGG CTG TCT     1063
Thr Gln Gly Gln Asn Asp Ser Gln Phe Leu His Leu Leu Arg Leu Ser
            330                 335                 340

GGA GAC GGT CAG GAG ATC AAC CGC GGG ACA ACC CTG TGG AGA AAG AAG     1111
Gly Asp Gly Gln Glu Ile Asn Arg Gly Thr Thr Leu Trp Arg Lys Lys
        345                 350                 355

CCC TCC AAT CTC TAAGCCATTT CGTTCTTAAG TTTCCTCTAT CTGTGTCGCT         1163
Pro Ser Asn Leu
    360

CGATGCTTCA CGAGTCTAGT CAGGTCTCAT TTTTTTCAAT CTAAATTTGG GTTAGACTAG 1223

AGAACTGGAA TTATTGGAAT TTATGAGTTT TCGTTCTTGT TTCTGTACAA ATCTTGAGGA 1283

TTGAAGCCAA ACCCATTTCA TCTT                                          1307
```

FIGURE 10D

```
CCCAAATCGA CCCCCAATGG CGGTTTGCAG GTTAAGGCAA ACGCCAGCGC CCCTCCTAAG  60

ATCAATGGTT CACCGGTCGG TCTAAAGTCG GNNGGTCTCA AGACTCAGGA AGACGCTCCT 120

TCNNCCCCTC CTCCNCGGAC TTTTATCAAC CAGTTGCCTG ATTGGAGTAT GCTTCTTGCT 180

GCAATCACTA CTGTCTTCTT GGCTGCAGAG AAGCAGTGGA TGATGCTTGA TTGGAAACCA 240

AAGAGGCCTG ACATGCTTGT GGACCCGTTC GGATTGGGAA GTATTGTTCA GGATGGGCTT 300
```

FIGURE 11

```
GGCACGAGGG GCTCCGGTGC TTCAGGTGAA GGCAAGTCCC AAGCTCCACC AAAGCTCAAT  60
GGTTCCAATG TGGGTTTGGT TAAATCTAGC CAAATTGTGA AGAAGGGTGA TGACACCACA 120
TCTCTCCTGC RAGMWYNCAT CAACCAATTG CCTGATTGGA GCATNNNTCT TGCTGCTATC 180
ACAACCCNTG TNCTTGGCTG CAGAGAAGCA GTGGATNATG CWNGANNTTG GAAACCCAAA 240
AGGCCTGACA TGCTTNTTGA TCCATTTGGT CTTGGAAGGT TTGTTCAGGA TGGTCTTGTT 300
TTCCGCAACA ACTTTTCAAT TCGATCATAT AAATAGGGGC TGATCGAACG GCTTCTATAG 360
AAANCGTTAA TGAATCATCT GCAGGNMACR RSTCTTAATC ATGTGAAGTC TGTTGGGCTT 420
CTTGAGGATG GCCTAGGTTC GACTCGAGAG ATGTCCTTGA GGAACCTGAT ATGGGTTGTC 480
ACTAAAATGC AGGTTGCGGT TGATCGCTAT CCAACTTGGG GAGATGAAGT TCTGGTATCC 540
TCTTNGCTAC TGCAATTGGA AAGAATGGAA TCCTCGCGAA T                     581
```

FIGURE 12

```
GG CTT CTC CCA ATT CAT CGT TGT TAT CGC TAC CAC TTC CGC CAC CAC    47
   Leu Leu Pro Ile His Arg Cys Tyr Arg Tyr His Phe Arg His His
    1               5                  10                  15

CCC ACC ACC ATG CAA GCC CTG CAG TCC CCG TCT CTC CGA CCA TCC CCT    95
Pro Thr Thr Met Gln Ala Leu Gln Ser Pro Ser Leu Arg Pro Ser Pro
                20                  25                  30

CTA ACC CCG CTC CAT AAA AAT ACT CAC AAT GCA GCA AAA CGC CCA ACT   143
Leu Thr Pr  Leu His Lys Asn Thr His Asn Ala Ala Lys Arg Pro Thr
            35                  40                  45

AAA AAG GTC TCC TTT ATC ACC GCA TCA TCA ACA AAT AAC AAC ACG ACG   191
Lys Lys Val Ser Phe Ile Thr Ala Ser Ser Thr Asn Asn Asn Thr Thr
        50                  55                  60

ATT TCA GCT CCA AAG CCA GAG AAA GAC CCC AGA AAA AGG GTA GTC ATA   239
Ile Ser Ala Pro Lys Arg Glu Lys Asp Pro Arg Lys Arg Val Val Ile
    65                  70                  75

ACT GGT ACG GGT TTG GTA TCT GTG TTT GGG AAT GAT GTC GAT ACT TAC   287
Thr Gly Thr Gly Leu Val Ser Val Phe Gly Asn Asp Val Asp Thr Tyr
80                  85                  90                  95

TAC GAT AAA TTG CTT GCT GGA GAA AGT GGG ATC GGA CTT ATT GAT AGG   335
Tyr Asp Lys Leu Leu Ala Gly Glu Ser Gly Ile Gly Leu Ile Asp Arg
                100                 105                 110
```

FIGURE 13A

```
TTC GAT GCG TCT AAG TTT CCT ACT AGA TTT GGT GGA CAG ATC AGG GGG      383
Phe Asp Ala Ser Lys Phe Pro Thr Arg Phe Gly Gly Gln Ile Arg Gly
            115                 120                 125

TTT AAT TCA CAA GGT TAT ATT GAT GGG AAA AAT GAT AGA AGG CTT GAT      431
Phe Asn Ser Gln Gly Tyr Ile Asp Gly Lys Asn Asp Arg Arg Leu Asp
        130                 135                 140

GAT TGT TTG AGG TAT TGC ATT GTT GCT GGT AAA AAA GCT CTT GAG CAT      479
Asp Cys Leu Arg Tyr Cys Ile Val Ala Gly Lys Lys Ala Leu Glu His
    145                 150                 155

GCT GAT CTT GGT GGT GAT AAG TTG TCT AAG ATT GAT AAA GAG CGA GCT      527
Ala Asp Leu Gly Gly Asp Lys Leu Ser Lys Ile Asp Lys Glu Arg Ala
160                 165                 170                 175

GGT GTG CTT GTT GGA ACA GGG ATC GGT GGT CTT ACA GTC TTT TCA GAT      575
Gly Val Leu Val Gly Thr Gly Met Gly Gly Leu Thr Val Phe Ser Asp
                180                 185                 190

GGT GTT CAG GCC CTA ATT GAA AAA GGA CAC AGG AAA ATT ACC CCA TTC      623
Gly Val Gln Ala Leu Ile Glu Lys Gly His Arg Lys Ile Thr Pro Phe
            195                 200                 205

TTT ATT CCT TAT GCT ATA ACA AAC ATG GGA TCT GCC TTG TTA GCT ATT      671
Phe Ile Pro Tyr Ala Ile Thr Asn Met Gly Ser Ala Leu Leu Ala Ile
        210                 215                 220
```

FIGURE 13B

```
GAA CTT GGT CTC ATG GGT CCT AAT TAT TCA ATT TCA ACT GCT TGT GCT      719
Glu Leu Gly Leu Met Gly Pro Asn Tyr Ser Ile Ser Thr Ala Cys Ala
    225                 230                 235

ACC TCC AAT TAT TGC TTC TAT GCT GCT GCC AAT CAT ATT CGC AGA GGT      767
Thr Ser Asn Tyr Cys Phe Tyr Ala Ala Ala Asn His Ile Arg Arg Gly
240                 245                 250                 255

GAG GCT GAA TTG ATG ATT GCT GGT GGA ACT GAA GCC GCC ATC ATT CCA      815
Glu Ala Glu Leu Met Ile Ala Gly Gly Thr Glu Ala Ala Ile Ile Pro
                260                 265                 270

ATC GGT TTG GGA GGT TTT GTA GCA TGT AGG GCC TTA TCA CAA AGG AAT      863
Ile Gly Leu Gly Gly Phe Val Ala Cys Arg Ala Leu Ser Gln Arg Asn
            275                 280                 285

GAT GAT CCA CAA ACT GCC TCA AGG CCA TGG GAC AAA GAT CGA GAT GGC      911
Asp Asp Pro Gln Thr Ala Ser Arg Pro Trp Asp Lys Asp Arg Asp Gly
        290                 295                 300

TTT GTT ATG GGT GAA GGT GCT GGA GTG TTG GTA ATG GAG AGT TTG GAA      959
Phe Val Met Gly Glu Gly Ala Gly Val Leu Val Met Glu Ser Leu Glu
    305                 310                 315

CAT GCA ATG AAA AGG GGT GCA CCA ATA ATT GCT GAG TAC TTG GGA GGT     1007
His Ala Met Lys Arg Gly Ala Pro Ile Ile Ala Glu Tyr Leu Gly Gly
320                 325                 330                 335

GCT GTT AAT TGT GAT GCT TAT CAC ATG ACT GAT CCA AGG GCT GAT GGA     1055
Ala Val Asn Cys Asp Ala Tyr His Met Thr Asp Pro Arg Ala Asp Gly
                340                 345                 350
```

FIGURE 13C

```
CTT GGG GTC TCT TCC TGC ATT GAG AGA AGT CTT GAA GAT GCC GGT GTG    1103
Leu Gly Val Ser Ser Cys Ile Glu Arg Ser Leu Glu Asp Ala Gly Val
            355                 360                 365

TCA CCT GAG GAG GTT AAC TAT ATA AAT GCA CAT GCA ACT TCC ACT CTT    1151
Ser Pro Glu Glu Val Asn Tyr Ile Asn Ala His Ala Thr Ser Thr Leu
        370                 375                 380

GCT GGT GAC CTT GCT GAG ATA AAT GCT ATT AAA AAA GTA TTC AAG AAT    1199
Ala Gly Asp Leu Ala Glu Ile Asn Ala Ile Lys Lys Val Phe Lys Asn
    385                 390                 395

ACG TCT GAC ATC AAA ATC AAT GCA ACC AAG TCT ATG ATA GGA CAT TGC    1247
Thr Ser Asp Ile Lys Ile Asn Ala Thr Lys Ser Met Ile Gly His Cys
400                 405                 410                 415

CTT GGT GCT GCT GGA GGT CTG GAA GCA ATT GCC TGT GTG AAG GCC ATT    1295
Leu Gly Ala Ala Gly Gly Leu Glu Ala Ile Ala Cys Val Lys Ala Ile
                420                 425                 430

ACC ACA GGA TGG TTG CAT CCT ACA ATT AAT CAA TTT AAC CCA GAG CCA    1343
Thr Thr Gly Trp Leu His Pro Thr Ile Asn Gln Phe Asn Pro Glu Pro
            435                 440                 445

TCA GTT GAA TTT GAC ACT GTT GCC AAT AAG AAG CAG CAG CAC GAA GTG    1391
Ser Val Glu Phe Asp Thr Val Ala Asn Lys Lys Gln Gln His Glu Val
        450                 455                 460

AAT GTT GCC ATT TCA AAT TCC TTT GGA TTC GGT GGA CAC AAC TCT GTG    1439
Asn Val Ala Ile Ser Asn Ser Phe Gly Phe Gly Gly His Asn Ser Val
    465                 470                 475
```

FIGURE 13D

```
GTA GCC TTT TCT GCA TTT AAA CCC TGAGAGCATG GCCTTCTTCT GCATTCGGGC  1493
Val Ala Phe Ser Ala Phe Lys Pro
480                 485

CGCGGTCATT TACATTTACC ATGGCCTGCA TTTCTTGTAG GAACCACTGC AGAGTTGCTT 1553

GCTTATAGAC AGAGTCATCG ACATCACTTC CCCCTTTTAG CTTTTTGAGC TGCTGATAGT 1613

AGTCAGTTTC TCATTTCAGT ATCAAGTCTA TCTTAAGAAG GTCTTGCTTA ATTTTTCTTT 1673

TCAAATTACC ATTTCATTGT CATTTTCCTT GGAACTTTTA GCTTAAGATC TGCTGTGATC 1733

ATGTGGTTTT GATTTCAAAT TAATTATGTA GCGGATACGA ACAAGCAATC ATAAAAAGTC 1793

TTTTTGAATT ATGTAATTAC GATAACTGTT ATTTTCTTTT TCAAAAAAAA AA         1845
```

FIGURE 13E

```
C CCC GTG GCG GCG TGC ATG TCG GTC ACG TGC TCA AAG GAG AAC AGA CAC    49
  Pro Val Ala Ala Cys Met Ser Val Thr Cys Ser Lys Glu Asn Arg His
   1               5                  10                  15

GCG TTC TTC TCT TCA TCG ACA CCG GGC ACC ACC AGC AGT CAC AGT CGT      97
Ala Phe Phe Ser Ser Ser Thr Pro Gly Thr Thr Ser Ser His Ser Arg
            20                  25                  30

ACA AGA AGG AGG CCT AAA TAT AAT AGT ATC AGC ACC CCT GCC TCT CAA     145
Thr Arg Arg Arg Pro Lys Tyr Asn Ser Ile Ser Thr Pro Ala Ser Gln
        35                  40                  45

TCT TTC TTT AAT TCT TTA TCA TCT TCT GGA TCG AGT TTT CAA CAA TTA     193
Ser Phe Phe Asn Ser Leu Ser Ser Ser Gly Ser Ser Phe Gln Gln Leu
    50                  55                  60

ATG TCT TCT TGC TTG GCC TTC GAG CCT TGT AGT CAT TAC TAC AGC TCT     241
Met Ser Ser Cys Leu Ala Phe Glu Pro Cys Ser His Tyr Tyr Ser Ser
65                  70                  75                  80

AAT GGC CTC TTT CCT AAC ACT CCT CTT CTT CCT AAG CGC CAT CCT AGA     289
Asn Gly Leu Phe Pro Asn Thr Pro Leu Leu Pro Lys Arg His Pro Arg
                85                  90                  95

CTT CAT CAT CGC CTT CCT CGT TCT GGG GAA GCA ATG GCA GTG GCT GTG     337
Leu His His Arg Leu Pro Arg Ser Gly Glu Ala Met Ala Val Ala Val
            100                 105                 110
```

FIGURE 14A

```
CAA CCT GAA AAG GAG GTT GCA ACA AAT AAG AAA CCT CTT ATG AAG CAA      385
Gln Pro Glu Lys Glu Val Ala Thr Asn Lys Lys Pro Leu Met Lys Gln
        115                 120                 125

AGG AGA GTA GTT GTT ACT GGG ATG GGT GTT GTT TCA CCC CTT GGT CAT      433
Arg Arg Val Val Val Thr Gly Met Gly Val Val Ser Pro Leu Gly His
    130                 135                 140

GAT ATA GAC GTC TAT TAC AAT AAT CTT CTT GAC GGT TCT AGT GGT ATT      481
Asp Ile Asp Val Tyr Tyr Asn Asn Leu Leu Asp Gly Ser Ser Gly Ile
145                 150                 155                 160

AGT CAG ATT GAT TCC TTT GAC TGT GCC CAA TTT CCT ACG AGG ATT GCT      529
Ser Gln Ile Asp Ser Phe Asp Cys Ala Gln Phe Pro Thr Arg Ile Ala
                165                 170                 175

GGA GAG ATC AAG TCT TTC TCA ACT GAT GGA TGG GTT GCA CCA AAA CTT      577
Gly Glu Ile Lys Ser Phe Ser Thr Asp Gly Trp Val Ala Pro Lys Leu
            180                 185                 190

TCC AAG AGA ATG GAT AAA TTC ATG CTT TAC ATG CTT ACT GCT GGC AAA      625
Ser Lys Arg Met Asp Lys Phe Met Leu Tyr Met Leu Thr Ala Gly Lys
        195                 200                 205

AAA GCC TTG GCA GAT GGT GGT ATT ACA GAG GAT ATG ATG GAT GAA TTG      673
Lys Ala Leu Ala Asp Gly Gly Ile Thr Glu Asp Met Met Asp Glu Leu
    210                 215                 220
```

FIGURE 14B

```
GAT AAA GCT AGA TGT GGA GTT TTA ATT GGT TCT GCA ATG GGT GGC ATG      721
Asp Lys Ala Arg Cys Gly Val Leu Ile Gly Ser Ala Met Gly Gly Met
225                 230                 235                 240

AAG GTT TTC AAT GAT GCA ATT GAA GCA TTA AGG ATC TCG TAT AGG AAG      769
Lys Val Phe Asn Asp Ala Ile Glu Ala Leu Arg Ile Ser Tyr Arg Lys
                245                 250                 255

ATG AAT CCT TTC TGC GTA CCT TTT GCG ACT ACA AAT ATG GGC TCT GCC      817
Met Asn Pro Phe Cys Val Pro Phe Ala Thr Thr Asn Met Gly Ser Ala
            260                 265                 270

ATG CTT GCA ATG GAC CTT GGT TGG ATG GGG CCA AAC TAT TCA ATA TCT      865
Met Leu Ala Met Asp Leu Gly Trp Met Gly Pro Asn Tyr Ser Ile Ser
        275                 280                 285

ACT GCT TGT GCT ACT AGC AAT TTT TGT ATA TTG AAT GCC GCA AAC CAC      913
Thr Ala Cys Ala Thr Ser Asn Phe Cys Ile Leu Asn Ala Ala Asn His
    290                 295                 300

ATC ATT AGA GGC GAA GCT GAT ATT ATG CTT TGT GGT GGC TCA GAT GCA      961
Ile Ile Arg Gly Glu Ala Asp Ile Met Leu Cys Gly Gly Ser Asp Ala
305                 310                 315                 320

GCA ATT ATA CCT ATT GGC TTG GGA GGT TTT GTG GCA TGC AGA GCG CTC     1009
Ala Ile Ile Pro Ile Gly Leu Gly Gly Phe Val Ala Cys Arg Ala Leu
                325                 330                 335
```

FIGURE 14C

```
TCA CAG AGG AAT GAT GAT CCT ACA AAA GCT TCA CGA CCT TGG GAT ATG    1057
Ser Gln Arg Asn Asp Asp Pro Thr Lys Ala Ser Arg Pro Trp Asp Met
            340                 345                 350

AAT CGG GAT GGA TTT GTG ATG GGG GAA GGA GCT GGT GTT CTT CTT TTA    1105
Asn Arg Asp Gly Phe Val Met Gly Glu Gly Ala Gly Val Leu Leu Leu
        355                 360                 365

GAA GAA CTA GAA CAT GCT AAG AAA AGA GGT GCA AAT ATT TAT GCG GAA    1153
Glu Glu Leu Glu His Ala Lys Lys Arg Gly Ala Asn Ile Tyr Ala Glu
    370                 375                 380

TTT CTT GGA GGA AGC TTT ACA TGT GAT GCT TAT CAC ATG ACT GAA CCG    1201
Phe Leu Gly Gly Ser Phe Thr Cys Asp Ala Tyr His Met Thr Glu Pro
385                 390                 395                 400

CGT CCA GAT GGA GTT GGT GTC ATT CTC TGT ATA GAA AAG GCA TTA GCG    1249
Arg Pro Asp Gly Val Gly Val Ile Leu Cys Ile Glu Lys Ala Leu Ala
                405                 410                 415

CGA TCT GGT GTA TCC AAG GAG GAA GTA AAC TAC ATA AAT GCA CAT GCT    1297
Arg Ser Gly Val Ser Lys Glu Glu Val Asn Tyr Ile Asn Ala His Ala
            420                 425                 430

ACG TCT ACC CCA GCT GGA GAC CTT AAA GAA TAT GAA GCT CTT ATG CGC    1345
Thr Ser Thr Pro Ala Gly Asp Leu Lys Glu Tyr Glu Ala Leu Met Arg
        435                 440                 445
```

FIGURE 14D

```
TGT TTC AGC CAA AAT CCT GAT TTG AGA GTG AAC TCT ACG AAG TCT ATG     1393
Cys Phe Ser Gln Asn Pro Asp Leu Arg Val Asn Ser Thr Lys Ser Met
    450                 455                 460

ATT GGC CAT TTA CTA GGA GCA GCT GGT GCT GTG GAA GCT ATA GCA ACA     1441
Ile Gly His Leu Leu Gly Ala Ala Gly Ala Val Glu Ala Ile Ala Thr
465                 470                 475                 480

ATA CAG GCG ATA CGG ACA GGA TGG GTT CAT CCA AAC ATC AAC CTG GAA     1489
Ile Gln Ala Ile Arg Thr Gly Trp Val His Pro Asn Ile Asn Leu Glu
                485                 490                 495

AAC CCA GAA GAA GGC GTG GAC ACA AAG GTG CTG GTT GGC CCA AAG AAG     1537
Asn Pro Glu Glu Gly Val Asp Thr Lys Val Leu Val Gly Pro Lys Lys
            500                 505                 510

GAG AGA TTG GAC ATT AAG GTT GCT CTG TCC AAC TCT TTT GGG TTC GGT     1585
Glu Arg Leu Asp Ile Lys Val Ala Leu Ser Asn Ser Phe Gly Phe Gly
        515                 520                 525

GGG CAC AAC TCA TCG ATC ATT TTT GCT CCG TAC AAG TGAAATAAGG         1631
Gly His Asn Ser Ser Ile Ile Phe Ala Pro Tyr Lys
    530                 535                 540

GGTACTTCAA CTTTGGTGTA TTAACGTGAA AGATGATCTA AAATGGAACA AGATTAGATA 1691

ACTCTATGGG TAGGGAAAGG AGAATATGCC GAGTTCACAG AGAGGAAACT TCCCGTGAAG 1751
```

FIGURE 14E

```
ATTCCTGTGC CTTCTACCAT TTTCAGTATT CTCTCCGCAT CATTGTGGCT TGATCCATGT 1811
TGATCCATCG AATACCAGTA ACAGTGGCCT TATTTAATTT TTGTTCCATG TATAAGCAGA 1871
CGGCTGATCG TTGCTTTAAC AGTCAATTGT AATGAATTTT TGAGCTGGAC AGTTGGCTAG 1931
GTTACACTAA TGTAATGGTG GTTTTATGAG CAAAAAAA                         1969
```

FIGURE 14F

```
AT GCG AGA CAG CCC ACG AGA AGA CGC TCA TTC ATC TCC GCG TCG TCC TCC   50
   Ala Arg Gln Pro Thr Arg Arg Arg Ser Phe Ile Ser Ala Ser Ser Ser
    1               5                   10                  15

GCC GTC TCC GCC CCC AAA CGC GAA ACA GAC CCG AAG AAA CGG GTC GTA      98
Ala Val Ser Ala Pro Lys Arg Glu Thr Asp Pro Lys Lys Arg Val Val
            20                  25                  30

ATC ACC GGA ATG GGC CTC GTC TCC GTC TTC GGA AAC GAC GTC GAC GCT     146
Ile Thr Gly Met Gly Leu Val Ser Val Phe Gly Asn Asp Val Asp Ala
        35                  40                  45

TAC TAC GAG AAG CTG CTC TCC GGC GAG AGT GGA ATC AGC TTG ATT GAT     194
Tyr Tyr Glu Lys Leu Leu Ser Gly Glu Ser Gly Ile Ser Leu Ile Asp
    50                  55                  60

CGG TTC GAC GCC TCC AAG TTC CCG ACC CGA TTC GGT GGA CAG ATC CGT     242
Arg Phe Asp Ala Ser Lys Phe Pro Thr Arg Phe Gly Gly Gln Ile Arg
65                  70                  75                  80

GGG TTC AGC TCA GAG GGT TAC ATC GAT GGG AAG AAT GAG CGG AGG CTT     290
Gly Phe Ser Ser Glu Gly Tyr Ile Asp Gly Lys Asn Glu Arg Arg Leu
                85                  90                  95

GAT GAT TGC TTG AAG TAC TGC ATT GTC GCT GGG AAG AAG GCT CTT GAA     338
Asp Asp Cys Leu Lys Tyr Cys Ile Val Ala Gly Lys Lys Ala Leu Glu
            100                 105                 110

AGT GCG AAT CTT GGT GGT GAT AAG CTT AAC ACG ATT GAT AAG CAG AAA     386
Ser Ala Asn Leu Gly Gly Asp Lys Leu Asn Thr Ile Asp Lys Gln Lys
        115                 120                 125
```

FIGURE 15A

```
GCT GGA GTA CTA GTT GGG ACT GGT ATG GGT GGC TTG ACT GTG TTT TCA    434
Ala Gly Val Leu Val Gly Thr Gly Met Gly Gly Leu Thr Val Phe Ser
    130                 135                 140

GAC GGT GTT CAA GCT CTT ATT GAG AAA GGT CAC AGG AGG ATT TCT CCT    482
Asp Gly Val Gln Ala Leu Ile Glu Lys Gly His Arg Arg Ile Ser Pro
145                 150                 155                 160

TTC TTT ATT CCT TAT GCT ATT ACA AAC ATG GGT TCT GCT TTG TTG GCG    530
Phe Phe Ile Pro Tyr Ala Ile Thr Asn Met Gly Ser Ala Leu Leu Ala
                165                 170                 175

ATT GAT CTT GGT CTT ATG GGT CCT AAC TAC TCG ATC TCG ACG GCT TGT    578
Ile Asp Leu Gly Leu Met Gly Pro Asn Tyr Ser Ile Ser Thr Ala Cys
            180                 185                 190

GCC ACT TCT AAC TAC TGC TTT TAC GCT GCT GCG AAT CAC ATT CGA CGT    626
Ala Thr Ser Asn Tyr Cys Phe Tyr Ala Ala Ala Asn His Ile Arg Arg
        195                 200                 205

GGT GAA GCT GAT ATG ATG ATA GCT GGT GGA ACC GAG GCT GCT ATT ATT    674
Gly Glu Ala Asp Met Met Ile Ala Gly Gly Thr Glu Ala Ala Ile Ile
    210                 215                 220

CCT ATT GGT TTG GGA GGT TTT GTT GCT TGT AGG GCG CTT TCA CAG AGA    722
Pro Ile Gly Leu Gly Gly Phe Val Ala Cys Arg Ala Leu Ser Gln Arg
225                 230                 235                 240

AAT GAT GAT CCT CAG ACG GCT TCA AGG CCG TGG GAT AAA CAG AGA GAT    770
Asn Asp Asp Pro Gln Thr Ala Ser Arg Pro Trp Asp Lys Gln Arg Asp
                245                 250                 255
```

FIGURE 15B

```
GGG TTT GTC ATG GGT GAA GGA GCT GGT GTT CTG GTG ATG GAA AGC TTG      818
Gly Phe Val Met Gly Glu Gly Ala Gly Val Leu Val Met Glu Ser Leu
            260                 265                 270

GAA CAT GCG ATG AAA CGT GGT GCT CCA ATT GTA GCA GAG TAT CTT GGA      866
Glu His Ala Met Lys Arg Gly Ala Pro Ile Val Ala Glu Tyr Leu Gly
        275                 280                 285

GGC GCT GTT AAC TGC GAT GCT CAT CAT ATG ACT GAT CCA AGA GCT GAT      914
Gly Ala Val Asn Cys Asp Ala His His Met Thr Asp Pro Arg Ala Asp
    290                 295                 300

GGG CTT GGT GTG TCT TCA TGC ATT GAG AGC TGC CTT GAA GAT GCT GGT      962
Gly Leu Gly Val Ser Ser Cys Ile Glu Ser Cys Leu Glu Asp Ala Gly
305                 310                 315                 320

GTA TCA CCT GAG GAG GTA AAT TAC ATC AAT GCA CAT GCA ACT TCC ACA     1010
Val Ser Pro Glu Glu Val Asn Tyr Ile Asn Ala His Ala Thr Ser Thr
                325                 330                 335

CTG GCT GGT GAT CTT GCT GAG ATT AAT GCC ATT AAA AAG GTA TTC AAA     1058
Leu Ala Gly Asp Leu Ala Glu Ile Asn Ala Ile Lys Lys Val Phe Lys
            340                 345                 350

AGC ACT TCA GGG ATC AAA ATC AAT GCC ACC AAG TCT ATG ATA GGT CAC     1106
Ser Thr Ser Gly Ile Lys Ile Asn Ala Thr Lys Ser Met Ile Gly His
        355                 360                 365

TGC CTC GGT GCA GCT GGA GGT CTT GAA GCC ATT GCC ACC GTG AAG GCT     1154
Cys Leu Gly Ala Ala Gly Gly Leu Glu Ala Ile Ala Thr Val Lys Ala
    370                 375                 380
```

FIGURE 15C

```
ATC AAC ACG GGA TGG CTG CAT CCC TCT ATC AAC CAA TTT AAC CCA GAA    1202
Ile Asn Thr Gly Trp Leu His Pro Ser Ile Asn Gln Phe Asn Pro Glu
385                 390                 395                 400

CCA GCA GTG GAC TTT GAT ACG GTC GCA AAC GAG AAG AAG CAG CAT GAG    1250
Pro Ala Val Asp Phe Asp Thr Val Ala Asn Glu Lys Lys Gln His Glu
                405                 410                 415

GTG AAT GTT GCC ATA TCA AAC TCG TTT GGG TTC GGT GGA CAT AAC TCA    1298
Val Asn Val Ala Ile Ser Asn Ser Phe Gly Phe Gly Gly His Asn Ser
            420                 425                 430

GTG GTC GCT TTC TCT GCC TTC AAA CCC TGATTTCCTC AGACCCTTTA          1345
Val Val Ala Phe Ser Ala Phe Lys Pro
        435                 440

GATCCTCTGG TCCATCTGTT AGATCACCAC CATCATCTTC TTCGCAGCTT CTTGGTTCAC 1405

AAGTTGAGCG CTTTCTTCCT TTCAGCTTTT TGTTCTTATT GGTCATTGTT AATTTTTGCT 1465

CAACTCTTAT TGGTCATTGA GGTGTAGAGA ATCCAGATTT TGCTTCTACA ATCTGTGTAC 1525

GGAATGTTGT ATCTTTAGTT CGTTTTATGT TTGCCAAATT TTATAAAC               1573
```

FIGURE 15D

```
CCCCCCGACG CGTCCAAACA CTCAAGTGTG AGAGAGAGAT CAGATAATCT TTCTCGTTTT   60
CTCCACCTTC ATCCGAGTAT GACGATGGGT GGTGCGTCTT TATGCGATTC ACTAGTGGCT  120
GCTTGCATGT CCTCCGCCTC GCACTCAAGC GGAGACCGAC TGACTCAATT CATCTGGCCT  180
CGCCGGAGTA GACTGGTTAA CAACTGCTCG CTCCATGGAT CCCAGGCGAG TTCCCGTAAC  240
AACAATGCCT CGTCTTCCCT CTTCGAATCG AATAACACTT CCTTCAATCC AAAGCAGAGG  300
AGATTCAATC GAGCATCAAC CTCTGGGCAA GTCACTACAC TAGAGATGGA GAAGGACGCA  360
ATGGTAAACA AGCCACGCCG AGTTGTTGTC ACTGGCATGG GAGTTGAAAC ACCACTAGGT  420
CACGACCCTC ATACTTTTTA TGACAACTTG CTACAAGGCA AAAGTGGTAT AAGCCATATA  480
GAGAGTTTCG ACTGTTCTGC ATTTCCCACT AGAATCGCTG GGGAGATTAA ATCTTTTTCG  540
ACCGACGGAT TGGTTGCTCC TAAACTTTCC AAAAGGATGG ACAAGTTCAT GCTCTACCTT  600
```

FIGURE 16A

```
CTAACCGCCG GCAAGAAGGC GTTGGAGGAT GGTGGGGTGA CTGGGGATGT GATGGCAGAG  660
TTCGACAAAT CAAGATGTGG TGTCTTGATT GGCTCAGCAA TGGGAGGCAT GAAGGTCTTT  720
TACGATGCGC TTGAAGCTTT GAAAATCTCT TACAGGAAGA TGAACCCTTT TTGTGTACCT  780
TTTGCCACCA CAAACATGGG TTCCGCTATG CTTGCCTTGG ATCTGGGATG GATGGGTCCA  840
AACTACTCTA TTTCAACCGC ATGTGCCACG GGAAACTTCT GTATTCTCAA TGCGGCAAAC  900
CACATTACCA GAGGTGAAGC TGATGTAATG CTCTGTGGTG GCTCTGACTC AGTTATTATT  960
CCAATAGGGT TGGGAGGTTT TGTTGCCTGC CGGGCTCTTT CAGAAAATAA TGATGATCCC 1020
ACCAAAGCTT CTCGTCCTTG GGATAGTAAC CGAGATGGTT TTGTTATGGG AGAGGGAGCC 1080
GGAGTTCTAC TTTTAGAAGA ACTTGAGCAT GCCAAGAGGA GCAACTATAT ACGCAGAGTT 1140
CCTTGGGGGT AGTTTCACAT GTGATGCATA CCATATAACC GAACCACGTC CTGATGGTGC 1200
```

FIGURE 16B

```
TGGTGTCATT CTTGCTATCG AGAAAGCGGT AGCTCATGCC GGGATTTCTA AGGAAGACAT 1260
AAATTACGTG AATGCTCATG CTACCTCTAC ACCAGCTGGA GACCTTAAGG AGTACCACGC 1320
TCTTTCTCAC TGTTTTGGCC AAAATCCTGA GCTAAGAGTA AACTCAACAA AATCTATGAT 1380
TGGACACTTG CTGGGAGCTT CTGGGGCCGT GGAGGCTGTT GCAACCGTTC AGGCAATAAA 1440
GACAGGATGG GTTCATCCAA ATATCAACCT CGAGAATCCA GACAAAGCAG TGGATACAAA 1500
GCTTTTGGTG GGTCTTAAGA AGGAGAGACT GGATATCAAA GCAGCCTTGT CAAACTCTTT 1560
CGGCTTTGGT GGCCAGAACT CTAGCATAAT TTTCGCTCCT TACAAATGAA AGGCGAATAG 1620
TCCAATGCTG TGTACTCTTG TGTAACTTGC TGTAAGTGTG TACAAGAACT TCCCATGTTT 1680
TGATGCAATA TGTACGAGAA CTTCCCATGC TTTTGGTAGT GCCATGATTC AGGATTCGAT 1740
TAACTTGCAC AAAGAGTTTA AGCAACGTTG AAAAGAGAGA GAAAAAAAAA GTGATGAGGT 1800
```

FIGURE 16C

```
AGCTGAGGAT TTGTCAGGAA CAACAATACT TCATTTTTCA CTTTGGTTAG GTAGACTGAA 1860

ATATTTGAGC CAACATTTCT TGTATTTTTA TTCTTTGAAA GCTTTAACCA AAGAAAAAAA 1920

```
AAATCCTCCA CTCATACACT CCACTTCTCT CTCTCTCTCT CTCTCTCTGA AACAATTTGA    60

GTAGCAAACT TAAAAGAAA ATG GAG GAA ATG GGA AGC ATT TTA GAG TTT CTT    112
                     Met Glu Glu Met Gly Ser Ile Leu Glu Phe Leu
                     1               5                   10

GAT AAC AAA GCC ATT TTG GTC ACT GGT GCT ACT GGC TCC TTA GCA AAA    160
Asp Asn Lys Ala Ile Leu Val Thr Gly Ala Thr Gly Ser Leu Ala Lys
            15                  20                  25

ATT TTT GTG GAG AAG GTA CTG AGG AGT CAA CCG AAT GTG AAG AAA CTC    208
Ile Phe Val Glu Lys Val Leu Arg Ser Gln Pro Asn Val Lys Lys Leu
        30                  35                  40

TAT CTT CTT TTG AGA GCA ACC GAT GAC GAG ACA GCT GCT CTA CGC TTG    256
Tyr Leu Leu Leu Arg Ala Thr Asp Asp Glu Thr Ala Ala Leu Arg Leu
    45                  50                  55

CAA AAT GAG GTT TTT GGA AAA GAG TTG TTC AAA GTT CTG AAA CAA AAT    304
Gln Asn Glu Val Phe Gly Lys Glu Leu Phe Lys Val Leu Lys Gln Asn
60                  65                  70                  75
```

FIGURE 17A

```
TTA GGT GCA AAT TTC TAT TCC TTT GTA TCA GAA AAA GTG ACT GTA GTA     352
Leu Gly Ala Asn Phe Tyr Ser Phe Val Ser Glu Lys Val Thr Val Val
                 80                  85                  90

CCC GGT GAT ATT ACT GGT GAA GAC TTG TGT CTC AAA GAC GTC AAT TTG     400
Pro Gly Asp Ile Thr Gly Glu Asp Leu Cys Leu Lys Asp Val Asn Leu
             95                  100                 105

AAG GAA GAA ATG TGG AGG GAA ATC GAT GTT GTT GTC AAT CTA GCT GCT     448
Lys Glu Glu Met Trp Arg Glu Ile Asp Val Val Val Asn Leu Ala Ala
        110                 115                 120

ACA ATC AAC TTC ATT GAA AGG TAC GAC GTG TCT CTG CTT ATC AAC ACA     496
Thr Ile Asn Phe Ile Glu Arg Tyr Asp Val Ser Leu Leu Ile Asn Thr
    125                 130                 135

TAT GGA GCC AAG TAT GTT TTG GAC TTC GCG AAG AAG TGC AAC AAA TTA     544
Tyr Gly Ala Lys Tyr Val Leu Asp Phe Ala Lys Lys Cys Asn Lys Leu
140                 145                 150                 155

AAG ATA TTT GTT CAT GTA TCT ACT GCT TAT GTA TCT GGA GAG AAA AAT     592
Lys Ile Phe Val His Val Ser Thr Ala Tyr Val Ser Gly Glu Lys Asn
                160                 165                 170
```

FIGURE 17B

```
GGG TTA ATA CTG GAG AAG CCT TAT TAT ATG GGC GAG TCA CTT AAT GGA     640
Gly Leu Ile Leu Glu Lys Pro Tyr Tyr Met Gly Glu Ser Leu Asn Gly
            175                 180                 185

AGA TTA GGT CTG GAC ATT AAT GTA GAG AAG AAA CTT GTG GAG GCA AAA     688
Arg Leu Gly Leu Asp Ile Asn Val Glu Lys Lys Leu Val Glu Ala Lys
        190                 195                 200

ATC AAT GAA CTT CAA GCA GCG GGG GCA ACG GAA AAG TCC ATT AAA TCG     736
Ile Asn Glu Leu Gln Ala Ala Gly Ala Thr Glu Lys Ser Ile Lys Ser
    205                 210                 215

ACA ATG AAG GAC ATG GGC ATC GAG AGG GCA AGA CAC TGG GGA TGG CCA     784
Thr Met Lys Asp Met Gly Ile Glu Arg Ala Arg His Trp Gly Trp Pro
220                 225                 230                 235

AAT GTG TAT GTA TTC ACC AAG GCA TTA GGG GAG ATG CTT TTG ATG CAA     832
Asn Val Tyr Val Phe Thr Lys Ala Leu Gly Glu Met Leu Leu Met Gln
                240                 245                 250

TAC AAA GGG GAC ATT CCG CTT ACT ATT ATT CGT CCC ACC ATC ATC ACC     880
Tyr Lys Gly Asp Ile Pro Leu Thr Ile Ile Arg Pro Thr Ile Ile Thr
            255                 260                 265
```

FIGURE 17C

```
AGC ACT TTT AAA GAG CCC TTT CCT GGT TGG GTT GAA GGT GTC AGG ACC      928
Ser Thr Phe Lys Glu Pro Phe Pro Gly Trp Val Glu Gly Val Arg Thr
        270                 275                 280

ATC GAT AAT GTA CCT GTA TAT TAT GGT AAA GGG AGA TTG AGG TGT ATG      976
Ile Asp Asn Val Pro Val Tyr Tyr Gly Lys Gly Arg Leu Arg Cys Met
    285                 290                 295

CTT TGC GGA CCC AGC ACA ATA ATT GAC CTG ATA CCG GCA GAT ATG GTC     1024
Leu Cys Gly Pro Ser Thr Ile Ile Asp Leu Ile Pro Ala Asp Met Val
300                 305                 310                 315

GTG AAT GCA ACG ATA GTA GCC ATG GTG GCG CAC GCA AAC CAA AGA TAC     1072
Val Asn Ala Thr Ile Val Ala Met Val Ala His Ala Asn Gln Arg Tyr
                320                 325                 330

GTA GAG CCG GTG ACA TAC CAT GTG GGA TCT TCA GCG GCG AAT CCA ATG     1120
Val Glu Pro Val Thr Tyr His Val Gly Ser Ser Ala Ala Asn Pro Met
            335                 340                 345

AAA CTG AGT GCA TTA CCA GAG ATG GCA CAC CGT TAC TTC ACC AAG AAT     1168
Lys Leu Ser Ala Leu Pro Glu Met Ala His Arg Tyr Phe Thr Lys Asn
        350                 355                 360
```

FIGURE 17D

```
CCA TGG ATC AAC CCG GAT CGC AAC CCA GTA CAT GTG GGT CGG GCT ATG    1216
Pro Trp Ile Asn Pro Asp Arg Asn Pro Val His Val Gly Arg Ala Met
    365                 370                 375

GTC TTC TCC TCC TTC TCC ACC TTC CAC CTT TAT CTC ACC CTT AAT TTC    1264
Val Phe Ser Ser Phe Ser Thr Phe His Leu Tyr Leu Thr Leu Asn Phe
380                 385                 390                 395

CTC CTT CCT TTG AAG GTA CTG GAG ATA GCA AAT ACA ATA TTC TGC CAA    1312
Leu Leu Pro Leu Lys Val Leu Glu Ile Ala Asn Thr Ile Phe Cys Gln
                400                 405                 410

TGG TTC AAG GGT AAG TAC ATG GAT CTT AAA AGG AAG ACG AGG TTG TTG    1360
Trp Phe Lys Gly Lys Tyr Met Asp Leu Lys Arg Lys Thr Arg Leu Leu
            415                 420                 425

TTG CGT TTA GTA GAC ATT TAT AAA CCC TAC CTC TTC TTC CAA GGC ATC    1408
Leu Arg Leu Val Asp Ile Tyr Lys Pro Tyr Leu Phe Phe Gln Gly Ile
        430                 435                 440

TTT GAT GAC ATG AAC ACT GAG AAG TTG CGG ATT GCT GCA AAA GAA AGC    1456
Phe Asp Asp Met Asn Thr Glu Lys Leu Arg Ile Ala Ala Lys Glu Ser
    445                 450                 455
```

FIGURE 17E

```
ATA GTT GAA GCT GAT ATG TTT TAC TTT GAT CCC AGG GCA ATT AAC TGG     1504
Ile Val Glu Ala Asp Met Phe Tyr Phe Asp Pro Arg Ala Ile Asn Trp
460                 465                 470                 475

GAA GAT TAC TTC TTG AAA ACT CAT TTC CCA GGN GTC GTA GAG CAC GTT     1552
Glu Asp Tyr Phe Leu Lys Thr His Phe Pro Gly Val Val Glu His Val
                480                 485                 490

CTT AAC TAAAAGTTAC GGTACGAAAA TGAGAAGATT GGAATGCATG CACCGAAAGN      1608
Leu Asn

NCAACATAAA AGACGTGGTT AAAGTCATGG TCAAAAAAGA AATAAAATGC AGTTAGGTTT 1668

GTGTTGCAGT TTTGATTCCT TGTATTGTTA CTTGTACTTT TGATCTTTTT CTTTTTTAAT 1728

GAAATTTCTC TCTTTGTTTT GTGAAAAAAA AAAAAAAAAA GAGCTCCTGC AGAAGCTT    1786
```

FIGURE 17F

```
GGAACTCCAT CCCTTCCTCC CTCACTCCTC TCTCTACA ATG AAG GCC AAA ACA ATC    56
                                          Met Lys Ala Lys Thr Ile
                                           1              5

ACA AAC CCG GAG ATC CAA GTC TCC ACG ACC ATG ACC ACC ACG ACC ACG     104
Thr Asn Pro Glu Ile Gln Val Ser Thr Thr Met Thr Thr Thr Thr Thr
             10                  15                  20

ACT ATG ACC GCC ACT CTC CCC AAC TTC AAG TCC TCC ATC AAC TTA CAC     152
Thr Met Thr Ala Thr Leu Pro Asn Phe Lys Ser Ser Ile Asn Leu His
         25                  30                  35

CAC GTC AAG CTC GGC TAC CAC TAC TTA ATC TCC AAT GCC CTC TTC CTC     200
His Val Lys Leu Gly Tyr His Tyr Leu Ile Ser Asn Ala Leu Phe Leu
     40                  45                  50

GTA TTC ATC CCC CTT TTG GGC CTC GCT TCG GCC CAT CTC TCC TCC TTC     248
Val Phe Ile Pro Leu Leu Gly Leu Ala Ser Ala His Leu Ser Ser Phe
55                  60                  65                  70
```

FIGURE 18A

```
TCG GCC CAT GAC TTG TCC CTG CTC TTC GAC CTC CTT CGC CGC AAC CTC      296
Ser Ala His Asp Leu Ser Leu Leu Phe Asp Leu Leu Arg Arg Asn Leu
                 75                  80                  85

CTC CCT GTT GTC GTT TGT TCT TTC CTC TTC GTT TTA TTA GCA ACC CTA      344
Leu Pro Val Val Val Cys Ser Phe Leu Phe Val Leu Leu Ala Thr Leu
             90                  95                 100

CAT TTC TTG ACC CGG CCC AGG AAT GTC TAC TTG GTG GAC TTT GGA TGC      392
His Phe Leu Thr Arg Pro Arg Asn Val Tyr Leu Val Asp Phe Gly Cys
        105                 110                 115

TAT AAG CCT CAA CCG AAC CTG ATG ACA TCC CAC GAG ATG TTC ATG GAC      440
Tyr Lys Pro Gln Pro Asn Leu Met Thr Ser His Glu Met Phe Met Asp
    120                 125                 130

CGG ACC TCC CGG GCC GGG TCG TTT TCT AAG GAG AAT ATT GAG TTT CAG      488
Arg Thr Ser Arg Ala Gly Ser Phe Ser Lys Glu Asn Ile Glu Phe Gln
135                 140                 145                 150

AGG AAG ATC TTG GAG AGG GCC GGT ATG GGT CGG GAA ACC TAT GTC CCC      536
Arg Lys Ile Leu Glu Arg Ala Gly Met Gly Arg Glu Thr Tyr Val Pro
                155                 160                 165
```

FIGURE 18B

```
GAA TCC GTC ACT AAG GTG CCC GCC GAG CCG AGC ATA GCA GCA GCC AGG     584
Glu Ser Val Thr Lys Val Pro Ala Glu Pro Ser Ile Ala Ala Ala Arg
            170                 175                 180

GCC GAG GCG GAG GAG GTG ATG TAC GGG GCG ATC GAC GAG GTG TTG GAG     632
Ala Glu Ala Glu Glu Val Met Tyr Gly Ala Ile Asp Glu Val Leu Glu
        185                 190                 195

AAG ACG GGG GTG AAG CCG AAG CAG ATA GGA ATA CTG GTG GTG ANC TGC     680
Lys Thr Gly Val Lys Pro Lys Gln Ile Gly Ile Leu Val Val Xxx Cys
    200                 205                 210

AGC TTG TTT AAC CCA ACG CCG TCG CTG TCA TCC ATG ATA GTT AAC CAT     728
Ser Leu Phe Asn Pro Thr Pro Ser Leu Ser Ser Met Ile Val Asn His
215                 220                 225                 230

TAC AAG CTN AGG GGT AAT ATA CTT AGC TAT AAT CTT GGT GGC ATG GGT     776
Tyr Lys Leu Arg Gly Asn Ile Leu Ser Tyr Asn Leu Gly Gly Met Gly
                235                 240                 245

TGC AGT GCT GGG CTC ATT TCC ATT GAT CTT GCC AAG GAC CTC CTA CAG     824
Cys Ser Ala Gly Leu Ile Ser Ile Asp Leu Ala Lys Asp Leu Leu Gln
            250                 255                 260
```

FIGURE 18C

```
GTT TAC CGT AAA AAC ACA TAT GTG TTA GTA GTG AGC ACG GAA AAC ATG     872
Val Tyr Arg Lys Asn Thr Tyr Val Leu Val Val Ser Thr Glu Asn Met
        265                 270                 275

ACC CTT AAT TGG TAC TGG GGC AAT GAC CGC TCC ATG CTT ATC ACC AAC     920
Thr Leu Asn Trp Tyr Trp Gly Asn Asp Arg Ser Met Leu Ile Thr Asn
    280                 285                 290

TGC CTA TTT CGC ATG GGT GGC GCT GCC ATC ATC CTC TCA AAC CGC TGG     968
Cys Leu Phe Arg Met Gly Gly Ala Ala Ile Ile Leu Ser Asn Arg Trp
295                 300                 305                 310

CGT GAT CGT CGC CGA TCC AAG TAC CAA CTC CTT CAT ACA GTA CGC ACC    1016
Arg Asp Arg Arg Arg Ser Lys Tyr Gln Leu Leu His Thr Val Arg Thr
                315                 320                 325

CAC AAG GGC GCT GAC GAC AAG TCC TAT AGA TGC GTC TTA CAA CAA GAA    1064
His Lys Gly Ala Asp Asp Lys Ser Tyr Arg Cys Val Leu Gln Gln Glu
            330                 335                 340

GAT GAA AAT AAC AAG GTA GGT GTT GCC TTA TCC AAG GAT CTG ATG GCA    1112
Asp Glu Asn Asn Lys Val Gly Val Ala Leu Ser Lys Asp Leu Met Ala
        345                 350                 355

GTT GCC GGT GAA GCC CTA AAG GCC AAC ATC ACG ACC CTT GGT CCC CTC    1160
Val Ala Gly Glu Ala Leu Lys Ala Asn Ile Thr Thr Leu Gly Pro Leu
    360                 365                 370
```

FIGURE 18D

```
GTG CTC CCC ATG TCA GAA CAA CTC CTC TTC TTT GCC ACC TTA GTG GCA    1208
Val Leu Pro Met Ser Glu Gln Leu Leu Phe Phe Ala Thr Leu Val Ala
375                 380                 385                 390

CGT AAG GTC TTC AAG ATG ACG AAC GTG AAG CCA TAC ATC CCA GAT TTC    1256
Arg Lys Val Phe Lys Met Thr Asn Val Lys Pro Tyr Ile Pro Asp Phe
                395                 400                 405

AAG TTG GCA GCG AAC GAC TTC TGC ATC CAT GCA GGA GGC AAA GCA GTG    1304
Lys Leu Ala Ala Asn Asp Phe Cys Ile His Ala Gly Gly Lys Ala Val
            410                 415                 420

TTG GAT GAG CTC GAG AAG AAC TTG GAG TTG ACG CCA TGG CAC CTT GAA    1352
Leu Asp Glu Leu Glu Lys Asn Leu Glu Leu Thr Pro Trp His Leu Glu
        425                 430                 435

CCC TCG AGG ATG ACA CTG TAT AGG TTT GGG AAC ACA TCG AGT AGC TCA    1400
Pro Ser Arg Met Thr Leu Tyr Arg Phe Gly Asn Thr Ser Ser Ser Ser
    440                 445                 450

TTA TGG TAC GAG TTG GCA TAC GCT GAA GCA AAA GGG AGG ATC CGT AAG    1448
Leu Trp Tyr Glu Leu Ala Tyr Ala Glu Ala Lys Gly Arg Ile Arg Lys
455                 460                 465                 470
```

FIGURE 18E

```
GGT GAT CGA ACT TGG ATG ATT GGA TTT GGT TCA GGT TTC AAG TGT AAC    1496
Gly Asp Arg Thr Trp Met Ile Gly Phe Gly Ser Gly Phe Lys Cys Asn
                475                 480                 485

AGT GTT GTG TGG AGG GCT TTG AGG AGT GTC AAT CCG GCT AGA GAG AAG    1544
Ser Val Val Trp Arg Ala Leu Arg Ser Val Asn Pro Ala Arg Glu Lys
            490                 495                 500

AAT CCT TGG ATG GAT GAA ATT GAG AAG TTC CCT GTC CAT GTG CCT AAA    1592
Asn Pro Trp Met Asp Glu Ile Glu Lys Phe Pro Val His Val Pro Lys
        505                 510                 515

ATC GCA CCT ATC GCT TCG TAGAACTGCT AGGATGTGAT TAGTAATGAA           1640
Ile Ala Pro Ile Ala Ser
    520

AAATGTGTAT TATGTTAGTG ATGTAGAAAA AGAAACTTTA GTTGATGGGT GAGAACATGT 1700

CTCATTGAGA ATAACGTGTG CATCGTTGTG TTG                               1733
```

FIGURE 18F

```
TCTAGAATTC TCTAATTACG TCTGTTTGTT CTATTTTTTA TATGATATCA AATATTCGTC ATAAATATAT    70
GGTTTAAGAT GCCAAAAAAT TATTTACTTG GTGAATATAA TACGTTAAAT ATTAGAAATA CATCATTTAG   140
TTAAATAAAT AACCAAAAAC CAAAAATTCA TATCCGCGCT GGCGCGCGGT CAGGGTCTCG TTAGTTTTAA   210
AATCAATGCA GTTTACAATT AATTTCCAGC TGAAAATAAG TATAATTTGT ATTGAAATTA TAAAGTGACA   280
TTTTTTGTGT AACAAATATT TTGTGTAACA AGAATTAAAA AAAAAAACAG AAAATACTCA GCTTTTTTAA   350
TAATAAAAAA AATTAATTGA GTTAGAAAAT TGTTGTACCA ATAACAAAAG ATTTATATGG AATTATAAAA   420
TCAACACACC AATAACACAA GACTTTTTAA AAATTTAAGA ATAATATAAG CAATAACAAT AGAATCTTCA   490
AATTCTTCAA ATCCTTAAAA ATCAATCTCC CACTATTAAT CCCCCTTAGT TTTAGTTGGT AATGGCAACG   560
TTTGTTGACT ACCGTATTGT AACTTTTGTC AAATTGTCAT AAATACGTGT CAAACTCTGG TAAAAAATTA   630
GTCTGCTACA TCTGTCTTTT ATTTATAAAA CACAGCTGTT AATCAGAATT TGGTTTATTA AATCAACAAC   700
CTGCACGAAA CTTGTGTGAG CATATTTTGT CTGTTTCTGG TTCATGACCT TCTTCCGCAT GATGGCCAAG   770
TGTAATGGCC ACTTGCAAGA GCGTTTCTTC AACGAGATAA GTCGAACAAA TATTTGTCCG TTACGACCAC   840
ATATAAAATC TCCCCATCTC TATATATAAT ACCAGCATTC ACCATCATGA ATACCTCAAA TCCCAATCTC   910
ACAAATACTT CAATAAAAAG ACCAAAAAAA ATTAAAGCAA AGAAAAGCCT TCTTGTGCAC AAAAAAAAAA   980
```

Figure 19A

```
GAAGCCTTCT AGGTTTTCAC GAC ATG AAG TTC ACT ACT CTA ATG GTC ATC ACA TTG         1036
                          MET Lys Phe Thr Thr Leu MET Val Ile Thr Leu

GTG ATA ATC GCC ATC TCG TCT CCT GTT CCA ATT AGA GCA ACC ACG GTT GAA AGT      1090
Val Ile Ile Ala Ile Ser Ser Pro Val Pro Ile Arg Ala Thr Thr Val Glu Ser

TTC GGA GAA GTG GCA CAA TCG TGT GTT GTG ACA GAA CTC GCC CCA TGC TTA CCA      1144
Phe Gly Glu Val Ala Gln Ser Cys Val Val Thr Glu Leu Ala Pro Cys Leu Pro

GCA ATG ACC ACG GCA GGA GAC CCG ACT ACA GAA TGC TGC GAC AAA CTG GTA GAG      1198
Ala MET Thr Thr Ala Gly Asp Pro Thr Thr Glu Cys Cys Asp Lys Leu Val Glu

CAG AAA CCA TGT CTT TGT GGT TAT ATT CGA AAC CCA GCC TAT AGT ATG TAT GTT      1252
Gln Lys Pro Cys Leu Cys Gly Tyr Ile Arg Asn Pro Ala Tyr Ser MET Tyr Val

ACT TCT CCA AAC GGT CGC AAA GTC TTA GAT TTT TGT AAG GTT CCT TTT CCT AGT      1306
Thr Ser Pro Asn Gly Arg Lys Val Leu Asp Phe Cys Lys Val Pro Phe Pro Ser

TGT TAAATCTCTC AAGACATTGC TAAGAAAAAT ATTATTAAAA ATAAAAGAAT CAAACTAGAT         1369
Cys

CTGATGTAAC AATGAATCAT CATGTTATGG TTGAAGCTTA TATGCTGAAG TGTTTGATTT TATATATGTG  1439

TGTGTGTGTG TCCTGCTCAA TTTTTGAAAC ACACACGTTT CTCCTGATTT GGATTTAAAT TATATTTTGA  1509

GTTAAAAAAA AGAAAAAGAT GGAATGCTAT TTATACAAGT TGATGAAAAA GTGGAAGTAC AATTTAGATA  1579
```

Figure 19B

```
TCTCCTACAC TTAAAGAATG AAACAATAAT AGACTTACGA AACAAATGAA AAATACATAA ATTGTCGACA  1649
ATCAACGTCC GATGACGAGT TTATTATTAA AAATTTGTGT GAAGGACTAG CAGTTCAACC AAATGATATT  1719
GAACATATAC ATCAACAAAT ATGATAATCA TAAAAGAGAG AATGGGGGGG GGGTGTCGTT TACCAGAAAC  1789
CTCTTTTTCT CAGCTCGCTA AAACCCTACC ACTAGAGACC TAGCTCTGAC CGTCGGCTCA TCGGTGCCGG  1859
AGGTGTAACC TTTCTTTCCC ATGACCCGAA ACCTCTCTTT CCCAACTCAC GAAAACCCTA CAATCAAAAA  1929
CCTAGCTCCG ACCGTCGGCT CATCGGTGCC GAAGGTGTAA CCTTTCTCTC CCATCATAGT TTCTCGTAAA  1999
TGAAAGCTAA TTGGGCAATC GATTTTTTAA TGTTTAAACC ATGCCAAGCC ATTTCTTATA GGACAATTGT  2069
CAATAATAGC ATCTTTTGAG TTTTGTCTCA AAAGTGACAC TAGAAGAAAA AAGTCACAAA AATGACATTC  2139
ATTAAAAAGT AAAATATCCC TAATACCTTT GGTTTAAATT AAATAAGTAA ACAAAAATAA ATAAAAACAA  2209
ATAAAATAAA AATAAAAAAT GAAAAAAAGA AATTTTTTTA TAGTTTCAGA TTATATGTTT TCAGATTCGA  2279
AATTTTTTAA ATTCCCTTTT TTAAATTTTC TTTTTTGAAA TTTTTTTTTT TGAAATTTTT TGAAACTGTT  2349
TTTAAAATTT TTATTTTTAA TTTTTTAGTA TTTATTTTTT ATTTTATAAA ATTTTAAACG CTAATTCCAA  2419
AACTCCCCCC CCCCCCCCCC CCCCAATTCT CTCCTAGTCT TTTTCTCTTT CTTATATTTG GGCTTCTATC  2489
TTCTCTTTTT TTTTCAGGCC CAAAGTATCA TGTGTAACAA CCGGTGTTCA AAAACGCGCC CGCCTGGCCG  2559
```

Figure 19C

```
TTTACTCGCC CGATTAAATG ATGATCGGAA GGCTGCCATG GCGAGGCGGA GGTAATCAGT GGTTCTAGGC  2629
GCTGAAACTA GAAAACCTTC AAAAATCGAA ATTTTAAGAG CTAAATCGGT GTTTATCTCA TGAATCTATT  2699
ATATTTAGTT GAAACTCACA AGAATCGGTT GTAAAAACTA TGAAATCGTG CAAAAAAAAT GAAGAACAAA  2769
ATATTCTCAG ATCTGGAAAA CACAGAGAAG AGGTTGAAGA TGAGGGTAAA ATCGTATTTT GTCATTCATT  2839
AAACTAAAAT CAAAAAAAAA TGATGCAAAA TTCAATGATA ATAACTCGAA CTCGCAACCA TATGCATCTT  2909
TAGACTGCGA CACGGACCAC TAGACTAAGC AATTTTAATG TTTATTCATC ACAGACCTAA TATATGTCTA  2979
AAACTAGGCG CCGAGTACGC CCCGCTTAAT CCCGAGTTTT TGTTAGCTCG CTAGACCCAG GGTCACCGCC  3049
CGACTAACGA GTAGCGTAAT TCTGAACTGG GGTAACAACA TAGAGAACAT CGCCGACCCT TCCCTGCCGA  3119
TGATGCCGCC TCCGATGAAC TTCCTGTAAC GCCTTCAGTT TCCATTGATT TTCCCCTTTA ATCTGATCAG  3189
TTCCATGTTT TATCCAACTC ATCCCACTCC GTAGCATTTA ATCGATCTCA TCATTTACAT ACATAACCAG  3259
TAGGAGGTCT CATATAAATT TGAACGTTTC CAGCGATGAA CAGTGCCAAT CTCTGCGAAA TCCATTTCTC  3329
TAAGCTCAGG GCTGGCGGCT GCAGCCCGGG GATCCACTAG TTCTAGGCGG CCGCACCGCG GTGGAGCTCC  3399
AATTCGCCCT ATAGTGAGTC GTATTACGCG CGCTCACTGG C                                 3440
```

Figure 19D

```
     XhoI
     |
  1  CTCGAGAGCTGAAGGATTTTTTGTTAGAGATTCAACGACAGATGGACCCTTCCTCCACTAGGCAACTGC   69
     2

 70  AAGAACCTAACAATGCAAATATCACTCCTCCTCAGCCTTCAAGGAGCGTTAATAGGACTGGAACAAGCG  138

                                    BglII
                                    |
139  GTCAAGTGAGTAAATTTTCCTTCCAAGATAGATCTCTATGGTTCGGTTCATGAAGTTTGTGGTTTAATT  207
                                    169

208  GTGTAGCAACAGGATAGTGCAAGTGAGAATAGAGTTCGACCTCATCTACCTACCCCGGAACCTCTGAAT  276

277  GTATCCCCATTGAAGAAGAAGAGGGCAAATCCTGCACCCAGAAGGATAAAGAAATTTTGGACGCCTGAA  345

346  GAAGTGGCAGTTCTGAGGGAAGGAGTAAAAGAGTATGTCTACTACTACTACTCTATAATCAAGTTTCAA  414

415  GAAGCTGAGCTTGGCTCTCACTTTATATGTTTGATGTTGTTGTGCAGGTATGGTAAATCATGGAAAGAG  483

484  ATAAAGAATGCAAACCCTGAAGTATTGGCAGAGAGGACTGAGGTGAGAGAGCATGTCACTTTTGTGTTA  552

553  CTCATCTGAATTATCTTATATGCGAATTGTAAGTGGTACTAAAAGGTTTGTAACTTTTGGTAGGTGGAT  621

622  TTGAAGGATAAATGGAGGAACTTGCTTCGGTAGCGGTAACAAGTTTTATATTGCTATGAAGTTTTTTTG  690

691  CCTGCGTGACGTATCAGCAGCTGTGGAGAAGATGGTATTAGAAAGGGTCTTTTCACATTTTGTGTTGTG  759
```

Figure 20A

```
760  ACAAATATTAATTCGGCCGGTATGGTTTGGTTAAGACTTGTTGAGAGACGTGTGGGGTTTTTTGATGTA   828

829  TAATTAGTCTGTGTTTAGAACGAAACAAGACTTGTTGCGTATGCTTTTTTTAACTTGAGGGGGTTTGTT   897

                                                BglII
                                                |
898  GTTGTTAGTTAGGAACTTGACTTTGTCTCTTTCTCTCAAGATCTGATTGGTAAGGTCTGGGTGGTAGTA   966
                                                937

967  CTGTTTGGTTTAATTTGTTTTGACTATTGAGTCACTGTGGCCCATTGACTTTAAATTAGGCTGGTATAT  1035

1036 TTTTTGGTTTAAAACCGGTCTGAGATAGTGCAATTTCGATTCAGTCAATTTTAAATTCTTCAAGGTAAT  1104

1105 GGGCTGAATACTTGTATAGTTTTAAGACTTAACAGGCCTTAAAAGGCCCATGTTATCATAAAACGTCAT  1173

                     HindIII
                     |
1174 TGTTTAGAGTGCACCAAGCTTATAAAATGTAGCCAGGCCTTAAAAGACTTAACAGGCCTTAAAAGACTT  1242
                     1190

1243 AACATTCCTTAAAAGGCCCATGTTATCATAAAACGTCATCGTTTTGAGTGCACCAAGCTAAATGTAGCC  1311

1312 AGGCCTTAAAAGACTTAACAGGCCTTAAAAGGCCCATGTTATCATAAAACGCCGTCGTTTTGAGTGCAC  1380
```

Figure 20B

```
      HindIII
      |
1381 CAAGCTTATAAATGTAGCCAGCTACCTCGGGACATCACGCTCTTTGTACACTCCGCCATCTCTCTCTCT 1449
      1383

     XhoI   BglII                            SalI
     |      |                                |
1450 CTCGAGCAGATCTCTCTCGGGAATATCGACAATGTCGACCACTTTCTGCTCTTCCGTCTCCATGCAAGC 1518
     1451   1458                             1484

1519 CACTTCTCTGGTAATCTCATCTCCTTCTTGTGTTCCCAGATCGCTCTGATCATACTTTCTTTTAGATCA 1587

1588 TTTGCCTCTGATCTGTTGCTTGATGTTTGTTAACTCTCCACGCATGTTTGATTATGTTGAGAATTAGAA 1656

1657 AAAAAATGTTAGCTTTACGAATCTTTAGTGATCATTTCAATTGGATTTGCAATCTTGTGTGACATTTGA 1725

1726 GGCTTGTGTAGATTTCGATCTGTATTCATTTTGAATCACAGCTATAATAGTCATTTGAGTAGTAGTGTT 1794

1795 TTTAAATGAACATGTTTTGTTGTATTGATGGAACAAACAGGCAGCAACAACGAGGATTAGTTTCCAGAA 1863

1864 GCCAGCTTTGGTTTCAACGACTAATCTCTCCTTCAACCTCCGCCGTTCAATCCCCACTCGTTTCTCAAT 1932

1933 CTCCTGCGCGGTATGTTCTCATTCTCAGCATTTATTTCGAGCTTGCTTGTCATGGTACTCTCTCTAATT 2001

2002 GTCTATTTGGTTTATTAGGCCAAACCAGAGACGGTTGAGAAAGTGTCTAAGATAGTTAAGAAGCAGCTA 2070
```

Figure 20C

```
2071 TCACTCAAAGACGACCAAAAGGTCGTTGCGGAGACCAAGTTTGCTGATCTTGGAGCAGATTCTCTCGAC 2139

2140 ACTGTAAGTCATCAATCATTCTCTTATGTGAATAAAGAGAACTTGAAGAGTTTGTTTTTAACATATTAA 2208

                                                                EcoRV
                                                                |
2209 CTGAGTGTTTTGCATGCAGGTTGAGATAGTGATGGGTTTAGAGGAAGAGTTTGATATCGAAATGGCTGA 2277
                                                                2264

                                                                  SstI
                                                                  |
2278 AGAGAAAGCTCAGAAGATTGCTACTGTGGAGGAAGCTGCTGAACTCATTGAAGAGCTCGTTCAACTTAA 2346
                                                                  2335

2347 GAAGTAATTTTAGTATTAAGAGCAGCCAAGGCTTTGTTGGGTTTGTTGTTTTCATAATCTTCCTGTCAT 2415

2416 TTTCTTTTTCTTTAATGTGTCAAGCGACTCTGTTGGTTTAAAGTAGTATCTGTTTGCCATGGATCTCTC 2484

             SalI                         HindIII
             |                            |
2485 TCTATTTGTCGACTGAAAACTTTTGGTTTACACATGAAAGCTTGTTCTTGTTCTTTCTTAAATCGAAAT 2553
             2493                         2523

2554 GCCAAATGCGAGATTAGGGAATCTTGTATTAACACATACATAAGTCAAAGAGTAGGCCCTAAGATGACA 2622

2623 ATTTATAAACAATCCTATTCACATTGTATATACAGGTTATGATTATTCCCAATCAGCGTCAAAGAATCC 2691
```

Figure 20D

```
2692 AGCATCTTTCATCTCTGAATAGTAGACATTCTCCAAGTTCACATCTTCCTCCTGCACCAAAAACCAGTA 2760
2761 CTAAATCATGAACATTGCAATAATCACATGCCTAGGCGAGAGTTTTGGTGATGTGGTGTTAGTGATAGT 2829
2830 GATACTGATGGTGCTAGAGCGGTTAAGAAGGATTAACCTGGAAGAAGTCTGCAAGGAAAGTAACATAGA 2898
2899 GAAGAGGAAGATAGGAGTGGTAACAAACACTTGTGATCCCATACAGCCTCCCAGCATTTTTCAAATGTT 2967
2968 ATTTCCTTACATAAAGAAACAAGAGAAGTCTGACTAGATGATATTTATATAGGATAAGTGTTTTACCAT 3036
3037 AAGCCAAAGTGAGCGCCGTTTGCAAGAGCTAACCAGACAGTACACGTTTGGCATATATCTCATCAACAT 3105
3106 GATCTGAAAAGTAACATATCACAGTTAATGAACACAATGGTTACCTTGAGAAGCAAATCAAGACCTATA 3174
3175 ACAAGCCCAGAGATGAGGAAAGTCCGTGTCAACGCTTCACCGCCATTCGCGTAGTTTCCTTGGAAGACA 3243
3244 AAGGCCACCAACCAAACTTACTTCCAGAAACAACACTCCAAATGTTGTCAACAAAGTCAATAGATTCCA 3312
3313 AACTACTTCGTTACAGGGTTGTATAGATAATATAATAGAATAGTGGGAAGATAGTATAAATAAAATAAA 3381
3382 TAAAAGATCCTATCGGTAAATAGTTTATAATATCGGGGGCGTATATAAAGTATAAAAGAAACTCTTCTC 3450
3451 CAATCCGACCGTTGAAAATCACTCTCAATCTCTGGCGTAACGACCGGATCGTTCGCGCGTAATTTTCGC 3519
3520 TGCTATAAATAGAAACTTTCCTCTTCTGTTTCTCGATCAAAATTTTTTTTGGAAAAATTAAGTTTGAA 3588
```

Figure 20E

```
3589 TCTATCGTAGATGCTGTGACAAAAAAAAATTGTTTTATCGAAGATGAGAAACATGAGGCCTGTTCATGC 3657

                         BamHI
                         |
3658 AAGGAACCAGACCACGGATCCATCTTCGCCGATGATGACGTCTCCTCTGATGAATCGTCACGCACGGAC 3726
                         3674

       BamHI
       |
3727 AGGATCCAACGCTGGACCAGCATCTAACGCCAAGAAAGCACAGACGAAAGCAGCAGCTCAGAGACTCGC 3795
       3729

3796 GGCTGTGATGTCGAACCAAACAGGCGACGATGAAGACAGTGATGATGACCTTTCCTTTGACTACAACGC 3864

                                         BglII
                                         |
3865 TGTCGGAAGCATTGGTCTCGCTGCCGGAAGATCT 3898
                                         3894
```

Figure 20F

```
Lambda CGN1-2

NCG-186 Linear          LENGTH = 4325

                                                  SduI
     XhoI                                       NlaIV
     AvaI                                          HgiJII     HindIII
     |                                          |  |          |
   1 CTCGAGGCAGTCACTAACATGAAGTTTGACGAGGAGCCCAACTATGGGAAGCTTATTTCTCTTTTCGAT   69
     2                                             39         50
                                                36

                              XbaI                      SacI
                              |                         |
  70 ACTCTAATTGAGCCGTGCGCTCTATCTAGACCAATTAGAATTGATGGAGCTCTAAAGGTTGCTGGCTGT  138
                              95                        121

               NdeI                         SspI                     NdeI
               |                            |                        |
 139 TTTCTTGTTCATATGATTAACTTCTAAACTTGTGTATAAATATTCTCTGAAAGTGCTTCTTTTGGCATA  207
               150                          180                      206

                                          Ksp632I
                                          |
 208 TGTAGGTTGGGCAAAAACGAGGAAGATTGCTTCTCAATTTGGAAGAGGATGAACAGCCGAAGAAGAAAA  276
                                          245
```

Figure 21A

```
             Cfr10I
         BbvII
         |   |
553 TGAGTTGTCACCGGTCTTCCTACACAAGGTAATAATCAGTTGAAGCAATTAAGAATCAATTTGATTTGT  621
         560
             563

622 AGTAAACTAAGAAGAACTTACCTTATGTTTTCCCCGCAGGACTGGATTATGGAACAATGGGAAAAGAAC  690

                                                    SacI
                                                    |
691 TACTATATAAGCTCCATAGCTGGTTCAGATAACGGGAGCTCTTTAGTTGTTATGTCAAAAGGTTAGTGT  759
                                                    731

                              BbvII
                              |
760 TTAGTGAATAATAAACTTATACCACAAAGTCTTCATTGACTTATTTATATACTTGTTGTGAATTGCTAG  828
                              782

829 GAACTACTTATTCTCAGCAGTCATACAAAGTGAGTGACTCATTTCCGTTCAAGTGGATAAATAAGAAAT  897

898 GGAAAGAAGATTTTCATGTAACCTCCATGACAACTGCTGGTAATCGTTGGGGTGTGGTAATGTCGAGGA  966

                  BclI
                  |
967 ACTCTGGCTTCTCTGATCAGGTAGGTTTTTGTCTCTTATTGTCTGGTGTTTTTATTTTCCCCTGATAGT 1035
                  981
```

Figure 21C

```
1036 CTAATATGATAAACTCTGCGTTGTGAAAGGTGGTGGAGCTTGACTTTTTGTACCCAAGCGATGGGATAC 1104

1105 ATAGGAGGTGGGAGAATGGGTATAGAATAACATCAATGGCAGCAACTGCGGATCAAGCAGCTTTCATAT 1173

      Tth111II                                                             ScaI
      |                                                                    |
1174 TAAGCATACCAAAGCGTAAGATGGTGGATGAAACTCAAGAGACTCTCCGCACCACCGCCTTTCCAAGTA 1242
      1175                                                                 1242

                                                 XhoII
                                                 |
1243 CTCATGTCAAGGTTGGTTTCTTTAGCTTTGAACACAGATTTGGATCTTTTTGTTTTGTTTCCATATACT 1311
                                                 1285

1312 TAGGACCTGAGAGCTTTTGGTTGATTTTTTTTCAGGACAAATGGGCGAAGAATCTGTACATTGCATCA 1380

                                          AflII
                                          |
1381 ATATGCTATGGCAGGACAGTGTGCTGATACACACTTAAGCATCATGTGGAAAGCCAAAGACAATTGGAG 1449
                                          1415

1450 CGAGACTCAGGGTCGTCATAATACCAATCAAAGACGTAAAACCAGACGCAACCTCTTTGGTTGAATGTA 1518

                                                                           SspI
                                                                           |
1519 ATGAAAGGGATGTGTCTTGGTATGTATGTACGAATAACAAAAGAGAAGATGGAATTAGTAGTAGAAATA 1587
                                                                           1587
```

Figure 21D

```
                                                                  EcoRV
                                                                  |
1588 TTTGGGAGCTTTTTAAGCCCTTCAAGTGTGCTTTTTATCTTATTGATATCATCCATTTGCGTTGTTTAA 1656
                                                                  1635

            XbaI
            |
1657 TGCGTCTCTAGATATGTTCCTATATCTTTCTCAGTGTCTGATAAGTGAAATGTGAGAAAACCATACCAA 1725
            1664

             SspI
             |
1726 ACCAAAATATTCAAATCTTATTTTTAATAATGTTGAATCACTCGGAGTTGCCACCTTCTGTGCCAATTG 1794
             1734                                                   1789

                                                                    EcoRI
                                                                    |
1795 TGCTGAATCTATCACACTAGAAAAAAACATTTCTTCAAGGTAATGACTTGTGGACTATGTTCTGAATTC 1863
                                                                    1859

                                                          Eco57I
                                                          |
1864 TCATTAAGTTTTTATTTTCTGAAGTTTAAGTTTTTACCTTCTGTTTTGAAATATATCGTTCATAAGATG 1932
                                                          1904
```

Figure 21E

```
                                  SalI
                                    HindII                          NaeI
           AccI                    AccI                           Cfr10I
           |                       |||                            |  |
2209 AATGCCTCCGTCTACAGGACGGTTGTGGAAGTCGACGAAGATGATGCCACAAATCCAGCCGGCCCATTT 2277
     AsnAlaSerValTyrArgThrValValGluValAspGluAspAspAlaThrAsnProAlaGlyProPhe
           2220                     2241                          2267
                                     2242                           2269
                                  2240

                                                              Tth111II
                                                              HindIII          NlaIV
                                                              |                |
2278 AGGATTCCAAAATGTAGGAAGGAGTTTCAGCAAGCACAACACCTGAAAGCTTGCCAACAATGGCTCCAC 2346
     ArgIleProLysCysArgLysGluPheGlnGlnAlaGlnHisLeuLysAlaCysGlnGlnTrpLeuHis
                                                              2325             2342

                Tth111II                NlaIV                                BbvII
                |                       |                                    |
2347 AAGCAGGCAATGCAGTCCGGTAGTGGTCCAAGCTGGACCCTCGATGGTGAGTTTGATTTTGAAGACGAC 2415
     LysGlnAlaMETGlnSerGlySerGlyProSerTrpThrLeuAspGlyGluPheAspPheGluAspAsp
                2363                    2384                                 2415

                    NlaIV                                                 SacI
                      ApaI  GsuI HaeI  NspBII                               Ksp632
                    | |     |    |     |                                  |  |
2416 GTGGAGAACCAACAACAGGGCCCGCAGCAGAGGCCACCGCTGCTCCAGCAGTGCTGCAACGAGCTCCAC 2484
     ValGluAsnGlnGlnGlnGlyProGlnGlnArgProProLeuLeuGlnGlnCysCysAsnGluLeuHis
                      2438  2444 2449  2455                               2481
                    2436                                                     2484
```

Figure 21G

```
2485 CAGGAAGAGCCACTTTGCGTTTGCCCAACCTTGAAAGGAGCATCCAAAGCCGTTAAACAACAGATTCGA 2553
     GlnGluGluProLeuCysValCysProThrLeuLysGlyAlaSerLysAlaValLysGlnGlnIleArg

2554 CAACAACAGGGACAACAAATGCAGGGACAGCAGATGCAGCAAGTGATTAGCCGTATCTACCAGACCGCT 2622
     GlnGlnGlnGlyGlnGlnMETGlnGlyGlnGlnMETGlnGlnValIleSerArgIleTyrGlnThrAla

                                                                    SecI
                                                                BbvII
                                                                |   |
2623 ACGCACTTACCTAGAGCTTGCAACATCAGGCAAGTTAGCATTTGCCCCTTCCAGAAGACCATGCCTGGG 2691
     ThrHisLeuProArgAlaCysAsnIleArgGlnValSerIleCysProPheGlnLysThrMETProGly
                                                                2684
                                                                    2687

     NlaIV                                                     SecI
       HgiJII                              XhoI                DsaI
       ApaI                                AvaI         AccI
     | |                                   |            |   |
2692 CCCGGCTTCTACTAGATTCCAAACGAATATCCTCGAGAGTGTGTATACCACGGTGATATGAGTGTGGTT 2760
     ProGlyPheTyr
       2694                                2724         2736
     2692                                                   2740

                   HpaI
                   HindII
                   |
2761 GTTGATGTATGTTAACACTACATAGTCATGGTGTGTGTTCCATAAATAATGTACTAATGTAATAAGAAC 2829
                   2774
```

Figure 21H

```
                                        BbvII                                                  Tth111
                                        |                                                      |
3106 TTATGCAAGTGTTCTTTTATTTGGTGAAGACTCTTTAGAAGCAAAGAACGACAAGCAGTAATAAAAAAA 3174
                                        3139                                                   3174

                                                                                     VspI
                                                                                     |
3175 ACAAAGTTCAGTTTTAAGATTTGTTATTGACTTATTGTCATTTGAAAAATATAGTATGATATTAATATA 3243
                                                                                     3237

         Tth111II                                    VspI
         |                                           |
3244 GTTTTATTTATATAATGCTTGTCTATTCAAGATTTGAGAACATTAATATGATACTGTCCACATATCCAA 3312

         3250                                        3287

                                    NdeI           Tth111II
                                    |              |
3313 TATATTAAGTTTCATTTCTGTTCAAACATATGATAAGATGGTCAAATGATTATGAGTTTTGTTATTTAC 3381
                                    3341           3352

                             Eco57I                                      Eco57I
                             |                                           |
3382 CTGAAGAAAAGATAAGTGAGCTTCGAGTTTCTGAAGGGTACGTGATCTTCATTTCTTGGCTAAAAGCGA 3450
                             3404                                        3434

3451 ATATGACATCACCTAGAGAAAGCCGATAATAGTAAACTCTGTTCTTGGTTTTTGGTTTAATCAAACCGA 3519
```

Figure 21J

```
      Cfr10I                                          Tth111II
      |                                               NdeI
      |                                               ||
3520 ACCGGTAGCTGAGTGTCAAGTCAGCAAACATCGCAAACCATATGTCAATTCGTTAGATTCCCGGTTTAA 3588
      3521                                            3560
                                                       3561

             Cfr10I
             |
3589 GTTGTAAACCGGTATTTCATTTGGTGAAAACCCTAGAAGCCAGCCANCCTTTTTAATCTAATTTTTGCA 3657
             3597

                                                                   NlaIV
                                                                   HindII
                                                                 HgiCI
                                                                  BspHI
                                                                 |||
3658 AACGAGAAGTCACCACACCTCTCCACTAAAACCCTGAACCTTACTGAGAGAAGCAGAGNCANNAAAGAA 3726
                                                                  3717
                                                                 3716
                                                                   3718

                  Eco31I          PmaCI                    Ksp632I
                  |               |                        |
3727 CAAATAAAACCCGAAGATGAGACCACCACGTGCGGCGGGACGTTCAGGGGACGGGGAGGAAGAGAATGR 3795
                  3740            3756                     3781

3796 CGGCGG5MNTTTGGTGGCGGCGGCGGACGTTTTGGTGGCGGCGGTGGACGTTTTGGTGGCGGCGGTGGA 3864
```

Figure 21K

```
                EcoRV
                |
3865 CCTTTGGTGGTGGATATCGTGACGAAGGACCTCCCAGTGAAGTCATTGGTTCGTTTACTCTTTTCTTAG 3933
                3880

                                                HindIII
                                                   AflII
                                                |  |
3934 TCGAATCTTATTCTTGCTCTGCTCGTTGTTTTACCGATAAAGCTTAAGACTTTATTGATAAAGTTCTCA 4002
                                                   3977
                                                3974

4003 GCTTTGAATGTGAATGAACTGTTTCCTGCTTATTAGTGTTCCTTTGTTTTGAGTTGAATCACTGTCTTA 4071

4072 GCACTTTTGTTAGATTCATCTTTGTGTTTAAGTTAAAAGGTAGAAACTTTGTGACTTGTCTCCGTTATG 4140

         HpaI
         HindII                                Tth111II
         |                                     |
4141 ACAAGGTTAACTTTGTTGGTTATAACAGAAGTTGCGACCTTTCTCCATGCTTGTGAGGGTGATGCTGTG 4209
         4149                                  4179

                      XhoII
                      |
4210 GACCAAGCTCTCTCAGGCGAAGATCCCTTACTTCAATGCCCCAATCTACTTGGAAAACAAGACACAGAT 4278
                      4231
```

Figure 21L

SEQUENCE LISTING

```
<160> NUMBER OF SEQ ID NOS: 48

<210> SEQ ID NO 1
<211> LENGTH: 1533
<212> TYPE: DNA
<213> ORGANISM: Carthamus tinctorius

<400> SEQUENCE: 1

gctcacttgt gtggtggagg agaaaaacag aactcacaaa aagctttgcg actgccaaga     60

acaacaacaa caacaagatc aagaagaaga agaagaagat caaaaatggc tcttcgaatc    120

actccagtga ccttgcaatc ggagagatat cgttcgtttt cgtttcctaa gaaggctaat    180

ctcagatctc ccaaattcgc catggcctcc accctcggat catccacacc gaaggttgac    240
```

-continued

```
aatgccaaga agccttttca acctccacga gaggttcatg ttcaggtgac gcactccatg    300
ccaccacaga agatagagat tttcaaatcc atcgagggtt gggctgagca gaacatattg    360
gttcacctaa agccagtgga gaaatgttgg caagcacagg atttcttgcc ggaccctgca    420
tctgaaggat ttgatgaaca agtcaaggaa ctaagggcaa gagcaaagga gattcctgat    480
gattactttg ttgttttggt tggagatatg attacagagg aagccctacc tacttaccaa    540
acaatgctta ataccctaga tggtgtacgt gatgagactg ggctagcct tacgccttgg    600
gctgtctgga ctagggcttg gacagctgaa gagaacaggc atggcgatct tctccacacc    660
tatctctacc tttctgggcg ggtagacatg aggcagatac agaagacaat tcagtatctc    720
attgggtcag gaatggatcc tcgtaccgaa aacagcccct accttgggtt catctacaca    780
tcgtttcaag agcgtgccac atttgtttct cacggaaaca ccgccaggca tgcaaaggat    840
catggggacg tgaaactggc gcaaatttgt ggtacaatcg cgtctgacga aaagcgtcac    900
gagaccgctt atacaaagat agtcgaaaag ctattcgaga tcgatcctga tggcaccgtt    960
cttgcttttg ccgacatgat gaggaaaaag atctcgatgc ccgcacactt gatgtacgat   1020
gggcgtgatg acaacctctt cgaacatttc tcggcggttg cccaaagact cggcgtctac   1080
accgccaaag actacgccga catactggaa tttctggtcg ggcggtggaa agtggcggat   1140
ttgaccggcc tatctggtga agggcgtaaa gcgcaagatt atgtttgcgg gttgccacca   1200
agaatcagaa ggctggagga gagagctcaa gggcgagcaa aggaaggacc tgttgttcca   1260
ttcagctgga ttttcgatag acaggtgaag ctgtgaagaa aaaaaaaacg agcagtgagt   1320
tcggtttctg ttggcttatt gggtagaggt taaaacctat tttagatgtc tgtttcgtgt   1380
aatgtggttt tttttcttct aatcttgaat ctggtattgt gtcgttgagt tcgcgtgtgt   1440
gtaaacttgt gtggctgtgg acatattata gaactcgtta tgccaatttt gatgacggtg   1500
gttatcgtct cccctggtgt ttttttattg ttt                                 1533
```

<210> SEQ ID NO 2
<211> LENGTH: 396
<212> TYPE: PRT
<213> ORGANISM: Carthamus tinctorius

<400> SEQUENCE: 2

```
Met Ala Leu Arg Ile Thr Pro Val Thr Leu Gln Ser Glu Arg Tyr Arg
1               5                   10                  15

Ser Phe Ser Phe Pro Lys Lys Ala Asn Leu Arg Ser Pro Lys Phe Ala
            20                  25                  30

Met Ala Ser Thr Leu Gly Ser Ser Thr Pro Lys Val Asp Asn Ala Lys
        35                  40                  45

Lys Pro Phe Gln Pro Pro Arg Glu Val His Val Gln Val Thr His Ser
    50                  55                  60

Met Pro Pro Gln Lys Ile Glu Ile Phe Lys Ser Ile Glu Gly Trp Ala
65                  70                  75                  80

Glu Gln Asn Ile Leu Val His Leu Lys Pro Val Glu Lys Cys Trp Gln
                85                  90                  95

Ala Gln Asp Phe Leu Pro Asp Pro Ala Ser Glu Gly Phe Asp Glu Gln
            100                 105                 110

Val Lys Glu Leu Arg Ala Arg Ala Lys Glu Ile Pro Asp Asp Tyr Phe
        115                 120                 125

Val Val Leu Val Gly Asp Met Ile Thr Glu Glu Ala Leu Pro Thr Tyr
    130                 135                 140
```

-continued

```
Gln Thr Met Leu Asn Thr Leu Asp Gly Val Arg Asp Glu Thr Gly Ala
145                 150                 155                 160

Ser Leu Thr Pro Trp Ala Val Trp Thr Arg Ala Trp Thr Ala Glu Glu
                165                 170                 175

Asn Arg His Gly Asp Leu Leu His Thr Tyr Leu Tyr Leu Ser Gly Arg
            180                 185                 190

Val Asp Met Arg Gln Ile Gln Lys Thr Ile Gln Tyr Leu Ile Gly Ser
        195                 200                 205

Gly Met Asp Pro Arg Thr Glu Asn Ser Pro Tyr Leu Gly Phe Ile Tyr
    210                 215                 220

Thr Ser Phe Gln Glu Arg Ala Thr Phe Val Ser His Gly Asn Thr Ala
225                 230                 235                 240

Arg His Ala Lys Asp His Gly Asp Val Lys Leu Ala Gln Ile Cys Gly
                245                 250                 255

Thr Ile Ala Ser Asp Glu Lys Arg His Glu Thr Ala Tyr Thr Lys Ile
            260                 265                 270

Val Glu Lys Leu Phe Glu Ile Asp Pro Asp Gly Thr Val Leu Ala Phe
        275                 280                 285

Ala Asp Met Met Arg Lys Lys Ile Ser Met Pro Ala His Leu Met Tyr
    290                 295                 300

Asp Gly Arg Asp Asp Asn Leu Phe Glu His Phe Ser Ala Val Ala Gln
305                 310                 315                 320

Arg Leu Gly Val Tyr Thr Ala Lys Asp Tyr Ala Asp Ile Leu Glu Phe
                325                 330                 335

Leu Val Gly Arg Trp Lys Val Ala Asp Leu Thr Gly Leu Ser Gly Glu
            340                 345                 350

Gly Arg Lys Ala Gln Asp Tyr Val Cys Gly Leu Pro Pro Arg Ile Arg
        355                 360                 365

Arg Leu Glu Glu Arg Ala Gln Gly Arg Ala Lys Glu Gly Pro Val Val
    370                 375                 380

Pro Phe Ser Trp Ile Phe Asp Arg Gln Val Lys Leu
385                 390                 395
```

<210> SEQ ID NO 3
<211> LENGTH: 1668
<212> TYPE: DNA
<213> ORGANISM: Ricinus communis

<400> SEQUENCE: 3

```
aaaagaaaaa ggtaagaaaa aaaacaatgg ctctcaagct caatcctttc ctttctcaaa     60

cccaaaagtt accttctttc gctcttccac caatggccag taccagatct cctaagttct    120

acatggcctc taccctcaag tctggttcta aggaagttga gaatctcaag aagcctttca    180

tgcctcctcg ggaggtacat gttcaggtta cccattctat gccaccccaa aagattgaga    240

tctttaaatc cctagacaat tgggctgagg agaacattct ggttcatctg aagccagttg    300

agaaatgttg gcaaccgcag gatttttttgc cagatcccgc ctctgatgga tttgatgagc    360

aagtcaggga actcagggag agagcaaagg agattcctga tgattatttt gttgttttgg    420

ttggagacat gataacggaa gaagcccttc ccacttatca aacaatgctg aataccttgg    480

atggagttcg ggatgaaaca ggtgcaagtc ctacttcttg ggcaatttgg acaagggcat    540

ggactgcgga agagaataga catggtgacc tcctcaataa gtatctctac ctatctggac    600

gagtggacat gaggcaaatt gagaagacaa ttcaatattt gattggttca ggaatggatc    660
```

-continued

```
cacggacaga aaacagtcca taccttgggt tcatctatac atcattccag gaaagggcaa    720

ccttcatttc tcatgggaac actgcccgac aagccaaaga gcatggagac ataaagttgg    780

ctcaaatatg tggtacaatt gctgcagatg agaagcgcca tgagacagcc tacacaaaga    840

tagtggaaaa actctttgag attgatcctg atggaactgt tttggctttt gctgatatga    900

tgagaaagaa aatttctatg cctgcacact tgatgtatga tggccgagat gataatcttt    960

ttgaccactt ttcagctgtt gcgcagcgtc ttggagtcta cacagcaaag gattatgcag   1020

atatattgga gttcttggtg ggcagatgga aggtggataa actaacgggc ctttcagctg   1080

agggacaaaa ggctcaggac tatgtttgtc ggttacctcc aagaattaga aggctggaag   1140

agagagctca aggaagggca aaggaagcac ccaccatgcc tttcagctgg attttcgata   1200

ggcaagtgaa gctgtaggtg gctaaagtgc aggacgaaac cgaaatggtt agtttcactc   1260

tttttcatgc ccatccctgc agaatcagaa gtagaggtag aattttgtag ttgctttttt   1320

attacaagtc cagtttagtt taaggtctgt ggaagggagt tagttgagga gtgaatttag   1380

taagttgtag atacagttgt ttcttgtgtt gtcatgagta tgctgataga gagcagctgt   1440

agttttgttg ttgtgttctt ttatatggtc tcttgtatga gtttcttttc tttccttttc   1500

ttctttcctt tcctctctct ctctctctct ctctctcttt ttctcttatc ccaagtgtct   1560

caagtataat aagcaaacga tccatgtggc aattttgatg atggtgatca gtctcacaac   1620

ttgatctttt gtcttctatt ggaaacacag cctgcttgtt tgaaaaaa                1668
```

```
<210> SEQ ID NO 4
<211> LENGTH: 396
<212> TYPE: PRT
<213> ORGANISM: Ricinus communis

<400> SEQUENCE: 4

Met Ala Leu Lys Leu Asn Pro Phe Leu Ser Gln Thr Gln Lys Leu Pro
1               5                   10                  15

Ser Phe Ala Leu Pro Pro Met Ala Ser Thr Arg Ser Pro Lys Phe Tyr
            20                  25                  30

Met Ala Ser Thr Leu Lys Ser Gly Ser Lys Glu Val Glu Asn Leu Lys
        35                  40                  45

Lys Pro Phe Met Pro Pro Arg Glu Val His Val Gln Val Thr His Ser
    50                  55                  60

Met Pro Pro Gln Lys Ile Glu Ile Phe Lys Ser Leu Asp Asn Trp Ala
65                  70                  75                  80

Glu Glu Asn Ile Leu Val His Leu Lys Pro Val Glu Lys Cys Trp Gln
                85                  90                  95

Pro Gln Asp Phe Leu Pro Asp Pro Ala Ser Asp Gly Phe Asp Glu Gln
            100                 105                 110

Val Arg Glu Leu Arg Glu Arg Ala Lys Glu Ile Pro Asp Asp Tyr Phe
        115                 120                 125

Val Val Leu Val Gly Asp Met Ile Thr Glu Glu Ala Leu Pro Thr Tyr
    130                 135                 140

Gln Thr Met Leu Asn Thr Leu Asp Gly Val Arg Asp Glu Thr Gly Ala
145                 150                 155                 160

Ser Pro Thr Ser Trp Ala Ile Trp Thr Arg Ala Trp Thr Ala Glu Glu
                165                 170                 175

Asn Arg His Gly Asp Leu Leu Asn Lys Tyr Leu Tyr Leu Ser Gly Arg
            180                 185                 190

Val Asp Met Arg Gln Ile Glu Lys Thr Ile Gln Tyr Leu Ile Gly Ser
```

-continued

```
        195                 200                 205

Gly Met Asp Pro Arg Thr Glu Asn Ser Pro Tyr Leu Gly Phe Ile Tyr
    210                 215                 220

Thr Ser Phe Gln Glu Arg Ala Thr Phe Ile Ser His Gly Asn Thr Ala
225                 230                 235                 240

Arg Gln Ala Lys Glu His Gly Asp Ile Lys Leu Ala Gln Ile Cys Gly
                245                 250                 255

Thr Ile Ala Ala Asp Glu Lys Arg His Glu Thr Ala Tyr Thr Lys Ile
            260                 265                 270

Val Glu Lys Leu Phe Glu Ile Asp Pro Asp Gly Thr Val Leu Ala Phe
        275                 280                 285

Ala Asp Met Met Arg Lys Lys Ile Ser Met Pro Ala His Leu Met Tyr
    290                 295                 300

Asp Gly Arg Asp Asp Asn Leu Phe Asp His Phe Ser Ala Val Ala Gln
305                 310                 315                 320

Arg Leu Gly Val Tyr Thr Ala Lys Asp Tyr Ala Asp Ile Leu Glu Phe
                325                 330                 335

Leu Val Gly Arg Trp Lys Val Asp Lys Leu Thr Gly Leu Ser Ala Glu
            340                 345                 350

Gly Gln Lys Ala Gln Asp Tyr Val Cys Arg Leu Pro Pro Arg Ile Arg
        355                 360                 365

Arg Leu Glu Glu Arg Ala Gln Gly Arg Ala Lys Glu Ala Pro Thr Met
    370                 375                 380

Pro Phe Ser Trp Ile Phe Asp Arg Gln Val Lys Leu
385                 390                 395


<210> SEQ ID NO 5
<211> LENGTH: 1495
<212> TYPE: DNA
<213> ORGANISM: Brassica campestris

<400> SEQUENCE: 5

tgagagatag tgtgagagca ttagccttag agagagagag agagagcttg tgtctgaaag     60

aatccacaaa tggcattgaa gcttaaccct ttggcatctc agccttacaa cttcccttcc    120

tcggctcgtc cgccaatctc tactttcaga tctcccaagt tcctctgcct cgcttcttct    180

tctcccgctc tcagctccaa ggaggttgag agtttgaaga agccattcac accacctaag    240

gaagtgcacg ttcaagtcct gcattccatg ccaccccaga agatcgagat cttcaaatcc    300

atggaagact gggccgagca gaaccttcta actcagctca aagacgtgga gaagtcgtgg    360

cagccccagg acttcttacc cgaccctgca tccgatgggt tcgaagatca ggttagagag    420

ctaagagaga gggcaagaga gctccctgat gattacttcg ttgttctggt gggagacatg    480

atcacggaag aggcgcttcc gacctatcaa accatgttga acactttgga tggagtgagg    540

gatgaaactg gcgctagccc cacttcatgg gctatttgga caagagcttg gactgcagaa    600

gagaaccgac acggtgatct tctcaataag tatctttact tgtctggacg tgttgacatg    660

aggcagattg aaaagaccat tcagtacttg attggttctg gaatggatcc tagaacagag    720

aacaatcctt acctcggctt catctacact tcattccaag aaagagccac cttcatctct    780

cacggaaaca cagctcgcca agccaaagag cacggagacc tcaagctagc ccaaatctgc    840

ggcacaatag ctgcagacga gaagcgtcat gagacagctt acaccaagat agttgagaag    900

ctctttgaga ttgatcctga tggtactgtg atggcgtttg cagacatgat gaggaagaaa    960

atctcgatgc ctgctcactt gatgtacgat gggcgggatg aaagcctctt tgacaacttc   1020
```

```
tcttctgttg ctcagaggct cggtgtttac actgccaaag actatgcgga cattcttgag   1080

tttttggttg ggaggtggaa gattgagagc ttgaccgggc tttcaggtga aggaaacaaa   1140

gcgcaagagt acttgtgtgg gttgactcca agaatcagga ggttggatga gagagctcaa   1200

gcaagagcca agaaaggacc caaggttcct ttcagctgga tacatgacag agaagtgcag   1260

ctctaaaaag gaacaaagct atgaaacctt ttcactctcc gtcgtccctc atttgatcta   1320

tctgctcttg aaattggtgt agattactat ggtttgtgat attgttcgtg ggtctagtta   1380

caaagttgag aagcagtgat ttagtagctt tgttgtttcc agtctttaaa tgtttttgtg   1440

tttggtcctt ttagtaaact tgttgtagtt aaatcagttg aactgtttgg tctgt        1495
```

```
<210> SEQ ID NO 6
<211> LENGTH: 398
<212> TYPE: PRT
<213> ORGANISM: Brassica campestris

<400> SEQUENCE: 6

Met Ala Leu Lys Leu Asn Pro Leu Ala Ser Gln Pro Tyr Asn Phe Pro
1               5                   10                  15

Ser Ser Ala Arg Pro Pro Ile Ser Thr Phe Arg Ser Pro Lys Phe Leu
            20                  25                  30

Cys Leu Ala Ser Ser Ser Pro Ala Leu Ser Ser Lys Glu Val Glu Ser
        35                  40                  45

Leu Lys Lys Pro Phe Thr Pro Pro Lys Glu Val His Val Gln Val Leu
    50                  55                  60

His Ser Met Pro Pro Gln Lys Ile Glu Ile Phe Lys Ser Met Glu Asp
65                  70                  75                  80

Trp Ala Glu Gln Asn Leu Leu Thr Gln Leu Lys Asp Val Glu Lys Ser
                85                  90                  95

Trp Gln Pro Gln Asp Phe Leu Pro Asp Pro Ala Ser Asp Gly Phe Glu
            100                 105                 110

Asp Gln Val Arg Glu Leu Arg Glu Arg Ala Arg Glu Leu Pro Asp Asp
        115                 120                 125

Tyr Phe Val Val Leu Val Gly Asp Met Ile Thr Glu Glu Ala Leu Pro
    130                 135                 140

Thr Tyr Gln Thr Met Leu Asn Thr Leu Asp Gly Val Arg Asp Glu Thr
145                 150                 155                 160

Gly Ala Ser Pro Thr Ser Trp Ala Ile Trp Thr Arg Ala Trp Thr Ala
                165                 170                 175

Glu Glu Asn Arg His Gly Asp Leu Leu Asn Lys Tyr Leu Tyr Leu Ser
            180                 185                 190

Gly Arg Val Asp Met Arg Gln Ile Glu Lys Thr Ile Gln Tyr Leu Ile
        195                 200                 205

Gly Ser Gly Met Asp Pro Arg Thr Glu Asn Asn Pro Tyr Leu Gly Phe
    210                 215                 220

Ile Tyr Thr Ser Phe Gln Glu Arg Ala Thr Phe Ile Ser His Gly Asn
225                 230                 235                 240

Thr Ala Arg Gln Ala Lys Glu His Gly Asp Leu Lys Leu Ala Gln Ile
                245                 250                 255

Cys Gly Thr Ile Ala Ala Asp Glu Lys Arg His Glu Thr Ala Tyr Thr
            260                 265                 270

Lys Ile Val Glu Lys Leu Phe Glu Ile Asp Pro Asp Gly Thr Val Met
        275                 280                 285
```

-continued

```
Ala Phe Ala Asp Met Met Arg Lys Lys Ile Ser Met Pro Ala His Leu
    290                 295                 300

Met Tyr Asp Gly Arg Asp Glu Ser Leu Phe Asp Asn Phe Ser Ser Val
305                 310                 315                 320

Ala Gln Arg Leu Gly Val Tyr Thr Ala Lys Asp Tyr Ala Asp Ile Leu
                325                 330                 335

Glu Phe Leu Val Gly Arg Trp Lys Ile Glu Ser Leu Thr Gly Leu Ser
            340                 345                 350

Gly Glu Gly Asn Lys Ala Gln Glu Tyr Leu Cys Gly Leu Thr Pro Arg
        355                 360                 365

Ile Arg Arg Leu Asp Glu Arg Ala Gln Ala Arg Ala Lys Lys Gly Pro
    370                 375                 380

Lys Val Pro Phe Ser Trp Ile His Asp Arg Glu Val Gln Leu
385                 390                 395


<210> SEQ ID NO 7
<211> LENGTH: 143
<212> TYPE: DNA
<213> ORGANISM: Simmondsia chinensis
<220> FEATURE:
<221> NAME/KEY: misc_feature
<222> LOCATION: (11)..(11)
<223> OTHER INFORMATION: N= A, T, C or G

<400> SEQUENCE: 7

gatgccaaaa ngcctcacat gcctcctaga gaagctcatg tgcaaaagac ccattcaatk      60

ccgcctcaaa agattgagat tttcaaatcc ttggagggtt gggctgagga gaatgtcttg     120

gtgcatctta aacctgtgga gaa                                             143


<210> SEQ ID NO 8
<211> LENGTH: 47
<212> TYPE: PRT
<213> ORGANISM: Simmondsia chinensis
<220> FEATURE:
<221> NAME/KEY: misc_feature
<222> LOCATION: (4)..(4)
<223> OTHER INFORMATION: Xaa= any amino acid
<220> FEATURE:
<221> NAME/KEY: MISC_FEATURE
<222> LOCATION: (20)..(20)
<223> OTHER INFORMATION: Xaa= any amino acid

<400> SEQUENCE: 8

Asp Ala Lys Xaa Pro His Met Pro Pro Arg Glu Ala His Val Gln Lys
1               5                   10                  15

Thr His Ser Xaa Pro Pro Gln Lys Ile Glu Ile Phe Lys Ser Leu Glu
            20                  25                  30

Gly Trp Ala Glu Glu Asn Val Leu Val His Leu Lys Pro Val Glu
        35                  40                  45


<210> SEQ ID NO 9
<211> LENGTH: 1561
<212> TYPE: DNA
<213> ORGANISM: Umbellularia californica

<400> SEQUENCE: 9

agagagagag agagagagag agctaaatta aaaaaaaaac ccagaagtgg gaaatcttcc      60

ccatgaaata acggatcctc ttgctactgc tactactact actacaaact gtagccattt     120

atataattct atataatttt caacatggcc accacctctt tagcttccgc tttctgctcg     180

atgaaagctg taatgttggc tcgtgatggc cggggcatga aacccaggag cagtgatttg     240
```

-continued

```
cagctgaggg cgggaaatgc gccaacctct ttgaagatga tcaatgggac caagttcagt     300

tacacggaga gcttgaaaag gttgcctgac tggagcatgc tctttgcagt gatcacaacc     360

atcttttcgg ctgctgagaa gcagtggacc aatctagagt ggaagccgaa gccgaagcta     420

ccccagttgc ttgatgacca ttttggactg catgggttag ttttcaggcg cacctttgcc     480

atcagatctt atgaggtggg acctgaccgc tccacatcta tactggctgt tatgaatcac     540

atgcaggagg ctacacttaa tcatgcgaag agtgtgggaa ttctaggaga tggattcggg     600

acgacgctag agatgagtaa gagagatctg atgtgggttg tgagacgcac gcatgttgct     660

gtggaacggt accctacttg ggtgatact gtagaagtag agtgctggat tggtgcatct     720

ggaaataatg gcatgcgacg tgatttcctt gtccgggact gcaaaacagg cgaaattctt     780

acaagatgta ccagcctttc ggtgctgatg aatacaagga caaggaggtt gtccacaatc     840

cctgacgaag ttagagggga gatagggcct gcattcattg ataatgtggc tgtcaaggac     900

gatgaaatta agaaactaca gaagctcaat gacagcactg cagattacat ccaaggaggt     960

ttgactcctc gatggaatga tttggatgtc aatcagcatg tgaacaacct caaatacgtt    1020

gcctgggttt ttgagaccgt cccagactcc atctttgaga gtcatcatat ttccagcttc    1080

actcttgaat acaggagaga gtgcacgagg gatagcgtgc tgcggtccct gaccactgtc    1140

tctggtggct cgtcggaggc tgggttagtg tgcgatcact tgctccagct tgaaggtggg    1200

tctgaggtat tgagggcaag aacagagtgg aggcctaagc ttaccgatag tttcagaggg    1260

attagtgtga tacccgcaga accgagggtg taactaatga aagaagcatc tgttgaagtt    1320

tctcccatgc tgttcgtgag gatacttttt agaagctgca gtttgcattg cttgtgcaga    1380

atcatggtct gtggttttag atgtatataa aaaatagtcc tgtagtcatg aaacttaata    1440

tcagaaaaat aactcaatgg gtcaaggtta tcgaagtagt catttaagct ttgaaatatg    1500

ttttgtattc ctcggcttaa tctgtaagct ctttctcttg caataaagtt cgcctttcaa    1560

t                                                                    1561

<210> SEQ ID NO 10
<211> LENGTH: 382
<212> TYPE: PRT
<213> ORGANISM: Umbellularia californica

<400> SEQUENCE: 10

Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Pro Thr Ser Leu Lys Met Ile Asn Gly
        35                  40                  45

Thr Lys Phe Ser Tyr Thr Glu Ser Leu Lys Arg Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Lys Leu Pro Gln Leu Leu
                85                  90                  95

Asp Asp His Phe Gly Leu His Gly Leu Val Phe Arg Arg Thr Phe Ala
            100                 105                 110

Ile Arg Ser Tyr Glu Val Gly Pro Asp Arg Ser Thr Ser Ile Leu Ala
        115                 120                 125
```

-continued

```
Val Met Asn His Met Gln Glu Ala Thr Leu Asn His Ala Lys Ser Val
    130                 135                 140

Gly Ile Leu Gly Asp Gly Phe Gly Thr Thr Leu Glu Met Ser Lys Arg
145                 150                 155                 160

Asp Leu Met Trp Val Val Arg Arg Thr His Val Ala Val Glu Arg Tyr
                165                 170                 175

Pro Thr Trp Gly Asp Thr Val Glu Val Glu Cys Trp Ile Gly Ala Ser
            180                 185                 190

Gly Asn Asn Gly Met Arg Arg Asp Phe Leu Val Arg Asp Cys Lys Thr
        195                 200                 205

Gly Glu Ile Leu Thr Arg Cys Thr Ser Leu Ser Val Leu Met Asn Thr
    210                 215                 220

Arg Thr Arg Arg Leu Ser Thr Ile Pro Asp Glu Val Arg Gly Glu Ile
225                 230                 235                 240

Gly Pro Ala Phe Ile Asp Asn Val Ala Val Lys Asp Asp Glu Ile Lys
                245                 250                 255

Lys Leu Gln Lys Leu Asn Asp Ser Thr Ala Asp Tyr Ile Gln Gly Gly
            260                 265                 270

Leu Thr Pro Arg Trp Asn Asp Leu Asp Val Asn Gln His Val Asn Asn
        275                 280                 285

Leu Lys Tyr Val Ala Trp Val Phe Glu Thr Val Pro Asp Ser Ile Phe
    290                 295                 300

Glu Ser His His Ile Ser Ser Phe Thr Leu Glu Tyr Arg Arg Glu Cys
305                 310                 315                 320

Thr Arg Asp Ser Val Leu Arg Ser Leu Thr Thr Val Ser Gly Gly Ser
                325                 330                 335

Ser Glu Ala Gly Leu Val Cys Asp His Leu Leu Gln Leu Glu Gly Gly
            340                 345                 350

Ser Glu Val Leu Arg Ala Arg Thr Glu Trp Arg Pro Lys Leu Thr Asp
        355                 360                 365

Ser Phe Arg Gly Ile Ser Val Ile Pro Ala Glu Pro Arg Val
    370                 375                 380
```

<210> SEQ ID NO 11
<211> LENGTH: 1435
<212> TYPE: DNA
<213> ORGANISM: Umbellularia californica

<400> SEQUENCE: 11

```
aaaaaagtac aaactgtatg gtagccattt acatataact actctataat tttcaacatg     60

gtcaccacct ctttagcttc cgctttcttc tcgatgaaag ctgtaatgtt ggctcctgat    120

ggcagtggca taaaacccag gagcagtggt ttgcaggtga gggcgggaaa ggaacaaaac    180

tcttgcaaga tgatcaatgg gaccaaggtc aaagacacgg agggcttgaa agggcgcagc    240

acattgcatg gctggagcat gccccttgaa ttgatcacaa ccatcttttc ggctgctgag    300

aagcagtgga ccaatctagt tagtaagcca ccgcagttgc ttgatgacca tttaggtctg    360

catgggctag ttttcaggcg cacctttgca atcagatgca gtgaggttgg acctgaccgc    420

tccacatcca tagtggctgt tatgaattac ttgcaggaag ctgcatgtaa tcatgcggag    480

agtctgggac ttctaggaga tggattcggt gagacactag agatgagtag gagagatctg    540

atatgggttg tgagacgcac gcatgttgtt gtgggaacgt accctgcttg ggcgatact     600

gttgaagtcg aggcctggat cggtgcagct ggaaacattg gcatgcgccg ccattttctt    660

gtccgcgact gcaaaactgg ccacattctt gcaagatgta ccagtgtttc agtgatgatg    720
```

-continued aatatgagga caaggagatt gtccaaaatt ccccaagaag ttagagggga gattgaccct 780
cttttcatcg aaaagtttgc tgtcaaggaa ggggaaatta agaaattaca gaagttcaat 840
gatagcactg cagattacat tcaaggggt tggactccgc gatggaatga tttggatgtc 900
aatcagcacg tgaacaatat caaatacgtt ggctggattt ttaagagcgt cccagactct 960
atctatgaga atcatcatct ttctagcatc actctcgaat acaggagaga gtgcacaagg 1020
ggcagagcac tgcagtccct gaccactgtt tgtggtggct cgtccgaagc tgggatcata 1080
tgtgagcacc tactccagct tgaggatggg tctgaggttt tgaggggaag aacagattgg 1140
aggcccaagc gcaccgatag tttcgaaggc attagtgaga gattcccgca gcaagaaccg 1200
cataattaat gacagaagca tcagatatag tttctcctgt gctgttcctg agaatgcatc 1260
ttacaagtcg tggtttggat tgcttgtgca gaatcatggt ttgtgctttc agaagtatat 1320
ctaaattagt ccaagttata tgactccata ttggaaaata actcaatgag tcgtgctctt 1380
gaaatggtct tttaagcttt gaaataaagt tccacttaat ccatgtaaaa aaaaa 1435

<210> SEQ ID NO 12
<211> LENGTH: 383
<212> TYPE: PRT
<213> ORGANISM: Umbellularia californica

<400> SEQUENCE: 12

```
Met Val Thr Thr Ser Leu Ala Ser Ala Phe Phe Ser Met Lys Ala Val
1               5                   10                  15

Met Leu Ala Pro Asp Gly Ser Gly Ile Lys Pro Arg Ser Ser Gly Leu
            20                  25                  30

Gln Val Arg Ala Gly Lys Glu Gln Asn Ser Cys Lys Met Ile Asn Gly
        35                  40                  45

Thr Lys Val Lys Asp Thr Glu Gly Leu Lys Gly Arg Ser Thr Leu His
    50                  55                  60

Gly Trp Ser Met Pro Leu Glu Leu Ile Thr Thr Ile Phe Ser Ala Ala
65                  70                  75                  80

Glu Lys Gln Trp Thr Asn Leu Val Ser Lys Pro Pro Gln Leu Leu Asp
                85                  90                  95

Asp His Leu Gly Leu His Gly Leu Val Phe Arg Arg Thr Phe Ala Ile
            100                 105                 110

Arg Cys Ser Glu Val Gly Pro Asp Arg Ser Thr Ser Ile Val Ala Val
        115                 120                 125

Met Asn Tyr Leu Gln Glu Ala Ala Cys Asn His Ala Glu Ser Leu Gly
    130                 135                 140

Leu Leu Gly Asp Gly Phe Gly Glu Thr Leu Glu Met Ser Arg Arg Asp
145                 150                 155                 160

Leu Ile Trp Val Val Arg Arg Thr His Val Val Val Gly Thr Tyr Pro
                165                 170                 175

Ala Trp Gly Asp Thr Val Glu Val Glu Ala Trp Ile Gly Ala Ala Gly
            180                 185                 190

Asn Ile Gly Met Arg Arg His Phe Leu Val Arg Asp Cys Lys Thr Gly
        195                 200                 205

His Ile Leu Ala Arg Cys Thr Ser Val Ser Val Met Met Asn Met Arg
    210                 215                 220

Thr Arg Arg Leu Ser Lys Ile Pro Gln Glu Val Arg Gly Glu Ile Asp
225                 230                 235                 240

Pro Leu Phe Ile Glu Lys Phe Ala Val Lys Glu Gly Glu Ile Lys Lys
```

-continued

```
                245                 250                 255

Leu Gln Lys Phe Asn Asp Ser Thr Ala Asp Tyr Ile Gln Gly Gly Trp
            260                 265                 270

Thr Pro Arg Trp Asn Asp Leu Asp Val Asn Gln His Val Asn Asn Ile
        275                 280                 285

Lys Tyr Val Gly Trp Ile Phe Lys Ser Val Pro Asp Ser Ile Tyr Glu
    290                 295                 300

Asn His His Leu Ser Ser Ile Thr Leu Glu Tyr Arg Arg Glu Cys Thr
305                 310                 315                 320

Arg Gly Arg Ala Leu Gln Ser Leu Thr Thr Val Cys Gly Gly Ser Ser
                325                 330                 335

Glu Ala Gly Ile Ile Cys Glu His Leu Leu Gln Leu Glu Asp Gly Ser
            340                 345                 350

Glu Val Leu Arg Gly Arg Thr Asp Trp Arg Pro Lys Arg Thr Asp Ser
        355                 360                 365

Phe Glu Gly Ile Ser Glu Arg Phe Pro Gln Gln Glu Pro His Asn
    370                 375                 380


<210> SEQ ID NO 13
<211> LENGTH: 1561
<212> TYPE: DNA
<213> ORGANISM: Carthamus tinctorius
<220> FEATURE:
<221> NAME/KEY: misc_feature
<222> LOCATION: (1419)..(1422)
<223> OTHER INFORMATION: N=A, T, C or G

<400> SEQUENCE: 13

gggtaacatg gcataaacgt gaataactgc aactccagtg tcactttccc tttcctttcc      60

accaccatct cctccctcgg tcccatcgac ggcaaactcc ataaaaccac caccacctct     120

tcaaatcaac acctcttccg aaccaccacc accaccaccg ccgccggcaa ctatgctatc     180

acgacctctt ccgaccaccg ccgcggcggc gaccacgacg acgaataatt gcaatggcgt     240

caactcccgc ggcgccttac ctcattcccg atccgttgga ttcgcctcga ttcggaaacg     300

aagcaccggt tccttatgca attcgccgcc gcggacggtg gcgccggtga tggcggtgag     360

gaccggtgag caaccgaccg gcgttgccgt cggattgaag gaggcggagg cggaggtgga     420

gaagagcctg gcggatcggc ttcggatggg gagcttgacg gaagatggat tgtcgtataa     480

ggagaggttc atcataaggt gttatgaagt cgggattaat aagactgcaa ctgttgaaac     540

cattgctaat ctattgcagg aggttggagg taatcatgct cagagtgttg gattttcaac     600

agacggattt gccaccacga ccactatgcg aaaattgcat ctcatatggg tgacttcgcg     660

aatgcacatt gaaatttaca gataccccgc ttggagtgat gtggttgaaa tcgagacttg     720

gtgtcaaagt gaaggaagga ttgggactag acgtgattgg attatgaaag accatgcgag     780

tggtgaagtc attggaaggg ctacaagcaa atgggtgatg atgaacgagg atactagaag     840

actccagaaa gtcaacgatg acgtcagaga cgaatatctc gttttttgtc ccaagacacc     900

aagattagca tttcctgaaa agaacactag cagcctgaag aaaatagcaa aactagaaga     960

ccccgccgaa tattcgacgc tagggcttgt gccaagaaga gccgatctcg atatgaacaa    1020

gcatgttaac aatgttacct acattggatg ggttcttgag agcatcccac aagaagtcat    1080

cgacactcat gaactacaaa cgattaccct agactaccgg cgggaatgcc agcatgacga    1140

catagtcgat tccctcacga gttccgagtc actactcgac gatgccgcca tctcgaaact    1200

cgaaggaacc aacggatctt ctgttcccaa aaaagacgaa acggatttga gccggttttt    1260
```

-continued

```
gcatttacta cgatcatcgg gcgatggtct cgaactaaat aggggtcgca ccgagtggag   1320

aaagaaaccc gcgaaaaaat gagcaacacc cttcggtttg tttagcgtac cctttttgc    1380

gtgttttcaa tccatttttc ataattcgcc ttttagggnn nngccgtttt tatgtagcgt   1440

atttgttgta gatggactag gttttcggat tctcgaaccg gataggtgct atctttatct   1500

tcctatgttt tgcttgtaga atggtatgaa taaactagtt tcgaagtaat gtttttggta   1560

g                                                                   1561


<210> SEQ ID NO 14
<211> LENGTH: 389
<212> TYPE: PRT
<213> ORGANISM: Carthamus tinctorius

<400> SEQUENCE: 14

Met Leu Ser Arg Pro Leu Pro Thr Thr Ala Ala Ala Ala Thr Thr Thr
1               5                   10                  15

Thr Asn Asn Cys Asn Gly Val Asn Ser Arg Gly Ala Leu Pro His Ser
            20                  25                  30

Arg Ser Val Gly Phe Ala Ser Ile Arg Lys Arg Ser Thr Gly Ser Leu
        35                  40                  45

Cys Asn Ser Pro Pro Arg Thr Val Ala Pro Val Met Ala Val Arg Thr
    50                  55                  60

Gly Glu Gln Pro Thr Gly Val Ala Val Gly Leu Lys Glu Ala Glu Ala
65                  70                  75                  80

Glu Val Glu Lys Ser Leu Ala Asp Arg Leu Arg Met Gly Ser Leu Thr
                85                  90                  95

Glu Asp Gly Leu Ser Tyr Lys Glu Arg Phe Ile Ile Arg Cys Tyr Glu
            100                 105                 110

Val Gly Ile Asn Lys Thr Ala Thr Val Glu Thr Ile Ala Asn Leu Leu
        115                 120                 125

Gln Glu Val Gly Gly Asn His Ala Gln Ser Val Gly Phe Ser Thr Asp
    130                 135                 140

Gly Phe Ala Thr Thr Thr Thr Met Arg Lys Leu His Leu Ile Trp Val
145                 150                 155                 160

Thr Ser Arg Met His Ile Glu Ile Tyr Arg Tyr Pro Ala Trp Ser Asp
                165                 170                 175

Val Val Glu Ile Glu Thr Trp Cys Gln Ser Glu Gly Arg Ile Gly Thr
            180                 185                 190

Arg Arg Asp Trp Ile Met Lys Asp His Ala Ser Gly Glu Val Ile Gly
        195                 200                 205

Arg Ala Thr Ser Lys Trp Val Met Met Asn Glu Asp Thr Arg Arg Leu
    210                 215                 220

Gln Lys Val Asn Asp Asp Val Arg Asp Glu Tyr Leu Val Phe Cys Pro
225                 230                 235                 240

Lys Thr Pro Arg Leu Ala Phe Pro Glu Lys Asn Thr Ser Ser Leu Lys
                245                 250                 255

Lys Ile Ala Lys Leu Glu Asp Pro Ala Glu Tyr Ser Thr Leu Gly Leu
            260                 265                 270

Val Pro Arg Arg Ala Asp Leu Asp Met Asn Lys His Val Asn Asn Val
        275                 280                 285

Thr Tyr Ile Gly Trp Val Leu Glu Ser Ile Pro Gln Glu Val Ile Asp
    290                 295                 300

Thr His Glu Leu Gln Thr Ile Thr Leu Asp Tyr Arg Arg Glu Cys Gln
```

-continued

```
305                 310                 315                 320

His Asp Asp Ile Val Asp Ser Leu Thr Ser Ser Glu Ser Leu Leu Asp
                325                 330                 335

Asp Ala Ala Ile Ser Lys Leu Glu Gly Thr Asn Gly Ser Ser Val Pro
            340                 345                 350

Lys Lys Asp Glu Thr Asp Leu Ser Arg Phe Leu His Leu Leu Arg Ser
        355                 360                 365

Ser Gly Asp Gly Leu Glu Leu Asn Arg Gly Arg Thr Glu Trp Arg Lys
    370                 375                 380

Lys Pro Ala Lys Lys
385


<210> SEQ ID NO 15
<211> LENGTH: 1312
<212> TYPE: DNA
<213> ORGANISM: Carthamus tinctorius

<400> SEQUENCE: 15

gcacaaacca ggaaaaaaaa aaccctctct ccctaaccta actcgccatc ggagaaatct      60

ctgtcgacgg tgacgttcga gatcgtaaca atcatgctat cgaaaggtgc tccggcggca     120

ccggcggtgg cggcgatgta caatgcctcc gccaaagaca ctacttttgc cctaactcac     180

tcccgatcga ttggttccgt ctcaattcgc agacgataca acgtgttttt gtgcaattct     240

tcgtcgtcgt cgagaaaggt ttctccgttg ctagcggtgg cgaccggaga gcagccgagc     300

ggtgttgcta gtttacgtga ggcggataag gagaagagct tggggaaccg gctacggttg     360

gggagcttga cggaggatgg attatcgtat aaggagaagt tcgttataag gtgttatgaa     420

gtcggaatta acaaaactgc tacgattgaa acgattgcaa atctgttgca ggaggttgga     480

ggtaatcatg ctcagggtgt tggattttct actgatgggt ttgccacaac gaccactatg     540

aggaaattgc atctcatatg ggttactgca cgaatgcata ttgaaatata tagataccct     600

gcttggagtg atgtgattga aattgagact tgggttcagg gtgaggggaa ggtcgggacc     660

aggcgtgatt ggatcctcaa agactatgcc aatggtgagg ttattggaag ggccacaagc     720

aaatgggtga tgatgaacga ggatactaga agattgcaga aagtcagtga tgatgtcaga     780

gaggagtatt tagtgttttg ccccaggaca ttgagattag catttcctga agagaacaac     840

aatagcatga agaaaatacc aaaactggaa gatccagctg aatattccag gcttggactt     900

gtgccaagga gatccgattt ggatatgaac aaacacgtta acaatgttac ctacatcggg     960

tgggctctag agagcatccc accagaaatc atcgacaccc atgaactgca agctattacc    1020

ttagactaca gacgtgaatg ccaacgggat gacatagttg attcactcac tagccgtgaa    1080

ccactcggaa atgctgcagg tgtcaagttt aaagaaatca atggatctgt ttcccccaaa    1140

aaggacgaac aagatctaag ccgatttatg catctactga gatcagctgg cagtggtctt    1200

gaaatcaaca ggtgtcgcac cgaatggaga aagaagccag caaaaagata agcatatctg    1260

atccctcgat tgtaccgttt taccgttcct gttcaaagtc tagtttcttt tt            1312


<210> SEQ ID NO 16
<211> LENGTH: 385
<212> TYPE: PRT
<213> ORGANISM: Carthamus tinctorius

<400> SEQUENCE: 16

Met Leu Ser Lys Gly Ala Pro Ala Ala Pro Ala Val Ala Ala Met Tyr
1               5                   10                  15
```

-continued

```
Asn Ala Ser Ala Lys Asp Thr Thr Phe Ala Leu Thr His Ser Arg Ser
            20                  25                  30

Ile Gly Ser Val Ser Ile Arg Arg Arg Tyr Asn Val Phe Leu Cys Asn
        35                  40                  45

Ser Ser Ser Ser Ser Arg Lys Val Ser Pro Leu Leu Ala Val Ala Thr
    50                  55                  60

Gly Glu Gln Pro Ser Gly Val Ala Ser Leu Arg Glu Ala Asp Lys Glu
65                  70                  75                  80

Lys Ser Leu Gly Asn Arg Leu Arg Leu Gly Ser Leu Thr Glu Asp Gly
                85                  90                  95

Leu Ser Tyr Lys Glu Lys Phe Val Ile Arg Cys Tyr Glu Val Gly Ile
            100                 105                 110

Asn Lys Thr Ala Thr Ile Glu Thr Ile Ala Asn Leu Leu Gln Glu Val
        115                 120                 125

Gly Gly Asn His Ala Gln Gly Val Gly Phe Ser Thr Asp Gly Phe Ala
    130                 135                 140

Thr Thr Thr Thr Met Arg Lys Leu His Leu Ile Trp Val Thr Ala Arg
145                 150                 155                 160

Met His Ile Glu Ile Tyr Arg Tyr Pro Ala Trp Ser Asp Val Ile Glu
                165                 170                 175

Ile Glu Thr Trp Val Gln Gly Glu Gly Lys Val Gly Thr Arg Arg Asp
            180                 185                 190

Trp Ile Leu Lys Asp Tyr Ala Asn Gly Glu Val Ile Gly Arg Ala Thr
        195                 200                 205

Ser Lys Trp Val Met Met Asn Glu Asp Thr Arg Arg Leu Gln Lys Val
    210                 215                 220

Ser Asp Asp Val Arg Glu Glu Tyr Leu Val Phe Cys Pro Arg Thr Leu
225                 230                 235                 240

Arg Leu Ala Phe Pro Glu Glu Asn Asn Asn Ser Met Lys Lys Ile Pro
                245                 250                 255

Lys Leu Glu Asp Pro Ala Glu Tyr Ser Arg Leu Gly Leu Val Pro Arg
            260                 265                 270

Arg Ser Asp Leu Asp Met Asn Lys His Val Asn Asn Val Thr Tyr Ile
        275                 280                 285

Gly Trp Ala Leu Glu Ser Ile Pro Pro Glu Ile Ile Asp Thr His Glu
    290                 295                 300

Leu Gln Ala Ile Thr Leu Asp Tyr Arg Arg Glu Cys Gln Arg Asp Asp
305                 310                 315                 320

Ile Val Asp Ser Leu Thr Ser Arg Glu Pro Leu Gly Asn Ala Ala Gly
                325                 330                 335

Val Lys Phe Lys Glu Ile Asn Gly Ser Val Ser Pro Lys Lys Asp Glu
            340                 345                 350

Gln Asp Leu Ser Arg Phe Met His Leu Leu Arg Ser Ala Gly Ser Gly
        355                 360                 365

Leu Glu Ile Asn Arg Cys Arg Thr Glu Trp Arg Lys Lys Pro Ala Lys
    370                 375                 380

Arg
385
```

<210> SEQ ID NO 17
<211> LENGTH: 1461
<212> TYPE: DNA
<213> ORGANISM: Cinnamomum camphora

<400> SEQUENCE: 17

```
tcaacatggc caccacctct ttagcttctg ctttctgctc gatgaaagct gtaatgttgg     60
ctcgtgatgg caggggcatg aaacccagga gcagtgattt gcagctgagg gcgggaaatg    120
cacaaacctc tttgaagatg atcaatggga ccaagttcag ttacacagag agcttgaaaa    180
agttgcctga ctggagcatg ctctttgcag tgatcacgac catcttttcg gctgctgaga    240
agcagtggac caatctagag tggaagccga agccgaatcc accccagttg cttgatgacc    300
attttgggcc gcatgggtta gttttcaggc gcacctttgc catcagatcg tatgaggtgg    360
gacctgaccg ctccacatct atagtggctg ttatgaatca cttgcaggag gctgcactta    420
atcatgcgaa gagtgtggga attctaggag atggattcgg tacgacgcta gagatgagta    480
agagagatct gatatgggtt gtgaaacgca cgcatgttgc tgtggaacgg taccctgctt    540
ggggtgatac tgttgaagta gagtgctggg ttggtgcatc gggaaataat ggcaggcgcc    600
atgatttcct tgtccgggac tgcaaaacag gcgaaattct tacaagatgt accagtcttt    660
cggtgatgat gaatacaagg acaaggaggt tgtccaaaat ccctgaagaa gttagagggg    720
agataggccc tgcattcatt gataatgtgg ctgtcaagga cgaggaaatt aagaaaccac    780
agaagctcaa tgacagcact gcagattaca tccaaggagg attgactcct cgatggaatg    840
atttggatat caatcagcac gttaacaaca tcaaatacgt tgactggatt cttgagactg    900
tcccagactc aatctttgag agtcatcata tttccagctt cactattgaa tacaggagag    960
agtgcacgat ggatagcgtg ctgcagtccc tgaccactgt ctccggtggc tcgtcggaag   1020
ctgggttagt gtgcgagcac ttgctccagc ttgaaggtgg gtctgaggta ttgagggcaa   1080
aaacagagtg gaggcctaag cttaccgata gtttcagagg gattagtgtg atacccgcag   1140
aatcgagtgt ctaactaacg aaagaagcat ctgatgaagt ttctcctgtg ctgttgttcg   1200
tgaggatgct ttttagaagc tgcagtttgc attgcttgtg cagaatcatg gcctgtggtt   1260
ttagatatat atccaaaatt gtcctatagt caagaaactt aatatcagaa aaataactca   1320
atgagtcaag gttatcgaag tagtcatgta agctttgaaa tatgttgtgt attcctcggc   1380
tttatgtaat ctgtaagctc tttctcttgc aataaatttc gcctttcaat aataaaaaaa   1440
aaaaaaaaag gtcgactcga g                                             1461
```

<210> SEQ ID NO 18
<211> LENGTH: 382
<212> TYPE: PRT
<213> ORGANISM: Cinnamomum camphora

<400> SEQUENCE: 18

```
Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Gln Thr Ser Leu Lys Met Ile Asn Gly
        35                  40                  45

Thr Lys Phe Ser Tyr Thr Glu Ser Leu Lys Lys Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Asn Pro Pro Gln Leu Leu
                85                  90                  95

Asp Asp His Phe Gly Pro His Gly Leu Val Phe Arg Arg Thr Phe Ala
```

-continued

```
            100                 105                 110

Ile Arg Ser Tyr Glu Val Gly Pro Asp Arg Ser Thr Ser Ile Val Ala
        115                 120                 125

Val Met Asn His Leu Gln Glu Ala Ala Leu Asn His Ala Lys Ser Val
    130                 135                 140

Gly Ile Leu Gly Asp Gly Phe Gly Thr Thr Leu Glu Met Ser Lys Arg
145                 150                 155                 160

Asp Leu Ile Trp Val Val Lys Arg Thr His Val Ala Val Glu Arg Tyr
                165                 170                 175

Pro Ala Trp Gly Asp Thr Val Glu Val Glu Cys Trp Val Gly Ala Ser
            180                 185                 190

Gly Asn Asn Gly Arg Arg His Asp Phe Leu Val Arg Asp Cys Lys Thr
        195                 200                 205

Gly Glu Ile Leu Thr Arg Cys Thr Ser Leu Ser Val Met Met Asn Thr
    210                 215                 220

Arg Thr Arg Arg Leu Ser Lys Ile Pro Glu Glu Val Arg Gly Glu Ile
225                 230                 235                 240

Gly Pro Ala Phe Ile Asp Asn Val Ala Val Lys Asp Glu Glu Ile Lys
                245                 250                 255

Lys Pro Gln Lys Leu Asn Asp Ser Thr Ala Asp Tyr Ile Gln Gly Gly
            260                 265                 270

Leu Thr Pro Arg Trp Asn Asp Leu Asp Ile Asn Gln His Val Asn Asn
        275                 280                 285

Ile Lys Tyr Val Asp Trp Ile Leu Glu Thr Val Pro Asp Ser Ile Phe
    290                 295                 300

Glu Ser His His Ile Ser Ser Phe Thr Ile Glu Tyr Arg Arg Glu Cys
305                 310                 315                 320

Thr Met Asp Ser Val Leu Gln Ser Leu Thr Thr Val Ser Gly Gly Ser
                325                 330                 335

Ser Glu Ala Gly Leu Val Cys Glu His Leu Leu Gln Leu Glu Gly Gly
            340                 345                 350

Ser Glu Val Leu Arg Ala Lys Thr Glu Trp Arg Pro Lys Leu Thr Asp
        355                 360                 365

Ser Phe Arg Gly Ile Ser Val Ile Pro Ala Glu Ser Ser Val
    370                 375                 380
```

<210> SEQ ID NO 19
<211> LENGTH: 1307
<212> TYPE: DNA
<213> ORGANISM: Brassica campestris

<400> SEQUENCE: 19

```
gctcgcctcc cacattttct tcttcgatcc cgaaaagatg ttgaagctct cgtgtaatgc     60

gactgataag ttacagaccc tcttctcgca ttctcatcaa ccggatccgg cacaccggag    120

aaccgtctcc tccgtgtcgt gctctcatct gaggaaaccg gttctcgatc ctttgcgagc    180

gatcgtatct gctgatcaag gaagtgtgat tcgagcagaa caaggtttgg gctcactcgc    240

ggatcagctc cgattgggta gcttgacgga ggatggtttg tcgtataagg agaagttcat    300

cgtcagatcc tacgaagtgg ggagtaacaa gaccgccact gtcgaaaccg tcgctaatct    360

tttgcaggag gtgggatgta atcatgcgca gagcgttgga ttctcgactg atgggtttgc    420

gacaacaccg accatgagga aactgcatct catttgggtc actgcgagaa tgcatataga    480

gatctacaag taccctgctt ggggtgatgt ggttgagata gagacatggt gtcagagtga    540
```

-continued

```
aggaaggatc gggactaggc gtgattggat tcttaaggat gttgctacgg gtgaagtcac    600

tggccgtgct acaagcaagt gggtgatgat gaaccaagac acaagacggc ttcagaaagt    660

ttctgatgat gttcgggacg agtacttggt cttctgtcct aaagaactca gattagcatt    720

tcctgaggag aataacagaa gcttgaagaa aattccgaaa ctcgaagatc cagctcagta    780

ttcgatgatt gggcttaagc ctagacgagc tgatctcgac atgaaccagc atgtcaataa    840

tgtcacctat attggatggg ttcttgagag catacctcaa gagattgtag acacgcacga    900

acttcaggtc ataactctgg attacagaag agaatgtcaa caagacgatg tggtggattc    960

actcaccact accacctcag agattggtgg gaccaatggc tctgcatcat caggcacaca   1020

ggggcaaaac gatagccagt tcttacatct cttaaggctg tctggagacg gtcaggagat   1080

caaccgcggg acaaccctgt ggagaaagaa gccctccaat ctctaagcca tttcgttctt   1140

aagtttcctc tatctgtgtc gctcgatgct tcacgagtct agtcaggtct catttttttc   1200

aatctaaatt tgggttagac tagagaactg gaattattgg aatttatgag ttttcgttct   1260

tgtttctgta caaatcttga ggattgaagc caaacccatt tcatctt                 1307
```

<210> SEQ ID NO 20
<211> LENGTH: 362
<212> TYPE: PRT
<213> ORGANISM: Brassica campestris

<400> SEQUENCE: 20

```
Met Leu Lys Leu Ser Cys Asn Ala Thr Asp Lys Leu Gln Thr Leu Phe
1               5                   10                  15

Ser His Ser His Gln Pro Asp Pro Ala His Arg Arg Thr Val Ser Ser
            20                  25                  30

Val Ser Cys Ser His Leu Arg Lys Pro Val Leu Asp Pro Leu Arg Ala
        35                  40                  45

Ile Val Ser Ala Asp Gln Gly Ser Val Ile Arg Ala Glu Gln Gly Leu
    50                  55                  60

Gly Ser Leu Ala Asp Gln Leu Arg Leu Gly Ser Leu Thr Glu Asp Gly
65                  70                  75                  80

Leu Ser Tyr Lys Glu Lys Phe Ile Val Arg Ser Tyr Glu Val Gly Ser
                85                  90                  95

Asn Lys Thr Ala Thr Val Glu Thr Val Ala Asn Leu Leu Gln Glu Val
            100                 105                 110

Gly Cys Asn His Ala Gln Ser Val Gly Phe Ser Thr Asp Gly Phe Ala
        115                 120                 125

Thr Thr Pro Thr Met Arg Lys Leu His Leu Ile Trp Val Thr Ala Arg
    130                 135                 140

Met His Ile Glu Ile Tyr Lys Tyr Pro Ala Trp Gly Asp Val Val Glu
145                 150                 155                 160

Ile Glu Thr Trp Cys Gln Ser Glu Gly Arg Ile Gly Thr Arg Arg Asp
                165                 170                 175

Trp Ile Leu Lys Asp Val Ala Thr Gly Glu Val Thr Gly Arg Ala Thr
            180                 185                 190

Ser Lys Trp Val Met Met Asn Gln Asp Thr Arg Arg Leu Gln Lys Val
        195                 200                 205

Ser Asp Asp Val Arg Asp Glu Tyr Leu Val Phe Cys Pro Lys Glu Leu
    210                 215                 220

Arg Leu Ala Phe Pro Glu Glu Asn Asn Arg Ser Leu Lys Lys Ile Pro
225                 230                 235                 240
```

-continued

```
Lys Leu Glu Asp Pro Ala Gln Tyr Ser Met Ile Gly Leu Lys Pro Arg
                245                 250                 255

Arg Ala Asp Leu Asp Met Asn Gln His Val Asn Asn Val Thr Tyr Ile
            260                 265                 270

Gly Trp Val Leu Glu Ser Ile Pro Gln Glu Ile Val Asp Thr His Glu
        275                 280                 285

Leu Gln Val Ile Thr Leu Asp Tyr Arg Arg Glu Cys Gln Gln Asp Asp
    290                 295                 300

Val Val Asp Ser Leu Thr Thr Thr Thr Ser Glu Ile Gly Gly Thr Asn
305                 310                 315                 320

Gly Ser Ala Ser Ser Gly Thr Gln Gly Gln Asn Asp Ser Gln Phe Leu
                325                 330                 335

His Leu Leu Arg Leu Ser Gly Asp Gly Gln Glu Ile Asn Arg Gly Thr
            340                 345                 350

Thr Leu Trp Arg Lys Lys Pro Ser Asn Leu
        355                 360


<210> SEQ ID NO 21
<211> LENGTH: 300
<212> TYPE: DNA
<213> ORGANISM: Cuphea hookeriana
<220> FEATURE:
<221> NAME/KEY: misc_feature
<222> LOCATION: (92)..(93)
<223> OTHER INFORMATION: N= A, T, C or G
<220> FEATURE:
<221> NAME/KEY: misc_feature
<222> LOCATION: (123)..(124)
<223> OTHER INFORMATION: N=A, T, C or G
<220> FEATURE:
<221> NAME/KEY: misc_feature
<222> LOCATION: (135)..(135)
<223> OTHER INFORMATION: N= A, T, C or G

<400> SEQUENCE: 21

cccaaatcga cccccaatgg cggtttgcag gttaaggcaa acgccagcgc ccctcctaag      60

atcaatggtt caccggtcgg tctaaagtcg gnnggtctca agactcagga agacgctcct     120

tcnnccccctc ctccncggac ttttatcaac cagttgcctg attggagtat gcttcttgct    180

gcaatcacta ctgtcttctt ggctgcagag aagcagtgga tgatgcttga ttggaaacca     240

aagaggcctg acatgcttgt ggacccgttc ggattgggaa gtattgttca ggatgggctt     300


<210> SEQ ID NO 22
<211> LENGTH: 581
<212> TYPE: DNA
<213> ORGANISM: Ulma ceae
<220> FEATURE:
<221> NAME/KEY: misc_feature
<222> LOCATION: (137)..(137)
<223> OTHER INFORMATION: N= A, T, C or G
<220> FEATURE:
<221> NAME/KEY: misc_feature
<222> LOCATION: (165)..(167)
<223> OTHER INFORMATION: N= A, T, C or G
<220> FEATURE:
<221> NAME/KEY: misc_feature
<222> LOCATION: (188)..(188)
<223> OTHER INFORMATION: N= A, T, C or G
<220> FEATURE:
<221> NAME/KEY: misc_feature
<222> LOCATION: (192)..(192)
<223> OTHER INFORMATION: N= A, T, C or G
<220> FEATURE:
<221> NAME/KEY: misc_feature
<222> LOCATION: (217)..(217)
<223> OTHER INFORMATION: N= A, T, C or G
```

```
<220> FEATURE:
<221> NAME/KEY: misc_feature
<222> LOCATION: (223)..(223)
<223> OTHER INFORMATION: N= A, T, C or G
<220> FEATURE:
<221> NAME/KEY: misc_feature
<222> LOCATION: (226)..(227)
<223> OTHER INFORMATION: N= A, T, C or G
<220> FEATURE:
<221> NAME/KEY: misc_feature
<222> LOCATION: (256)..(256)
<223> OTHER INFORMATION: N= A, T, C or G
<220> FEATURE:
<221> NAME/KEY: misc_feature
<222> LOCATION: (364)..(364)
<223> OTHER INFORMATION: N= A, T, C or G
<220> FEATURE:
<221> NAME/KEY: misc_feature
<222> LOCATION: (386)..(386)
<223> OTHER INFORMATION: N= A, T, C or G
<220> FEATURE:
<221> NAME/KEY: misc_feature
<222> LOCATION: (545)..(545)
<223> OTHER INFORMATION: N= A, T, C or G

<400> SEQUENCE: 22

ggcacgaggg gctccggtgc ttcaggtgaa ggcaagtccc aagctccacc aaagctcaat     60

ggttccaatg tgggtttggt taaatctagc caaattgtga agaagggtga tgacaccaca    120

tctctcctgc ragmwyncat caaccaattg cctgattgga gcatnnntct tgctgctatc    180

acaacccntg tncttggctg cagagaagca gtggatnatg cwngannttg gaaacccaaa    240

aggcctgaca tgcttnttga tccatttggt cttggaaggt ttgttcagga tggtcttgtt    300

ttccgcaaca acttttcaat tcgatcatat aaataggggc tgatcgaacg gcttctatag    360

aaancgttaa tgaatcatct gcaggnmacr rstcttaatc atgtgaagtc tgttgggctt    420

cttgaggatg gcctaggttc gactcgagag atgtccttga ggaacctgat atgggttgtc    480

actaaaatgc aggttgcggt tgatcgctat ccaacttggg gagatgaagt tctggtatcc    540

tcttngctac tgcaattgga aagaatggaa tcctcgcgaa t                        581


<210> SEQ ID NO 23
<211> LENGTH: 1845
<212> TYPE: DNA
<213> ORGANISM: Ricinus communis

<400> SEQUENCE: 23

ggcttctccc aattcatcgt tgttatcgct accacttccg ccaccacccc accaccatgc     60

aagccctgca gtccccgtct ctccgaccat cccctctaac cccgctccat aaaaatactc    120

acaatgcagc aaaacgccca actaaaaagg tctcctttat caccgcatca tcaacaaata    180

acaacacgac gatttcagct ccaaagcgag agaaagaccc cagaaaaagg gtagtcataa    240

ctggtacggg tttggtatct gtgtttggga atgatgtcga tacttactac gataaattgc    300

ttgctggaga aagtgggatc ggacttattg ataggttcga tgcgtctaag tttcctacta    360

gatttggtgg acagatcagg gggtttaatt cacaaggtta tattgatggg aaaaatgata    420

gaaggcttga tgattgtttg aggtattgca ttgttgctgg taaaaaagct cttgagcatg    480

ctgatcttgg tggtgataag ttgtctaaga ttgataaaga gcgagctggt gtgcttgttg    540

gaacagggat gggtggtctt acagtctttt cagatggtgt tcaggcccta attgaaaaag    600

gacacaggaa aattacccca ttctttattc cttatgctat aacaaacatg ggatctgcct    660

tgttagctat tgaacttggt ctcatgggtc ctaattattc aatttcaact gcttgtgcta    720
```

-continued

```
cctccaatta ttgcttctat gctgctgcca atcatattcg cagaggtgag gctgaattga    780

tgattgctgg tggaactgaa gccgccatca ttccaatcgg tttgggaggt tttgtagcat    840

gtagggcctt atcacaaagg aatgatgatc cacaaactgc ctcaaggcca tgggacaaag    900

atcgagatgg ctttgttatg ggtgaaggtg ctggagtgtt ggtaatggag agtttggaac    960

atgcaatgaa aaggggtgca ccaataattg ctgagtactt gggaggtgct gttaattgtg   1020

atgcttatca catgactgat ccaagggctg atggacttgg ggtctcttcc tgcattgaga   1080

gaagtcttga agatgccggt gtgtcacctg aggaggttaa ctatataaat gcacatgcaa   1140

cttccactct tgctggtgac cttgctgaga taaatgctat taaaaaagta ttcaagaata   1200

cgtctgacat caaaatcaat gcaaccaagt ctatgatagg acattgcctt ggtgctgctg   1260

gaggtctgga agcaattgcc tgtgtgaagg ccattaccac aggatggttg catcctacaa   1320

ttaatcaatt taacccagag ccatcagttg aatttgacac tgttgccaat aagaagcagc   1380

agcacgaagt gaatgttgcc atttcaaatt cctttggatt cggtggacac aactctgtgg   1440

tagccttttc tgcatttaaa ccctgagagc atggccttct tctgcattcg ggccgcggtc   1500

atttacattt accatggcct gcatttcttg taggaaccac tggagagttg cttgcttata   1560

gacagagtca tcgacatcac ttcccccttt tagcttttttg agctgctgat agtagtcagt   1620

ttctcatttc agtatcaagt ctatcttaag aaggtcttgc ttaatttttc ttttcaaatt   1680

accatttcat tgtcattttc cttggaactt ttagcttaag atctgctgtg atcatgtggt   1740

tttgatttca aattaattat gtagcggata cgaacaagca atcataaaaa gtctttttga   1800

attatgtaat tacgataact gttattttct ttttcaaaaa aaaaa                    1845
```

```
<210> SEQ ID NO 24
<211> LENGTH: 487
<212> TYPE: PRT
<213> ORGANISM: Ricinus communis

<400> SEQUENCE: 24

Leu Leu Pro Ile His Arg Cys Tyr Arg Tyr His Phe Arg His His Pro
1               5                   10                  15

Thr Thr Met Gln Ala Leu Gln Ser Pro Ser Leu Arg Pro Ser Pro Leu
            20                  25                  30

Thr Pro Leu His Lys Asn Thr His Asn Ala Ala Lys Arg Pro Thr Lys
        35                  40                  45

Lys Val Ser Phe Ile Thr Ala Ser Ser Thr Asn Asn Asn Thr Thr Ile
    50                  55                  60

Ser Ala Pro Lys Arg Glu Lys Asp Pro Arg Lys Arg Val Val Ile Thr
65                  70                  75                  80

Gly Thr Gly Leu Val Ser Val Phe Gly Asn Asp Val Asp Thr Tyr Tyr
                85                  90                  95

Asp Lys Leu Leu Ala Gly Glu Ser Gly Ile Gly Leu Ile Asp Arg Phe
            100                 105                 110

Asp Ala Ser Lys Phe Pro Thr Arg Phe Gly Gly Gln Ile Arg Gly Phe
        115                 120                 125

Asn Ser Gln Gly Tyr Ile Asp Gly Lys Asn Asp Arg Arg Leu Asp Asp
    130                 135                 140

Cys Leu Arg Tyr Cys Ile Val Ala Gly Lys Lys Ala Leu Glu His Ala
145                 150                 155                 160

Asp Leu Gly Gly Asp Lys Leu Ser Lys Ile Asp Lys Glu Arg Ala Gly
                165                 170                 175
```

-continued

```
Val Leu Val Gly Thr Gly Met Gly Gly Leu Thr Val Phe Ser Asp Gly
            180                 185                 190

Val Gln Ala Leu Ile Glu Lys Gly His Arg Lys Ile Thr Pro Phe Phe
        195                 200                 205

Ile Pro Tyr Ala Ile Thr Asn Met Gly Ser Ala Leu Leu Ala Ile Glu
    210                 215                 220

Leu Gly Leu Met Gly Pro Asn Tyr Ser Ile Ser Thr Ala Cys Ala Thr
225                 230                 235                 240

Ser Asn Tyr Cys Phe Tyr Ala Ala Ala Asn His Ile Arg Arg Gly Glu
                245                 250                 255

Ala Glu Leu Met Ile Ala Gly Gly Thr Glu Ala Ala Ile Ile Pro Ile
            260                 265                 270

Gly Leu Gly Gly Phe Val Ala Cys Arg Ala Leu Ser Gln Arg Asn Asp
        275                 280                 285

Asp Pro Gln Thr Ala Ser Arg Pro Trp Asp Lys Asp Arg Asp Gly Phe
    290                 295                 300

Val Met Gly Glu Gly Ala Gly Val Leu Val Met Glu Ser Leu Glu His
305                 310                 315                 320

Ala Met Lys Arg Gly Ala Pro Ile Ile Ala Glu Tyr Leu Gly Gly Ala
                325                 330                 335

Val Asn Cys Asp Ala Tyr His Met Thr Asp Pro Arg Ala Asp Gly Leu
            340                 345                 350

Gly Val Ser Ser Cys Ile Glu Arg Ser Leu Glu Asp Ala Gly Val Ser
        355                 360                 365

Pro Glu Glu Val Asn Tyr Ile Asn Ala His Ala Thr Ser Thr Leu Ala
    370                 375                 380

Gly Asp Leu Ala Glu Ile Asn Ala Ile Lys Lys Val Phe Lys Asn Thr
385                 390                 395                 400

Ser Asp Ile Lys Ile Asn Ala Thr Lys Ser Met Ile Gly His Cys Leu
                405                 410                 415

Gly Ala Ala Gly Gly Leu Glu Ala Ile Ala Cys Val Lys Ala Ile Thr
            420                 425                 430

Thr Gly Trp Leu His Pro Thr Ile Asn Gln Phe Asn Pro Glu Pro Ser
        435                 440                 445

Val Glu Phe Asp Thr Val Ala Asn Lys Lys Gln Gln His Glu Val Asn
    450                 455                 460

Val Ala Ile Ser Asn Ser Phe Gly Phe Gly Gly His Asn Ser Val Val
465                 470                 475                 480

Ala Phe Ser Ala Phe Lys Pro
                485


<210> SEQ ID NO 25
<211> LENGTH: 1969
<212> TYPE: DNA
<213> ORGANISM: Ricinus communis

<400> SEQUENCE: 25

ccccgtggcg gcgtgcatgt cggtcacgtg ctcaaaggag aacagacacg cgttcttctc      60

ttcatcgaca ccgggcacca ccagcagtca cagtcgtaca agaaggaggc ctaaatataa     120

tagtatcagc acccctgcct ctcaatcttt ctttaattct ttatcatctt ctggatcgag     180

ttttcaacaa ttaatgtctt cttgcttggc cttcgagcct tgtagtcatt actacagctc     240

taatggcctc tttcctaaca ctcctcttct tcctaagcgc catcctagac ttcatcatcg     300

ccttcctcgt tctggggaag caatggcagt ggctgtgcaa cctgaaaagg aggttgcaac     360
```

```
aaataagaaa cctcttatga agcaaaggag agtagttgtt actgggatgg gtgttgtttc    420
accccttggt catgatatag acgtctatta caataatctt cttgacggtt ctagtggtat    480
tagtcagatt gattcctttg actgtgccca atttcctacg aggattgctg gagagatcaa    540
gtctttctca actgatggat gggttgcacc aaaactttcc aagagaatgg ataaattcat    600
gctttacatg cttactgctg gcaaaaaagc cttggcagat ggtggtatta cagaggatat    660
gatggatgaa ttggataaag ctagatgtgg agttttaatt ggttctgcaa tgggtggcat    720
gaaggttttc aatgatgcaa ttgaagcatt aaggatctcg tataggaaga tgaatccttt    780
ctgcgtacct tttgcgacta caaatatggg ctctgccatg cttgcaatgg accttggttg    840
gatggggcca aactattcaa tatctactgc ttgtgctact agcaattttt gtatattgaa    900
tgccgcaaac cacatcatta gaggcgaagc tgatattatg ctttgtggtg gctcagatgc    960
agcaattata cctattggct tgggaggttt tgtggcatgc agagcgctct cacagaggaa   1020
tgatgatcct acaaaagctt cacgaccttg ggatatgaat cgggatggat ttgtgatggg   1080
ggaaggagct ggtgttcttc ttttagaaga actagaacat gctaagaaaa gaggtgcaaa   1140
tatttatgcg gaatttcttg gaggaagctt tacatgtgat gcttatcaca tgactgaacc   1200
gcgtccagat ggagttggtg tcattctctg tatagaaaag gcattagcgc gatctggtgt   1260
atccaaggag gaagtaaact acataaatgc acatgctacg tctaccccag ctggagacct   1320
taaagaatat gaagctctta tgcgctgttt cagccaaaat cctgatttga gagtgaactc   1380
tacgaagtct atgattggcc atttactagg agcagctggt gctgtggaag ctatagcaac   1440
aatacaggcg atacggacag gatgggttca tccaaacatc aacctggaaa acccagaaga   1500
aggcgtggac acaaaggtgc tggttggccc aaagaaggag agattggaca ttaaggttgc   1560
tctgtccaac tcttttgggt tcggtgggca caactcatcg atcattttttg ctccgtacaa   1620
gtgaaataag ggtacttca actttggtgt attaacgtga aagatgatct aaaatggaac   1680
aagattagat aactctatgg gtagggaaag gagaatatgc cgagttcaca gagaggaaac   1740
ttcccgtgaa gattcctgtg ccttctacca ttttcagtat tctctccgca tcattgtggc   1800
ttgatccatg ttgatccatc gaataccagt aacagtggcc ttatttaatt tttgttccat   1860
gtataagcag acggctgatc gttgctttaa cagtcaattg taatgaattt ttgagctgga   1920
cagttggcta ggttacacta atgtaatggt ggttttatga gcaaaaaaa               1969
```

<210> SEQ ID NO 26
<211> LENGTH: 540
<212> TYPE: PRT
<213> ORGANISM: Ricinus communis

<400> SEQUENCE: 26

```
Pro Val Ala Ala Cys Met Ser Val Thr Cys Ser Lys Glu Asn Arg His
1               5                   10                  15

Ala Phe Phe Ser Ser Ser Thr Pro Gly Thr Thr Ser Ser His Ser Arg
            20                  25                  30

Thr Arg Arg Arg Pro Lys Tyr Asn Ser Ile Ser Thr Pro Ala Ser Gln
        35                  40                  45

Ser Phe Phe Asn Ser Leu Ser Ser Ser Gly Ser Ser Phe Gln Gln Leu
    50                  55                  60

Met Ser Ser Cys Leu Ala Phe Glu Pro Cys Ser His Tyr Tyr Ser Ser
65                  70                  75                  80

Asn Gly Leu Phe Pro Asn Thr Pro Leu Leu Pro Lys Arg His Pro Arg
```

-continued

```
                85                  90                  95

Leu His His Arg Leu Pro Arg Ser Gly Glu Ala Met Ala Val Ala Val
            100                 105                 110

Gln Pro Glu Lys Glu Val Ala Thr Asn Lys Lys Pro Leu Met Lys Gln
        115                 120                 125

Arg Arg Val Val Val Thr Gly Met Gly Val Val Ser Pro Leu Gly His
    130                 135                 140

Asp Ile Asp Val Tyr Tyr Asn Asn Leu Leu Asp Gly Ser Ser Gly Ile
145                 150                 155                 160

Ser Gln Ile Asp Ser Phe Asp Cys Ala Gln Phe Pro Thr Arg Ile Ala
                165                 170                 175

Gly Glu Ile Lys Ser Phe Ser Thr Asp Gly Trp Val Ala Pro Lys Leu
            180                 185                 190

Ser Lys Arg Met Asp Lys Phe Met Leu Tyr Met Leu Thr Ala Gly Lys
        195                 200                 205

Lys Ala Leu Ala Asp Gly Gly Ile Thr Glu Asp Met Met Asp Glu Leu
    210                 215                 220

Asp Lys Ala Arg Cys Gly Val Leu Ile Gly Ser Ala Met Gly Gly Met
225                 230                 235                 240

Lys Val Phe Asn Asp Ala Ile Glu Ala Leu Arg Ile Ser Tyr Arg Lys
                245                 250                 255

Met Asn Pro Phe Cys Val Pro Phe Ala Thr Thr Asn Met Gly Ser Ala
            260                 265                 270

Met Leu Ala Met Asp Leu Gly Trp Met Gly Pro Asn Tyr Ser Ile Ser
        275                 280                 285

Thr Ala Cys Ala Thr Ser Asn Phe Cys Ile Leu Asn Ala Ala Asn His
    290                 295                 300

Ile Ile Arg Gly Glu Ala Asp Ile Met Leu Cys Gly Gly Ser Asp Ala
305                 310                 315                 320

Ala Ile Ile Pro Ile Gly Leu Gly Gly Phe Val Ala Cys Arg Ala Leu
                325                 330                 335

Ser Gln Arg Asn Asp Asp Pro Thr Lys Ala Ser Arg Pro Trp Asp Met
            340                 345                 350

Asn Arg Asp Gly Phe Val Met Gly Glu Gly Ala Gly Val Leu Leu Leu
        355                 360                 365

Glu Glu Leu Glu His Ala Lys Lys Arg Gly Ala Asn Ile Tyr Ala Glu
    370                 375                 380

Phe Leu Gly Gly Ser Phe Thr Cys Asp Ala Tyr His Met Thr Glu Pro
385                 390                 395                 400

Arg Pro Asp Gly Val Gly Val Ile Leu Cys Ile Glu Lys Ala Leu Ala
                405                 410                 415

Arg Ser Gly Val Ser Lys Glu Glu Val Asn Tyr Ile Asn Ala His Ala
            420                 425                 430

Thr Ser Thr Pro Ala Gly Asp Leu Lys Glu Tyr Glu Ala Leu Met Arg
        435                 440                 445

Cys Phe Ser Gln Asn Pro Asp Leu Arg Val Asn Ser Thr Lys Ser Met
    450                 455                 460

Ile Gly His Leu Leu Gly Ala Ala Gly Ala Val Glu Ala Ile Ala Thr
465                 470                 475                 480

Ile Gln Ala Ile Arg Thr Gly Trp Val His Pro Asn Ile Asn Leu Glu
                485                 490                 495

Asn Pro Glu Glu Gly Val Asp Thr Lys Val Leu Val Gly Pro Lys Lys
            500                 505                 510
```

```
Glu Arg Leu Asp Ile Lys Val Ala Leu Ser Asn Ser Phe Gly Phe Gly
        515                 520                 525

Gly His Asn Ser Ser Ile Ile Phe Ala Pro Tyr Lys
    530                 535                 540


<210> SEQ ID NO 27
<211> LENGTH: 39
<212> TYPE: DNA
<213> ORGANISM: Artificial Sequence
<220> FEATURE:
<223> OTHER INFORMATION: PCR Primer for Brassica rapa sequence

<400> SEQUENCE: 27

cttaagaagt aacccgggct gcagttttag tattaagag                          39


<210> SEQ ID NO 28
<211> LENGTH: 48
<212> TYPE: DNA
<213> ORGANISM: Artificial Sequence
<220> FEATURE:
<223> OTHER INFORMATION: PCR Primer for Brassica rapa

<400> SEQUENCE: 28

ccatttttga tcttcctcga gcccgggctg cagttcttct tcttcttg                48


<210> SEQ ID NO 29
<211> LENGTH: 48
<212> TYPE: DNA
<213> ORGANISM: Artificial Sequence
<220> FEATURE:
<223> OTHER INFORMATION: PCR Primer for Brassica rapa

<400> SEQUENCE: 29

gctcgttttt tttttctctg cagcccgggc tcgagtcaca gcttcacc                48


<210> SEQ ID NO 30
<211> LENGTH: 44
<212> TYPE: DNA
<213> ORGANISM: Artificial Sequence
<220> FEATURE:
<223> OTHER INFORMATION: PCR Primer for Brassica rapa

<400> SEQUENCE: 30

actgactgca gcccgggctc gaggaagatc aaaaatggct cttc                    44


<210> SEQ ID NO 31
<211> LENGTH: 43
<212> TYPE: DNA
<213> ORGANISM: Artificial Sequence
<220> FEATURE:
<223> OTHER INFORMATION: PCR Primer for Brassica rapa

<400> SEQUENCE: 31

gagtagtgaa cttcatggat cctcgaggtc ttgaaaacct aga                     43


<210> SEQ ID NO 32
<211> LENGTH: 44
<212> TYPE: DNA
<213> ORGANISM: Artificial Sequence
<220> FEATURE:
<223> OTHER INFORMATION: PCR Primer for Brassica rapa

<400> SEQUENCE: 32

caatgtcttg agagatcccg ggatccttaa caactaggaa aagg                    44
```

<210> SEQ ID NO 33
<211> LENGTH: 24
<212> TYPE: DNA
<213> ORGANISM: Artificial Sequence
<220> FEATURE:
<223> OTHER INFORMATION: PCR Primer for Bluescript ks+

<400> SEQUENCE: 33
gtaagacacg acttatcgcc actg 24

<210> SEQ ID NO 34
<211> LENGTH: 43
<212> TYPE: DNA
<213> ORGANISM: Artificial Sequence
<220> FEATURE:
<223> OTHER INFORMATION: PCR Primer for Brassica campestris

<400> SEQUENCE: 34
ggaattcgtc gacagatctc tgcagctcga gggatccaag ctt 43

<210> SEQ ID NO 35
<211> LENGTH: 32
<212> TYPE: DNA
<213> ORGANISM: Artificial Sequence
<220> FEATURE:
<223> OTHER INFORMATION: PCR Primer for Brassica campestris

<400> SEQUENCE: 35
gcttgttcgc catgcatatc ttctgtatgt tc 32

<210> SEQ ID NO 36
<211> LENGTH: 1573
<212> TYPE: DNA
<213> ORGANISM: Brassica campestris

<400> SEQUENCE: 36
atgcgagaca gcccacgaga agacgctcat tcatctccgc gtcgtcctcc gccgtctccg 60
cccccaaacg cgaaacagac ccgaagaaac gggtcgtaat caccggaatg ggcctcgtct 120
ccgtcttcgg aaacgacgtc gacgcttact acgagaagct gctctccggc gagagtggaa 180
tcagcttgat tgatcggttc gacgcctcca agttcccgac ccgattcggt ggacagatcc 240
gtgggttcag ctcagagggt tacatcgatg ggaagaatga gcggaggctt gatgattgct 300
tgaagtactg cattgtcgct gggaagaagg ctcttgaaag tgcgaatctt ggtggtgata 360
agcttaacac gattgataag cagaaagctg gagtactagt tgggactggt atgggtggct 420
tgactgtgtt ttcagacggt gttcaagctc ttattgagaa aggtcacagg aggatttctc 480
ctttctttat tccttatgct attacaaaca tgggttctgc tttgttggcg attgatcttg 540
gtcttatggg tcctaactac tcgatctcga cggcttgtgc cacttctaac tactgctttt 600
acgctgctgc gaatcacatt cgacgtggtg aagctgatat gatgatagct ggtggaaccg 660
aggctgctat tattcctatt ggtttgggag gttttgttgc ttgtagggcg ctttcacaga 720
gaaatgatga tcctcagacg gcttcaaggc cgtgggataa acagagagat gggtttgtca 780
tgggtgaagg agctggtgtt ctggtgatgg aaagcttgga acatgcgatg aaacgtggtg 840
ctccaattgt agcagagtat cttggaggcg ctgttaactg cgatgctcat catatgactg 900
atccaagagc tgatgggctt ggtgtgtctt catgcattga gagctgcctt gaagatgctg 960
gtgtatcacc tgaggaggta aattacatca atgcacatgc aacttccaca ctggctggtg 1020
atcttgctga gattaatgcc attaaaaagg tattcaaaag cacttcaggg atcaaaatca 1080

-continued atgccaccaa gtctatgata ggtcactgcc tcggtgcagc tggaggtctt gaagccattg 1140
ccaccgtgaa ggctatcaac acgggatggc tgcatccctc tatcaaccaa tttaacccag 1200
aaccagcagt ggactttgat acggtcgcaa acgagaagaa gcagcatgag gtgaatgttg 1260
ccatatcaaa ctcgtttggg ttcggtggac ataactcagt ggtcgctttc tctgccttca 1320
aaccctgatt tcctcagacc ctttagatcc tctggtccat ctgttagatc accaccatca 1380
tcttcttcgc agcttcttgg ttcacaagtt gagcgctttc ttcctttcag ctttttgttc 1440
ttattggtca ttgttaattt ttgctcaact cttattggtc attgaggtgt agagaatcca 1500
gattttgctt ctacaatctg tgtacggaat gttgtatctt tagttcgttt tatgtttgcc 1560
aaattttata aac 1573

<210> SEQ ID NO 37
<211> LENGTH: 441
<212> TYPE: PRT
<213> ORGANISM: Brassica campestris

<400> SEQUENCE: 37

Ala Arg Gln Pro Thr Arg Arg Arg Ser Phe Ile Ser Ala Ser Ser Ser
1 5 10 15

Ala Val Ser Ala Pro Lys Arg Glu Thr Asp Pro Lys Lys Arg Val Val
20 25 30

Ile Thr Gly Met Gly Leu Val Ser Val Phe Gly Asn Asp Val Asp Ala
35 40 45

Tyr Tyr Glu Lys Leu Leu Ser Gly Glu Ser Gly Ile Ser Leu Ile Asp
50 55 60

Arg Phe Asp Ala Ser Lys Phe Pro Thr Arg Phe Gly Gly Gln Ile Arg
65 70 75 80

Gly Phe Ser Ser Glu Gly Tyr Ile Asp Gly Lys Asn Glu Arg Arg Leu
85 90 95

Asp Asp Cys Leu Lys Tyr Cys Ile Val Ala Gly Lys Lys Ala Leu Glu
100 105 110

Ser Ala Asn Leu Gly Gly Asp Lys Leu Asn Thr Ile Asp Lys Gln Lys
115 120 125

Ala Gly Val Leu Val Gly Thr Gly Met Gly Gly Leu Thr Val Phe Ser
130 135 140

Asp Gly Val Gln Ala Leu Ile Glu Lys Gly His Arg Arg Ile Ser Pro
145 150 155 160

Phe Phe Ile Pro Tyr Ala Ile Thr Asn Met Gly Ser Ala Leu Leu Ala
165 170 175

Ile Asp Leu Gly Leu Met Gly Pro Asn Tyr Ser Ile Ser Thr Ala Cys
180 185 190

Ala Thr Ser Asn Tyr Cys Phe Tyr Ala Ala Ala Asn His Ile Arg Arg
195 200 205

Gly Glu Ala Asp Met Met Ile Ala Gly Gly Thr Glu Ala Ala Ile Ile
210 215 220

Pro Ile Gly Leu Gly Gly Phe Val Ala Cys Arg Ala Leu Ser Gln Arg
225 230 235 240

Asn Asp Asp Pro Gln Thr Ala Ser Arg Pro Trp Asp Lys Gln Arg Asp
245 250 255

Gly Phe Val Met Gly Glu Gly Ala Gly Val Leu Val Met Glu Ser Leu
260 265 270

Glu His Ala Met Lys Arg Gly Ala Pro Ile Val Ala Glu Tyr Leu Gly

```
        275                 280                 285

Gly Ala Val Asn Cys Asp Ala His His Met Thr Asp Pro Arg Ala Asp
    290                 295                 300

Gly Leu Gly Val Ser Ser Cys Ile Glu Ser Cys Leu Glu Asp Ala Gly
305                 310                 315                 320

Val Ser Pro Glu Glu Val Asn Tyr Ile Asn Ala His Ala Thr Ser Thr
                325                 330                 335

Leu Ala Gly Asp Leu Ala Glu Ile Asn Ala Ile Lys Lys Val Phe Lys
            340                 345                 350

Ser Thr Ser Gly Ile Lys Ile Asn Ala Thr Lys Ser Met Ile Gly His
        355                 360                 365

Cys Leu Gly Ala Ala Gly Gly Leu Glu Ala Ile Ala Thr Val Lys Ala
    370                 375                 380

Ile Asn Thr Gly Trp Leu His Pro Ser Ile Asn Gln Phe Asn Pro Glu
385                 390                 395                 400

Pro Ala Val Asp Phe Asp Thr Val Ala Asn Glu Lys Lys Gln His Glu
                405                 410                 415

Val Asn Val Ala Ile Ser Asn Ser Phe Gly Phe Gly Gly His Asn Ser
            420                 425                 430

Val Val Ala Phe Ser Ala Phe Lys Pro
        435                 440


<210> SEQ ID NO 38
<211> LENGTH: 1922
<212> TYPE: DNA
<213> ORGANISM: Brassica campestris

<400> SEQUENCE: 38

ccccccgacg cgtccaaaca ctcaagtgtg agagagagat cagataatct ttctcgtttt      60

ctccaccttc atccgagtat gacgatgggt ggtgcgtctt tatgcgattc actagtggct     120

gcttgcatgt cctccgcctc gcactcaagc ggagaccgac tgactcaatt catctggcct     180

cgccggagta gactggttaa caactgctcg ctccatggat cccaggcgag ttcccgtaac     240

aacaatgcct cgtcttccct cttcgaatcg aataacactt ccttcaatcc aaagcagagg     300

agattcaatc gagcatcaac ctctgggcaa gtcactacac tagagatgga gaaggacgca     360

atggtaaaca agccacgccg agttgttgtc actggcatgg gagttgaaac accactaggt     420

cacgaccctc atacttttta tgacaacttg ctacaaggca aaagtggtat aagccatata     480

gagagtttcg actgttctgc atttcccact agaatcgctg ggagagattaa atctttttcg     540

accgacggat tggttgctcc taaactttcc aaaaggatgg acaagttcat gctctacctt     600

ctaaccgccg gcaagaaggc gttggaggat ggtggggtga ctggggatgt gatggcagag     660

ttcgacaaat caagatgtgg tgtcttgatt ggctcagcaa tgggaggcat gaaggtcttt     720

tacgatgcgc ttgaagcttt gaaaatctct tacaggaaga tgaacccttt ttgtgtacct     780

tttgccacca caaacatggg ttccgctatg cttgccttgg atctgggatg gatgggtcca     840

aactactcta tttcaaccgc atgtgccacg ggaaacttct gtattctcaa tgcggcaaac     900

cacattacca gaggtgaagc tgatgtaatg ctctgtggtg gctctgactc agttattatt     960

ccaatagggt tgggaggttt tgttgcctgc cgggctcttt cagaaaataa tgatgatccc    1020

accaaagctt ctcgtccttg ggatagtaac cgagatggtt ttgttatggg agagggagcc    1080

ggagttctac ttttagaaga acttgagcat gccaagagga gcaactatat acgcagagtt    1140

ccttgggggt agtttcacat gtgatgcata ccatataacc gaaccacgtc ctgatggtgc    1200
```

```
tggtgtcatt cttgctatcg agaaagcggt agctcatgcc gggatttcta aggaagacat   1260

aaattacgtg aatgctcatg ctacctctac accagctgga gaccttaagg agtaccacgc   1320

tctttctcac tgttttggcc aaaatcctga gctaagagta aactcaacaa aatctatgat   1380

tggacacttg ctgggagctt ctggggccgt ggaggctgtt gcaaccgttc aggcaataaa   1440

gacaggatgg gttcatccaa atatcaacct cgagaatcca gacaaagcag tggatacaaa   1500

gcttttggtg ggtcttaaga aggagagact ggatatcaaa gcagccttgt caaactcttt   1560

cggctttggt ggccagaact ctagcataat tttcgctcct tacaaatgaa aggcgaatag   1620

tccaatgctg tgtactcttg tgtaacttgc tgtaagtgtg tacaagaact tcccatgttt   1680

tgatgcaata tgtacgagaa cttcccatgc ttttggtagt gccatgattc aggattcgat   1740

taacttgcac aaagagttta agcaacgttg aaaagagaga gaaaaaaaaa gtgatgaggt   1800

agctgaggat ttgtcaggaa caacaatact tcatttttca ctttggttag gtagactgaa   1860

atatttgagc caacatttct tgtattttta ttctttgaaa gctttaacca aagaaaaaaa   1920

aa                                                                  1922
```

```
<210> SEQ ID NO 39
<211> LENGTH: 1786
<212> TYPE: DNA
<213> ORGANISM: Simmondsia chinensis
<220> FEATURE:
<221> NAME/KEY: misc_feature
<222> LOCATION: (1537)..(1537)
<223> OTHER INFORMATION: N=A, T, C or G
<220> FEATURE:
<221> NAME/KEY: misc_feature
<222> LOCATION: (1608)..(1609)
<223> OTHER INFORMATION: N= A, T, C or G

<400> SEQUENCE: 39

aaatcctcca ctcatacact ccacttctct ctctctctct ctctctctga aacaatttga     60

gtagcaaact taaaagaaaa tggaggaaat gggaagcatt ttagagtttc ttgataacaa    120

agccattttg gtcactggtg ctactggctc cttagcaaaa atttttgtgg agaaggtact    180

gaggagtcaa ccgaatgtga agaaactcta tcttcttttg agagcaaccg atgacgagac    240

agctgctcta cgcttgcaaa atgaggtttt tggaaaagag ttgttcaaag ttctgaaaca    300

aaatttaggt gcaaatttct attcctttgt atcagaaaaa gtgactgtag tacccggtga    360

tattactggt gaagacttgt gtctcaaaga cgtcaatttg aaggaagaaa tgtggaggga    420

aatcgatgtt gttgtcaatc tagctgctac aatcaacttc attgaaaggt acgacgtgtc    480

tctgcttatc aacacatatg gagccaagta tgttttggac ttcgcgaaga agtgcaacaa    540

attaaagata tttgttcatg tatctactgc ttatgtatct ggagagaaaa atgggttaat    600

actggagaag ccttattata tgggcgagtc acttaatgga agattaggtc tggacattaa    660

tgtagagaag aaacttgtgg aggcaaaaat caatgaactt caagcagcgg gggcaacgga    720

aaagtccatt aaatcgacaa tgaaggacat gggcatcgag agggcaagac actggggatg    780

gccaaatgtg tatgtattca ccaaggcatt aggggagatg cttttgatgc aatacaaagg    840

ggacattccg cttactatta ttcgtcccac catcatcacc agcactttta aagagccctt    900

tcctggttgg gttgaaggtg tcaggaccat cgataatgta cctgtatatt atggtaaagg    960

gagattgagg tgtatgcttt gcggacccag cacaataatt gacctgatac cggcagatat   1020

ggtcgtgaat gcaacgatag tagccatggt ggcgcacgca aaccaaagat acgtagagcc   1080
```

-continued

```
ggtgacatac catgtgggat cttcagcggc gaatccaatg aaactgagtg cattaccaga   1140

gatggcacac cgttacttca ccaagaatcc atggatcaac ccggatcgca acccagtaca   1200

tgtgggtcgg gctatggtct tctcctcctt ctccaccttc cacctttatc tcacccttaa   1260

tttcctcctt cctttgaagg tactggagat agcaaataca atattctgcc aatggttcaa   1320

gggtaagtac atggatctta aaaggaagac gaggttgttg ttgcgtttag tagacattta   1380

taaaccctac ctcttcttcc aaggcatctt tgatgacatg aacactgaga agttgcggat   1440

tgctgcaaaa gaaagcatag ttgaagctga tatgttttac tttgatccca gggcaattaa   1500

ctgggaagat tacttcttga aaactcattt cccaggngtc gtagagcacg ttcttaacta   1560

aaagttacgg tacgaaaatg agaagattgg aatgcatgca ccgaaagnnc aacataaaag   1620

acgtggttaa agtcatggtc aaaaaagaaa taaaatgcag ttaggtttgt gttgcagttt   1680

tgattccttg tattgttact tgtacttttg atctttttct tttttaatga aatttctctc   1740

tttgttttgt gaaaaaaaaa aaaaaaaaga gctcctgcag aagctt                  1786
```

```
<210> SEQ ID NO 40
<211> LENGTH: 493
<212> TYPE: PRT
<213> ORGANISM: Simmondsia chinensis

<400> SEQUENCE: 40

Met Glu Glu Met Gly Ser Ile Leu Glu Phe Leu Asp Asn Lys Ala Ile
1               5                   10                  15

Leu Val Thr Gly Ala Thr Gly Ser Leu Ala Lys Ile Phe Val Glu Lys
            20                  25                  30

Val Leu Arg Ser Gln Pro Asn Val Lys Lys Leu Tyr Leu Leu Leu Arg
        35                  40                  45

Ala Thr Asp Asp Glu Thr Ala Ala Leu Arg Leu Gln Asn Glu Val Phe
    50                  55                  60

Gly Lys Glu Leu Phe Lys Val Leu Lys Gln Asn Leu Gly Ala Asn Phe
65                  70                  75                  80

Tyr Ser Phe Val Ser Glu Lys Val Thr Val Val Pro Gly Asp Ile Thr
                85                  90                  95

Gly Glu Asp Leu Cys Leu Lys Asp Val Asn Leu Lys Glu Glu Met Trp
            100                 105                 110

Arg Glu Ile Asp Val Val Val Asn Leu Ala Ala Thr Ile Asn Phe Ile
        115                 120                 125

Glu Arg Tyr Asp Val Ser Leu Leu Ile Asn Thr Tyr Gly Ala Lys Tyr
    130                 135                 140

Val Leu Asp Phe Ala Lys Lys Cys Asn Lys Leu Lys Ile Phe Val His
145                 150                 155                 160

Val Ser Thr Ala Tyr Val Ser Gly Glu Lys Asn Gly Leu Ile Leu Glu
                165                 170                 175

Lys Pro Tyr Tyr Met Gly Glu Ser Leu Asn Gly Arg Leu Gly Leu Asp
            180                 185                 190

Ile Asn Val Glu Lys Lys Leu Val Glu Ala Lys Ile Asn Glu Leu Gln
        195                 200                 205

Ala Ala Gly Ala Thr Glu Lys Ser Ile Lys Ser Thr Met Lys Asp Met
    210                 215                 220

Gly Ile Glu Arg Ala Arg His Trp Gly Trp Pro Asn Val Tyr Val Phe
225                 230                 235                 240

Thr Lys Ala Leu Gly Glu Met Leu Leu Met Gln Tyr Lys Gly Asp Ile
                245                 250                 255
```

-continued

```
Pro Leu Thr Ile Ile Arg Pro Thr Ile Ile Thr Ser Thr Phe Lys Glu
            260                 265                 270

Pro Phe Pro Gly Trp Val Glu Gly Val Arg Thr Ile Asp Asn Val Pro
        275                 280                 285

Val Tyr Tyr Gly Lys Gly Arg Leu Arg Cys Met Leu Cys Gly Pro Ser
    290                 295                 300

Thr Ile Ile Asp Leu Ile Pro Ala Asp Met Val Val Asn Ala Thr Ile
305                 310                 315                 320

Val Ala Met Val Ala His Ala Asn Gln Arg Tyr Val Glu Pro Val Thr
                325                 330                 335

Tyr His Val Gly Ser Ser Ala Ala Asn Pro Met Lys Leu Ser Ala Leu
            340                 345                 350

Pro Glu Met Ala His Arg Tyr Phe Thr Lys Asn Pro Trp Ile Asn Pro
        355                 360                 365

Asp Arg Asn Pro Val His Val Gly Arg Ala Met Val Phe Ser Ser Phe
    370                 375                 380

Ser Thr Phe His Leu Tyr Leu Thr Leu Asn Phe Leu Leu Pro Leu Lys
385                 390                 395                 400

Val Leu Glu Ile Ala Asn Thr Ile Phe Cys Gln Trp Phe Lys Gly Lys
                405                 410                 415

Tyr Met Asp Leu Lys Arg Lys Thr Arg Leu Leu Leu Arg Leu Val Asp
            420                 425                 430

Ile Tyr Lys Pro Tyr Leu Phe Phe Gln Gly Ile Phe Asp Asp Met Asn
        435                 440                 445

Thr Glu Lys Leu Arg Ile Ala Ala Lys Glu Ser Ile Val Glu Ala Asp
    450                 455                 460

Met Phe Tyr Phe Asp Pro Arg Ala Ile Asn Trp Glu Asp Tyr Phe Leu
465                 470                 475                 480

Lys Thr His Phe Pro Gly Val Val Glu His Val Leu Asn
                485                 490


<210> SEQ ID NO 41
<211> LENGTH: 1733
<212> TYPE: DNA
<213> ORGANISM: Simmondsia chinensis
<220> FEATURE:
<221> NAME/KEY: misc_feature
<222> LOCATION: (676)..(676)
<223> OTHER INFORMATION: N= A, T, C or G
<220> FEATURE:
<221> NAME/KEY: misc_feature
<222> LOCATION: (737)..(737)
<223> OTHER INFORMATION: N= A, T, C or G

<400> SEQUENCE: 41

ggaactccat cccttcctcc ctcactcctc tctctacaat gaaggccaaa acaatcacaa     60

acccggagat ccaagtctcc acgaccatga ccaccacgac cacgactatg accgccactc    120

tccccaactt caagtcctcc atcaacttac accacgtcaa gctcggctac cactacttaa    180

tctccaatgc cctcttcctc gtattcatcc ccctttttggg cctcgcttcg gcccatctct    240

cctccttctc ggcccatgac ttgtccctgc tcttcgacct ccttcgccgc aacctcctcc    300

ctgttgtcgt ttgttctttc ctcttcgttt tattagcaac cctacatttc ttgacccggc    360

ccaggaatgt ctacttggtg gactttggat gctataagcc tcaaccgaac ctgatgacat    420

cccacgagat gttcatggac cggacctccc gggccgggtc gttttctaag gagaatattg    480

agtttcagag gaagatcttg gagagggccg gtatgggtcg ggaaacctat gtccccgaat    540
```

```
ccgtcactaa ggtgcccgcc gagccgagca tagcagcagc cagggccgag gcggaggagg    600
tgatgtacgg ggcgatcgac gaggtgttgg agaagacggg ggtgaagccg aagcagatag    660
gaatactggt ggtganctgc agcttgttta acccaacgcc gtcgctgtca tccatgatag    720
ttaaccatta caagctnagg ggtaatatac ttagctataa tcttggtggc atgggttgca    780
gtgctgggct catttccatt gatcttgcca aggacctcct acaggtttac cgtaaaaaca    840
catatgtgtt agtagtgagc acggaaaaca tgacccttaa ttggtactgg ggcaatgacc    900
gctccatgct tatcaccaac tgcctatttc gcatgggtgg cgctgccatc atcctctcaa    960
accgctggcg tgatcgtcgc cgatccaagt accaactcct tcatacagta cgcacccaca   1020
agggcgctga cgacaagtcc tatagatgcg tcttacaaca agaagatgaa aataacaagg   1080
taggtgttgc cttatccaag gatctgatgg cagttgccgg tgaagcccta aaggccaaca   1140
tcacgaccct tggtcccctc gtgctcccca tgtcagaaca actcctcttc tttgccacct   1200
tagtggcacg taaggtcttc aagatgacga acgtgaagcc atacatccca gatttcaagt   1260
tggcagcgaa cgacttctgc atccatgcag gaggcaaagc agtgttggat gagctcgaga   1320
agaacttgga gttgacgcca tggcaccttg aaccctcgag gatgacactg tataggtttg   1380
ggaacacatc gagtagctca ttatggtacg agttggcata cgctgaagca aaagggagga   1440
tccgtaaggg tgatcgaact tggatgattg gatttggttc aggtttcaag tgtaacagtg   1500
ttgtgtggag ggctttgagg agtgtcaatc cggctagaga gaagaatcct tggatggatg   1560
aaattgagaa gttccctgtc catgtgccta aaatcgcacc tatcgcttcg tagaactgct   1620
aggatgtgat tagtaatgaa aaatgtgtat tatgttagtg atgtagaaaa agaaacttta   1680
gttgatgggt gagaacatgt ctcattgaga ataacgtgtg catcgttgtg ttg          1733
```

<210> SEQ ID NO 42
<211> LENGTH: 524
<212> TYPE: PRT
<213> ORGANISM: Simmondsia chinensis
<220> FEATURE:
<221> NAME/KEY: MISC_FEATURE
<222> LOCATION: (213)..(213)
<223> OTHER INFORMATION: Xaa= any amino acid

<400> SEQUENCE: 42

```
Met Lys Ala Lys Thr Ile Thr Asn Pro Glu Ile Gln Val Ser Thr Thr
1               5                   10                  15

Met Thr Thr Thr Thr Thr Thr Met Thr Ala Thr Leu Pro Asn Phe Lys
            20                  25                  30

Ser Ser Ile Asn Leu His His Val Lys Leu Gly Tyr His Tyr Leu Ile
        35                  40                  45

Ser Asn Ala Leu Phe Leu Val Phe Ile Pro Leu Leu Gly Leu Ala Ser
    50                  55                  60

Ala His Leu Ser Ser Phe Ser Ala His Asp Leu Ser Leu Leu Phe Asp
65                  70                  75                  80

Leu Leu Arg Arg Asn Leu Leu Pro Val Val Val Cys Ser Phe Leu Phe
                85                  90                  95

Val Leu Leu Ala Thr Leu His Phe Leu Thr Arg Pro Arg Asn Val Tyr
            100                 105                 110

Leu Val Asp Phe Gly Cys Tyr Lys Pro Gln Pro Asn Leu Met Thr Ser
        115                 120                 125

His Glu Met Phe Met Asp Arg Thr Ser Arg Ala Gly Ser Phe Ser Lys
    130                 135                 140
```

-continued

```
Glu Asn Ile Glu Phe Gln Arg Lys Ile Leu Glu Arg Ala Gly Met Gly
145                 150                 155                 160

Arg Glu Thr Tyr Val Pro Glu Ser Val Thr Lys Val Pro Ala Glu Pro
                165                 170                 175

Ser Ile Ala Ala Ala Arg Ala Glu Ala Glu Glu Val Met Tyr Gly Ala
            180                 185                 190

Ile Asp Glu Val Leu Glu Lys Thr Gly Val Lys Pro Lys Gln Ile Gly
        195                 200                 205

Ile Leu Val Val Xaa Cys Ser Leu Phe Asn Pro Thr Pro Ser Leu Ser
    210                 215                 220

Ser Met Ile Val Asn His Tyr Lys Leu Arg Gly Asn Ile Leu Ser Tyr
225                 230                 235                 240

Asn Leu Gly Gly Met Gly Cys Ser Ala Gly Leu Ile Ser Ile Asp Leu
                245                 250                 255

Ala Lys Asp Leu Leu Gln Val Tyr Arg Lys Asn Thr Tyr Val Leu Val
            260                 265                 270

Val Ser Thr Glu Asn Met Thr Leu Asn Trp Tyr Trp Gly Asn Asp Arg
        275                 280                 285

Ser Met Leu Ile Thr Asn Cys Leu Phe Arg Met Gly Gly Ala Ala Ile
    290                 295                 300

Ile Leu Ser Asn Arg Trp Arg Asp Arg Arg Arg Ser Lys Tyr Gln Leu
305                 310                 315                 320

Leu His Thr Val Arg Thr His Lys Gly Ala Asp Asp Lys Ser Tyr Arg
                325                 330                 335

Cys Val Leu Gln Gln Glu Asp Glu Asn Asn Lys Val Gly Val Ala Leu
            340                 345                 350

Ser Lys Asp Leu Met Ala Val Ala Gly Glu Ala Leu Lys Ala Asn Ile
        355                 360                 365

Thr Thr Leu Gly Pro Leu Val Leu Pro Met Ser Glu Gln Leu Leu Phe
    370                 375                 380

Phe Ala Thr Leu Val Ala Arg Lys Val Phe Lys Met Thr Asn Val Lys
385                 390                 395                 400

Pro Tyr Ile Pro Asp Phe Lys Leu Ala Ala Asn Asp Phe Cys Ile His
                405                 410                 415

Ala Gly Gly Lys Ala Val Leu Asp Glu Leu Glu Lys Asn Leu Glu Leu
            420                 425                 430

Thr Pro Trp His Leu Glu Pro Ser Arg Met Thr Leu Tyr Arg Phe Gly
        435                 440                 445

Asn Thr Ser Ser Ser Ser Leu Trp Tyr Glu Leu Ala Tyr Ala Glu Ala
    450                 455                 460

Lys Gly Arg Ile Arg Lys Gly Asp Arg Thr Trp Met Ile Gly Phe Gly
465                 470                 475                 480

Ser Gly Phe Lys Cys Asn Ser Val Val Trp Arg Ala Leu Arg Ser Val
                485                 490                 495

Asn Pro Ala Arg Glu Lys Asn Pro Trp Met Asp Glu Ile Glu Lys Phe
            500                 505                 510

Pro Val His Val Pro Lys Ile Ala Pro Ile Ala Ser
        515                 520
```

<210> SEQ ID NO 43
<211> LENGTH: 100
<212> TYPE: DNA
<213> ORGANISM: Artificial sequence
<220> FEATURE:

-continued

<223> OTHER INFORMATION: Primer for Vibrio harvei myristoyl ACP thioesterase

<400> SEQUENCE: 43

```
cggtctagat aacaatcaat gcaagactat tgcacacgtg ttgcgtgtga acaatggtca     60

ggagcttcac gtctgggaaa cgcccccaaa agaaaacgtg                          100
```

<210> SEQ ID NO 44
<211> LENGTH: 100
<212> TYPE: DNA
<213> ORGANISM: Artificial sequence
<220> FEATURE:
<223> OTHER INFORMATION: Primer for Vibrio harvei myristoyl ACP thioesterase

<400> SEQUENCE: 44

```
atactcggcc aatccagcga agtggtccat tcttctggcg aaaccagaag caatcaaaat     60

ggtgttgttt ttaaaaggca cgttttcttt tgggggcgtt                          100
```

<210> SEQ ID NO 45
<211> LENGTH: 3440
<212> TYPE: DNA
<213> ORGANISM: Brassica rapa

<400> SEQUENCE: 45

```
tctagaattc tctaattacg tctgtttgtt ctatttttta tatgatatca aatattcgtc     60

ataaatatat ggtttaagat gccaaaaaat tatttacttg gtgaatataa tacgttaaat    120

attagaaata catcatttag ttaaataaat aaccaaaaac caaaaattca tatccgcgct    180

ggcgcgcggt cagggtctcg ttagttttaa aatcaatgca gtttacaatt aatttccagc    240

tgaaaataag tataatttgt attgaaatta taaagtgaca ttttttgtgt aacaaatatt    300

ttgtgtaaca agaattaaaa aaaaaaacag aaaatactca gctttttttaa taataaaaaa    360

aattaattga gttagaaaat tgttgtacca ataacaaaag atttatatgg aattataaaa    420

tcaacacacc aataacacaa gactttttaa aaatttaaga ataatataag caataacaat    480

agaatcttca aattcttcaa atccttaaaa atcaatctcc cactattaat ccccccttagt    540

tttagttggt aatggcaacg tttgttgact accgtattgt aacttttgtc aaattgtcat    600

aaatacgtgt caaactctgg taaaaaatta gtctgctaca tctgtctttt atttataaaa    660

cacagctgtt aatcagaatt tggtttatta aatcaacaac ctgcacgaaa cttgtgtgag    720

catattttgt ctgtttctgg ttcatgacct tcttccgcat gatggccaag tgtaatggcc    780

acttgcaaga gcgtttcttc aacgagataa gtcgaacaaa tatttgtccg ttacgaccac    840

atataaaatc tccccatctc tatatatatat accagcattc accatcatga atacctcaaa    900

tcccaatctc acaaatactt caataaaaag accaaaaaaa attaaagcaa agaaaagcct    960

tcttgtgcac aaaaaaaaaa gaagccttct aggttttcac gacatgaagt tcactactct   1020

aatggtcatc acattggtga taatcgccat ctcgtctcct gttccaatta gagcaaccac   1080

ggttgaaagt ttcggagaag tggcacaatc gtgtgttgtg acagaactcg ccccatgctt   1140

accagcaatg accacggcag gagacccgac tacagaatgc tgcgacaaac tggtagagca   1200

gaaaccatgt ctttgtggtt atattcgaaa cccagcctat agtatgtatg ttacttctcc   1260

aaacggtcgc aaagtcttag atttttgtaa ggttcctttt cctagttgtt aaatctctca   1320

agacattgct aagaaaaata ttattaaaaa taaaagaatc aaactagatc tgatgtaaca   1380

atgaatcatc atgttatggt tgaagcttat atgctgaagt gtttgatttt atatatgtgt   1440
```

```
gtgtgtgtgt cctgctcaat ttttgaaaca cacacgtttc tcctgatttg gatttaaatt   1500
atattttgag ttaaaaaaaa gaaaaagatg gaatgctatt tatacaagtt gatgaaaaag   1560
tggaagtaca atttagatat ctcctacact taaagaatga aacaataata gacttacgaa   1620
acaaatgaaa aatacataaa ttgtcgacaa tcaacgtccg atgacgagtt tattattaaa   1680
aatttgtgtg aaggactagc agttcaacca aatgatattg aacatataca tcaacaaata   1740
tgataatcat aaaagagaga atgggggggg ggtgtcgttt accagaaacc tctttttctc   1800
agctcgctaa aaccctacca ctagagacct agctctgacc gtcggctcat cggtgccgga   1860
ggtgtaacct ttctttccca tgacccgaaa cctctctttc ccaactcacg aaaaccctac   1920
aatcaaaaac ctagctccga ccgtcggctc atcggtgccg aaggtgtaac ctttctctcc   1980
catcatagtt tctcgtaaat gaaagctaat tgggcaatcg attttttaat gtttaaacca   2040
tgccaagcca tttcttatag gacaattgtc aataatagca tcttttgagt tttgtctcaa   2100
aagtgacact agaagaaaaa agtcacaaaa atgacattca ttaaaaagta aaatatccct   2160
aataccttttg gtttaaatta aataagtaaa caaaaataaa taaaaacaaa taaaataaaa   2220
ataaaaaatg aaaaaaagaa attttttat agtttcagat tatatgtttt cagattcgaa   2280
attttttaaa ttccctttt taaattttct tttttgaaat tttttttttt gaaatttttt   2340
gaaactgttt ttaaaatttt tatttttaat tttttagtat ttattttta ttttataaaa   2400
ttttaaacgc taattccaaa actccccccc cccccccccc cccaattctc tcctagtctt   2460
tttctctttc ttatatttgg gcttctatct tctcttttt tttcaggccc aaagtatcat   2520
gtgtaacaac cggtgttcaa aaacgcgccc gcctggccgt ttactcgccc gattaaatga   2580
tgatcggaag gctgccatgg cgaggcggag gtaatcagtg gttctaggcg ctgaaactag   2640
aaaaccttca aaaatcgaaa ttttaagagc taaatcggtg tttatctcat gaatctatta   2700
tatttagttg aaactcacaa gaatcggttg taaaaactat gaaatcgtgc aaaaaaaatg   2760
aagaacaaaa tattctcaga tctggaaaac acagagaaga ggttgaagat gagggtaaaa   2820
tcgtattttg tcattcatta aactaaaatc aaaaaaaaat gatgcaaaat tcaatgataa   2880
taactcgaac tcgcaaccat atgcatcttt agactgcgac acggaccact agactaagca   2940
attttaatgt ttattcatca cagacctaat atatgtctaa aactaggcgc cgagtacgcc   3000
ccgcttaatc ccgagttttt gttagctcgc tagacccagg gtcaccgccc gactaacgag   3060
tagcgtaatt ctgaactggg gtaacaacat agagaacatc gccgaccctt ccctgccgat   3120
gatgccgcct ccgatgaact tcctgtaacg ccttcagttt ccattgattt tccccttttaa   3180
tctgatcagt tccatgtttt atccaactca tcccactccg tagcatttaa tcgatctcat   3240
catttacata cataaccagt aggaggtctc atataaattt gaacgtttcc agcgatgaac   3300
agtgccaatc tctgcgaaat ccatttctct aagctcaggg ctggcggctg cagcccgggg   3360
atccactagt tctaggcggc cgcaccgcgg tggagctcca attcgcccta tagtgagtcg   3420
tattacgcgc gctcactggc                                               3440
```

<210> SEQ ID NO 46
<211> LENGTH: 3898
<212> TYPE: DNA
<213> ORGANISM: Brassica rapa

<400> SEQUENCE: 46

```
ctcgagagct gaaggatttt ttgttagaga ttcaacgaca gatggaccct tcctccacta     60
```

-continued

```
ggcaactgca agaacctaac aatgcaaata tcactcctcc tcagccttca aggagcgtta    120
ataggactgg aacaagcggt caagtgagta aattttcctt ccaagataga tctctatggt    180
tcggttcatg aagtttgtgg tttaattgtg tagcaacagg atagtgcaag tgagaataga    240
gttcgacctc atctacctac cccggaacct ctgaatgtat ccccattgaa gaagaagagg    300
gcaaatcctg cacccagaag gataaagaaa ttttggacgc ctgaagaagt ggcagttctg    360
agggaaggag taaaagagta tgtctactac tactactcta taatcaagtt tcaagaagct    420
gagcttggct ctcactttat atgtttgatg ttgttgtgca ggtatggtaa atcatggaaa    480
gagataaaga atgcaaaccc tgaagtattg gcagagagga ctgaggtgag agagcatgtc    540
acttttgtgt tactcatctg aattatctta tatgcgaatt gtaagtggta ctaaaaggtt    600
tgtaactttt ggtaggtgga tttgaaggat aaatggagga acttgcttcg gtagcggtaa    660
caagttttat attgctatga agttttttttg cctgcgtgac gtatcagcag ctgtggagaa    720
gatggtatta gaaagggtct tttcacattt tgtgttgtga caaatattaa ttcggccggt    780
atggtttggt taagacttgt tgagagacgt gtggggtttt ttgatgtata attagtctgt    840
gtttagaacg aaacaagact tgttgcgtat gcttttttta acttgagggg gtttgttgtt    900
gttagttagg aacttgactt tgtctctttc tctcaagatc tgattggtaa ggtctgggtg    960
gtagtactgt ttggtttaat ttgttttgac tattgagtca ctgtggccca ttgactttaa   1020
attaggctgg tatatttttt ggtttaaaac cggtctgaga tagtgcaatt tcgattcagt   1080
caattttaaa ttcttcaagg taatgggctg aatacttgta tagttttaag acttaacagg   1140
ccttaaaagg cccatgttat cataaaacgt cattgtttag agtgcaccaa gcttataaaa   1200
tgtagccagg ccttaaaaga cttaacaggc cttaaaagac ttaacattcc ttaaaaggcc   1260
catgttatca taaaacgtca tcgttttgag tgcaccaagc taaatgtagc caggccttaa   1320
aagacttaac aggccttaaa aggcccatgt tatcataaaa cgccgtcgtt ttgagtgcac   1380
caagcttata aatgtagcca gctacctcgg gacatcacgc tctttgtaca ctccgccatc   1440
tctctctctc tcgagcagat ctctctcggg aatatcgaca atgtcgacca ctttctgctc   1500
ttccgtctcc atgcaagcca cttctctggt aatctcatct ccttcttgtg ttcccagatc   1560
gctctgatca tactttcttt tagatcattt gcctctgatc tgttgcttga tgtttgttaa   1620
ctctccacgc atgtttgatt atgttgagaa ttagaaaaaa aatgttagct ttacgaatct   1680
ttagtgatca tttcaattgg atttgcaatc ttgtgtgaca tttgaggctt gtgtagattt   1740
cgatctgtat tcattttgaa tcacagctat aatagtcatt tgagtagtag tgtttttaaa   1800
tgaacatgtt ttgttgtatt gatggaacaa acaggcagca acaacgagga ttagtttcca   1860
gaagccagct ttggtttcaa cgactaatct ctccttcaac ctccgccgtt caatccccac   1920
tcgtttctca atctcctgcg cggtatgttc tcattctcag catttatttc gagcttgctt   1980
gtcatggtac tctctctaat tgtctatttg gtttattagg ccaaaccaga gacggttgag   2040
aaagtgtcta agatagttaa gaagcagcta tcactcaaag acgaccaaaa ggtcgttgcg   2100
gagaccaagt ttgctgatct tggagcagat tctctcgaca ctgtaagtca tcaatcattc   2160
tcttatgtga ataaagagaa cttgaagagt ttgtttttaa catattaact gagtgttttg   2220
catgcaggtt gagatagtga tgggtttaga ggaagagttt gatatcgaaa tggctgaaga   2280
gaaagctcag aagattgcta ctgtggagga agctgctgaa ctcattgaag agctcgttca   2340
acttaagaag taattttagt attaagagca gccaaggctt tgttgggttt gttgttttca   2400
taatcttcct gtcattttct ttttctttaa tgtgtcaagc gactctgttg gtttaaagta   2460
```

-continued

```
gtatctgttt gccatggatc tctctctatt tgtcgactga aaacttttgg tttacacatg   2520

aaagcttgtt cttgttcttt cttaaatcga aatgccaaat gcgagattag ggaatcttgt   2580

attaacacat acataagtca aagagtaggc cctaagatga caatttataa acaatcctat   2640

tcacattgta tatacaggtt atgattattc ccaatcagcg tcaaagaatc cagcatcttt   2700

catctctgaa tagtagacat tctccaagtt cacatcttcc tcctgcacca aaaaccagta   2760

ctaaatcatg aacattgcaa taatcacatg cctaggcgag agttttggtg atgtggtgtt   2820

agtgatagtg atactgatgg tgctagagcg gttaagaagg attaacctgg aagaagtctg   2880

caaggaaagt aacatagaga agaggaagat aggagtggta acaaacactt gtgatcccat   2940

acagcctccc agcatttttc aaatgttatt tccttacata aagaaacaag agaagtctga   3000

ctagatgata tttatatagg ataagtgttt taccataagc caaagtgagc gccgtttgca   3060

agagctaacc agacagtaca cgtttggcat atatctcatc aacatgatct gaaaagtaac   3120

atatcacagt taatgaacac aatggttacc ttgagaagca aatcaagacc tataacaagc   3180

ccagagatga ggaaagtccg tgtcaacgct tcaccgccat tcgcgtagtt tccttggaag   3240

acaaaggcca ccaaccaaac ttacttccag aaacaacact ccaaatgttg tcaacaaagt   3300

caatagattc caaactactt cgttacaggg ttgtatagat aatataatag aatagtggga   3360

agatagtata aataaaataa ataaaagatc ctatcggtaa atagtttata atatcggggg   3420

cgtatataaa gtataaaaga aactcttctc caatccgacc gttgaaaatc actctcaatc   3480

tctggcgtaa cgaccggatc gttcgcgcgt aattttcgct gctataaata gaaactttcc   3540

tcttctgttt ctcgatcaaa attttttttt ggaaaaatta agtttgaatc tatcgtagat   3600

gctgtgacaa aaaaaaattg ttttatcgaa gatgagaaac atgaggcctg ttcatgcaag   3660

gaaccagacc acggatccat cttcgccgat gatgacgtct cctctgatga atcgtcacgc   3720

acggacagga tccaacgctg gaccagcatc taacgccaag aaagcacaga cgaaagcagc   3780

agctcagaga ctcgcggctg tgatgtcgaa ccaaacaggc gacgatgaag acagtgatga   3840

tgacctttcc tttgactaca acgctgtcgg aagcattggt ctcgctgccg gaagatct     3898
```

<210> SEQ ID NO 47
<211> LENGTH: 4325
<212> TYPE: DNA
<213> ORGANISM: Brassica rapa
<220> FEATURE:
<221> NAME/KEY: misc_feature
<222> LOCATION: (432)..(432)
<223> OTHER INFORMATION: N= A, T, C or G
<220> FEATURE:
<221> NAME/KEY: misc_feature
<222> LOCATION: (439)..(439)
<223> OTHER INFORMATION: N= A, T, C or G
<220> FEATURE:
<221> NAME/KEY: misc_feature
<222> LOCATION: (442)..(442)
<223> OTHER INFORMATION: N= A, T, C or G
<220> FEATURE:
<221> NAME/KEY: misc_feature
<222> LOCATION: (3635)..(3635)
<223> OTHER INFORMATION: N= A, T, C or G
<220> FEATURE:
<221> NAME/KEY: misc_feature
<222> LOCATION: (3716)..(3716)
<223> OTHER INFORMATION: N= A, T, C or G
<220> FEATURE:
<221> NAME/KEY: misc_feature
<222> LOCATION: (3719)..(3720)
<223> OTHER INFORMATION: N= A, T, C or G
<220> FEATURE:

```
<221> NAME/KEY: misc_feature
<222> LOCATION: (3802)..(3802)
<223> OTHER INFORMATION: N= A, T, C or G
<220> FEATURE:
<221> NAME/KEY: misc_feature
<222> LOCATION: (3804)..(3804)
<223> OTHER INFORMATION: N= A, T, C or G

<400> SEQUENCE: 47

ctcgaggcag tcactaacat gaagtttgac gaggagccca actatgggaa gcttatttct     60

cttttcgata ctctaattga gccgtgcgct ctatctagac caattagaat tgatggagct    120

ctaaaggttg ctggctgttt tcttgttcat atgattaact tctaaacttg tgtataaata    180

ttctctgaaa gtgcttcttt tggcatatgt aggttgggca aaaacgagga agattgcttc    240

tcaatttgga agaggatgaa cagccgaaga agaaaataag aataggcagt cctgctactc    300

aatggatctc agtctataac ggtcgtcgtc ccatgaaaca gaggtaaaac attttttgca    360

tatacacttt gaaagttcct cactaactgt gtaatctttt ggtagatatc actacaatgt    420

cggagagaca anggctgsnc ancatataca aaagggaaat gaagatggcc ttttgattag    480

ctgtgtagca tcagcagcta atctctgggc tctcatcatg gatgctggaa ctggattcac    540

ttctcaagtt tatgagttgt caccggtctt cctacacaag gtaataatca gttgaagcaa    600

ttaagaatca atttgatttg tagtaaacta agaagaactt accttatgtt ttccccgcag    660

gactggatta tggaacaatg ggaaaagaac tactatataa gctccatagc tggttcagat    720

aacgggagct ctttagttgt tatgtcaaaa ggttagtgtt tagtgaataa taaacttata    780

ccacaaagtc ttcattgact tatttatata cttgttgtga attgctagga actacttatt    840

ctcagcagtc atacaaagtg agtgactcat ttccgttcaa gtggataaat aagaaatgga    900

aagaagattt tcatgtaacc tccatgacaa ctgctggtaa tcgttggggt gtggtaatgt    960

cgaggaactc tggcttctct gatcaggtag gtttttgtct cttattgtct ggtgttttta   1020

ttttcccctg atagtctaat atgataaact ctgcgttgtg aaaggtggtg gagcttgact   1080

ttttgtaccc aagcgatggg atacatagga ggtgggagaa tgggtataga ataacatcaa   1140

tggcagcaac tgcggatcaa gcagctttca tattaagcat accaaagcgt aagatggtgg   1200

atgaaactca agagactctc cgcaccaccg cctttccaag tactcatgtc aaggttggtt   1260

tctttagctt tgaacacaga tttggatctt tttgttttgt ttccatatac ttaggacctg   1320

agagcttttg gttgattttt ttttcaggac aaatgggcga agaatctgta cattgcatca   1380

atatgctatg gcaggacagt gtgctgatac acacttaagc atcatgtgga aagccaaaga   1440

caattggagc gagactcagg gtcgtcataa taccaatcaa agacgtaaaa ccagacgcaa   1500

cctctttggt tgaatgtaat gaaagggatg tgtcttggta tgtatgtacg aataacaaaa   1560

gagaagatgg aattagtagt agaaatattt gggagctttt taagcccttc aagtgtgctt   1620

tttatcttat tgatatcatc catttgcgtt gtttaatgcg tctctagata tgttcctata   1680

tctttctcag tgtctgataa gtgaaatgtg agaaaaccat accaaaccaa aatattcaaa   1740

tcttattttt aataatgttg aatcactcgg agttgccacc ttctgtgcca attgtgctga   1800

atctatcaca ctagaaaaaa acatttcttc aaggtaatga cttgtggact atgttctgaa   1860

ttctcattaa gtttttattt tctgaagttt aagtttttac cttctgtttt gaaatatatc   1920

gttcataaga tgtcacgcca ggacatgagc tacacatcgc acatagcatg cagatcagga   1980

cgatttgtca ctcacttcaa acacctaaga gcttctctct cacagcgcac acacatatgc   2040

atgcaatatt tacacgtgat cgccatgcaa atctccattc tcacctataa attagagcct   2100
```

-continued

```
cggcttcact ctttactcaa accaaaactc atcactacag aacatacaca aatggcgaac   2160
aagctcttcc tcgtctcggc aactctcgcc ttgttcttcc ttctcaccaa tgcctccgtc   2220
tacaggacgg ttgtggaagt cgacgaagat gatgccacaa atccagccgg cccatttagg   2280
attccaaaat gtaggaagga gtttcagcaa gcacaacacc tgaaagcttg ccaacaatgg   2340
ctccacaagc aggcaatgca gtccggtagt ggtccaagct ggaccctcga tggtgagttt   2400
gattttgaag acgacgtgga gaaccaacaa cagggcccgc agcagaggcc accgctgctc   2460
cagcagtgct gcaacgagct ccaccaggaa gagccacttt gcgtttgccc aaccttgaaa   2520
ggagcatcca aagccgttaa acaacagatt cgacaacaac agggacaaca aatgcaggga   2580
cagcagatgc agcaagtgat tagccgtatc taccagaccg ctacgcactt acctagagct   2640
tgcaacatca ggcaagttag catttgcccc ttccagaaga ccatgcctgg gcccggcttc   2700
tactagattc caaacgaata tcctcgagag tgtgtatacc acggtgatat gagtgtggtt   2760
gttgatgtat gttaacacta catagtcatg gtgtgtgttc cataaataat gtactaatgt   2820
aataagaact actccgtaga cggtaataaa agagaagttt ttttttttac tcttgctact   2880
ttcctataaa gtgatgatta acaacagata caccaaaaag aaaacaatta atctatattc   2940
acaatgaagc agtactagtc tattgaacat gtcagatttt ctttttctaa atgtctaatt   3000
aagccttcaa ggctagtgat gataaaagat catccaatgg gatccaacaa agactcaaat   3060
ctggttttga tcagatactt caaaactatt tttgtattca ttaaattatg caagtgttct   3120
tttatttggt gaagactctt tagaagcaaa gaacgacaag cagtaataaa aaaaacaaag   3180
ttcagtttta agatttgtta ttgacttatt gtcatttgaa aaatatagta tgatattaat   3240
atagttttat ttatataatg cttgtctatt caagatttga gaacattaat atgatactgt   3300
ccacatatcc aatatattaa gtttcatttc tgttcaaaca tatgataaga tggtcaaatg   3360
attatgagtt ttgttattta cctgaagaaa agataagtga gcttcgagtt tctgaagggt   3420
acgtgatctt catttcttgg ctaaaagcga atatgacatc acctagagaa agccgataat   3480
agtaaactct gttcttggtt tttggtttaa tcaaaccgaa ccggtagctg agtgtcaagt   3540
cagcaaacat cgcaaaccat atgtcaattc gttagattcc cggtttaagt tgtaaaccgg   3600
tatttcattt ggtgaaaacc ctagaagcca gccancettt ttaatctaat ttttgcaaac   3660
gagaagtcac cacacctctc cactaaaacc ctgaacctta ctgagagaag cagagncann   3720
aaagaacaaa taaaacccga agatgagacc accacgtgcg gcgggacgtt caggggacgg   3780
ggaggaagag aatgrcggcg gnsntttggt ggcggcggcg gacgttttgg tggcggcggt   3840
ggacgttttg gtggcggcgg tggacctttg gtggtggata tcgtgacgaa ggacctccca   3900
gtgaagtcat tggttcgttt actcttttct tagtcgaatc ttattcttgc tctgctcgtt   3960
gttttaccga taaagcttaa gactttattg ataaagttct cagctttgaa tgtgaatgaa   4020
ctgtttcctg cttattagtg ttcctttgtt ttgagttgaa tcactgtctt agcacttttg   4080
ttagattcat ctttgtgttt aagttaaaag gtagaaactt tgtgacttgt ctccgttatg   4140
acaaggttaa ctttgttggt tataacagaa gttgcgacct ttctccatgc ttgtgagggt   4200
gatgctgtgg accaagctct ctcaggcgaa gatcccttac ttcaatgccc caatctactt   4260
ggaaaacaag acacagattg ggaaagttga tgagatccaa gcttgggctg caggtcgacg   4320
aattc                                                               4325
```

<210> SEQ ID NO 48

-continued

```
<211> LENGTH: 184
<212> TYPE: PRT
<213> ORGANISM: Brassica rapa

<400> SEQUENCE: 48

Met Ala Asn Lys Leu Phe Leu Val Ser Ala Thr Leu Ala Leu Phe Phe
1               5                   10                  15

Leu Leu Thr Asn Ala Ser Val Tyr Arg Thr Val Val Glu Val Asp Glu
            20                  25                  30

Asp Asp Ala Thr Asn Pro Ala Gly Pro Phe Arg Ile Pro Lys Cys Arg
        35                  40                  45

Lys Glu Phe Gln Gln Ala Gln His Leu Lys Ala Cys Gln Gln Trp Leu
    50                  55                  60

His Lys Gln Ala Met Gln Ser Gly Ser Gly Pro Ser Trp Thr Leu Asp
65                  70                  75                  80

Gly Glu Phe Asp Phe Glu Asp Asp Val Glu Asn Gln Gln Gln Gly Pro
                85                  90                  95

Gln Gln Arg Pro Pro Leu Leu Gln Gln Cys Cys Asn Glu Leu His Gln
            100                 105                 110

Glu Glu Pro Leu Cys Val Cys Pro Thr Leu Lys Gly Ala Ser Lys Ala
        115                 120                 125

Val Lys Gln Gln Ile Arg Gln Gln Gln Gly Gln Gln Met Gln Gly Gln
    130                 135                 140

Gln Met Gln Gln Val Ile Ser Arg Ile Tyr Gln Thr Ala Thr His Leu
145                 150                 155                 160

Pro Arg Ala Cys Asn Ile Arg Gln Val Ser Ile Cys Pro Phe Gln Lys
                165                 170                 175

Thr Met Pro Gly Pro Gly Phe Tyr
            180
```

PLANT SEED OILS

RELATED APPLICATIONS

This is a Divisional of Application Ser. No. 08/926,522, filed Sep. 9, 1997, now U.S. Pat. No. 6,426,447, which is a Continuation of application Ser. No. 08/458,173, filed Jun. 2, 1995, now abandoned, which is a continuation-in-part of U.S. application Ser. No. 07/949,102, filed Sep. 21, 1992, now abandoned, which is a continuation-in-part of U.S. application Ser. No. 07/762,762, filed Sep. 16, 1991, now abandoned, which is a continuation-in-part of U.S. application Ser. No. 07/615,784, filed Nov. 14, 1990, now abandoned, and PCT/US91/01746, filed Mar. 14, 1991, all of which are herein incorporated by reference, and U.S. application Ser. No. 07/494,106, filed Mar. 16. 1990.

FIELD OF THE INVENTION

This invention relates to the application of genetic engineering techniques to plants. More specifically, the invention relates to a strategy for effecting changes in the composition of plant seed oils through the use of foreign DNA sequences which are derived from sources outside of the target plant gene pool.

BACKGROUND OF THE INVENTION

Fatty acids are organic acids having a hydrocarbon chain of from about 4 to 24 carbons. Many different kinds of fatty acids are known which differ from each other in chain length, and in the presence, number and position of double bonds. In cells, fatty acids typically exist in covalently bound forms, the carboxyl portion being referred to as a fatty acyl group. The chain length and degree of saturation of these molecules is often depicted by the formula CX:Y, where "X" indicates number of carbons and "Y" indicates number of double bonds. As the carbon chain of fatty acyl molecules always contains an even number of carbons, the formula "$C_{2x}$" may also be used to represent carbon chain length.

Fatty acyl groups are major components of many lipids, and their long, non-polar hydrocarbon chain is responsible for the water-insoluble nature of these lipid molecules. The type of covalent linkage of the fatty acyl group to other factors can vary. For example, in biosynthetic reactions they may be covalently bound via a thioester linkage to an acyl carrier protein (ACP) or to CoenzymeA (CoA), depending on the particular enzymatic reaction. In waxes, fatty acyl groups are linked to fatty alcohols via an ester linkage, and triacylglycerols have three fatty acyl groups linked to a glycerol molecule via an ester linkage.

The fatty acid composition of an oil determines its physical and chemical properties, and thus its uses. Plants, especially plant species which synthesize large amounts of oils in plant seeds, are an important source of oils both for edible and industrial uses.

The fatty acid composition of major oilseeds, ordered here by palmitate content, is shown in Table 1. With the exception of laurate (C12:0), sources of coconut endosperm and palm kernel, the common edible oils all basically consist of 16:0, 18:0, 18:1 (oleate), 18:2 (linoleate), and 18:3 (linolenate).

TABLE 1

| | 12:0 | 14:0 | 16:0 | 18:0 | 18:1 | 18:2 | 18:3 | 20:1 | 22:1 |
|---|---|---|---|---|---|---|---|---|---|
| rape (HEAR) | | | 3 | 0.8 | 9.9 | 13.5 | 9.8 | 6.8 | 53.6 |
| rape (LEAR) | | | 4.9 | 1.4 | 56.4 | 24.2 | 10.5 | | |
| sunflower | | 0.1 | 5.8 | 5.2 | 16 | 71.5 | 0.2 | | |
| peanut | | | 6.7 | 4.3 | 71.4 | 11.1 | 6.5 | | |
| safflower | | | 7.6 | 2 | 10.8 | 79.6 | | | |
| coconut | 40.2 | 15.5 | 7.6 | 2.4 | 5.2 | 1.2 | | | |
| oil palm | 50.9 | 18.4 | 8.7 | 1.9 | 14.6 | 1.2 | | | |
| kernel | | | 15.3 | 3.8 | 20.7 | 55.8 | 9.4 | | |
| soybean | | | | | | | | | |
| cotton | | 1 | 23.4 | 2.5 | 17.9 | 54.2 | | | |
| oil palm meaocrap | 0.1 | 1.2 | 46.8 | 3.8 | 37.6 | | | | |

Plant breeders have successfully modified the yield and fatty acid composition of various plant seed oils through programs of introducing desired traits by plant crosses and selection of progeny carrying the desired trait forward. Application of this technique thus is limited to traits which are found within the same plant species. Alternatively, exposure to mutagenic agents can also introduce traits which may produce changes in the composition of a plant seed oil. However, it is important to note that Fatty Acid Synthesis (FAS) occurs in leaf (chloroplasts) and seed tissue (proplastids). Thus, although a mutagenesis approach can sometimes result in a desired modification of the composition of a plant seed oil, it is difficult to effect a change which will not alter FAS in other tissues of the plant.

A wide range of novel vegetable oils compositions and/or improved means to obtain or manipulate fatty acid compositions, from biosynthetic or natural plant sources, are needed for a variety of intended uses. Plant breeding, even with mutagenesis, cannot meet this need and provide for the introduction of any oil traits which are outside of the target plant's gene pool.

Various oils compositions are now in demand. For example, edible oil sources containing the minimum possible amounts of saturates, palmitate (C16:0) and stearate (C18:0) saturated fatty acids, are desired for dietary reasons and alternatives to current sources of highly saturated oil products, such as tropical oils, are also needed. Generating a spread of C4, C6 and C8 short chain 3-keto fatty acids could become a key improvement in polyhydroxybutyrate (PHB)-based biodegradable plastics made in bacteria and plants. Medium-chain fatty acids have special importance in the detergent and lubricant industries or in the formulation of edible oils with reduced caloric value or other health benefits. See for example, U.S. Pat. No. 4,863,753 and Barch, A. C. & Babayan, V. K., *Am. J. Clin. Nat.* (1982) 36:950–962. Longer chain fatty acids may have certain other utilities, i.e., C16 and C18 have particular uses in margarine and other solid oil-based products, and very long chain fatty acids also have specialized uses, i.e., C22 is used to make peanut butter smoother. As such, a ready source of a variety of fatty acid lengths, including storage lipids which have incorporated differing chain length fatty acids in desired ratios, are desired for a variety of industrial and food use fields. Improved yield of current oilseed crops and the development of novel plant fatty acid compositions and oils products are also needed. Examples of novel plant fatty acid and oils products include fatty alcohols, epoxy fatty acids (e.g., biodegradable paint thinner), long chain liquid wax (e.g., jojoba oil substitute), hydroxylated fatty acids (motor lubricants) or cyclopropanated fatty acids (motor lubricants).

With the advent of genetic engineering, the ability to produce a transgenic plant containing any desired DNA sequence of interest is a reality. And with the development of basic plant biotechnology methodologies, many suggestions have been proposed for fatty acid modification. A good number of these strategies, however, rely upon the insertion of genes isolated from organisms outside of the target plant species oftentimes traits from very divergent type plants to alter plant oils. It was not known whether such traits were limited to certain plant types. As one example, certain oil compositions appear to be limited to certain climates. Highly saturated oils, especially those high stearate (C18:0), are strongly correlated with tropical plant sources, e.g., oil palm, coconut. Temperate zone oilseeds are very typically highly unsaturated, e.g., corn, soybean, canola. Thus, the insertion of genes to achieve high stearate in a temperate crop would not meet the usual climatic condition for such trait.

Additionally, it was not known whether the introduced enzymes could effectively compete with the natural enzymes for substrate or whether it would be necessary to reduce the level of the endogenous enzymes to observe a modified fatty acid oil phenotype. Also, it was not known whether antisense technology could be used to influence the fatty acid pathway. In addition, it was not known, in the event that the composition of fatty acids were modified, whether the incorporation of such fatty acids into triglycerides would occur, whether transgenic seed with an altered oils composition would germinate, and to what extent if any, whether seed yield and/or oil yield from such seeds would be affected.

Moreover, in order to genetically engineer plants one must have in place the means to transfer genetic material to the plant in a stable and heritable manner. Additionally, one must have nucleic acid sequences capable of producing the desired phenotypic result, regulatory regions capable of directing the correct application of such sequences, and the like. Moreover, it should be appreciated that to produce a desired modified oils phenotype requires that the FAS pathway of the plant is modified to the extent that the ratios of reactants are modulated or changed.

Higher plants appear to synthesize fatty acids via a common metabolic pathway in plant plastid organelles (i.e., chloroplasts, proplastids, or other related organelles) as part of the FAS complex. (By fatty acid is meant free fatty acids and acyl-fatty acid groups.) Outside of plastid organelles, fatty acids are incorporated into triacylglycerols (triglycerides) and used in plant membranes and in neutral lipids. In developing seeds, where oils are produced and stored as sources of energy for future use, FAS occurs in proplastids.

The production of fatty acids begins in the plastid with the reaction between Acyl Carrier Protein (ACP) and acetylCoA to produce acetyl-ACP catalyzed by the enzyme acetylCoA: ACP transacylase (ATA). Elongation of acetyl-ACP to 16- and 18-carbon fatty acids involves the cyclical action of the following sequence of reactions: condensation with a two-carbon unit from malonyl-ACP to form a β-ketoacyl-ACP (β-ketoacyl-ACP synthase), reduction of the keto-function to an alcohol (β-ketoacyl-ACP reductase), dehydration to form an enoyl-ACP (β-hydroxyacyl-ACP dehydrase), and finally reduction of the enoyl-ACP to form the elongated saturated acyl-ACP (enoyl-ACP reductase). β-ketoacyl-ACP synthase I catalyzes elongation up to palmitoyl-ACP (C16:0), whereas β-ketoacyl-ACP synthase II catalyzes the final elongation to stearoyl-ACP (C18:0). The longest chain fatty acids produced by the FAS are 18 carbons long. Monounsaturated fatty acids are also produced in the plastid through the action of a desaturase enzyme.

Common plant fatty acids, such as oleic, linoleic and α-linolenic acids, are the result of sequential desaturation of stearate. The first desaturation step is the desaturation of stearoyl-ACP (C18:0) to form oleoyl-ACP (C18:1) in a reaction often catalyzed by a Δ-9 desaturase, also often referred to as a "stearoyl-ACP desaturase" because of its high activity toward stearate the 18 carbon acyl-ACP. The desaturase enzyme functions to add a double bond at the ninth carbon in accordance with the following reaction (I):

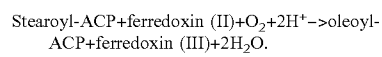

Stearoyl-ACP+ferredoxin (II)+$O_2$+$2H^+$->oleoyl-ACP+ferredoxin (III)+$2H_2O$.

In subsequent sequential steps for triglyceride production, polyunsaturated fatty acids may be produced. These desaturations occur outside of the plastid as a result of the action of membrane-bound enzymes. Difficulties in the solubilization of such membrane-bound enzymes has hindered efforts to characterize these enzymes. Additional double bonds are added at the twelve position carbon and thereafter, if added, at the 15 position carbon through the action of Δ-12 desaturase and Δ-15 desaturase, respectively. These "desaturases" thus create mono- or polyunsaturated fatty acids respectively.

A third β-ketoacyl-ACP synthase has been reported in *S. oleracea* leaves having activity specific toward very short acyl-ACPs. This acetoacyl-ACP synthase or "β-ketoacyl-ACP" synthase III has a preference to acetyl-CoA over acetyl-ACP. Jaworski, J. G., et al., *Plant Phys.* (1989) 90:41–44. It has been postulated that this enzyme may be an alternate pathway to begin FAS, instead of ATA.

The fatty acid composition of a plant cell is a reflection of the free fatty acid pool and the fatty acids (fatty acyl groups) incorporated into triglycerides. Thus, in a triglyceride molecule, represented as Formula (I)

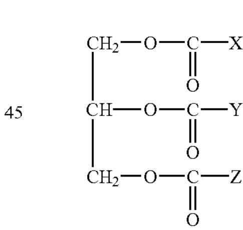

X, Y, and Z each represent fatty acids which may be the same or different from one another. Various combinations of fatty acids in the different positions in the triglyceride will alter the properties of triglyceride. For example, if the fatty acyl groups are mostly saturated fatty acids, then the triglyceride will be solid at room temperature. In general, however, vegetable oils tend to be mixtures of different triglycerides. The triglyceride oil properties are therefore a result of the combination of triglycerides which make up the oil, which are in turn influenced by their respective fatty acid compositions.

For example, cocoa-butter has certain desirable qualities (mouth feel, sharp melting point, etc.) which are a function of its triglyceride composition. Cocoa-butter contains approximately 24.4% palmitate (16:0), 34.5% stearate (18:0), 39.1% oleate (18:1) and 2% linoleate (18:2). Thus, in cocoa butter, palmitate-oleate-stearate (POS) (i.e., X, Y and Z, respectively, in Formula I) comprises almost 50% of triglyceride composition, with stearate-oleate-stearate (SOS) and palmitate-oleate-palmitate (POP) comprising the major portion of the balance at 39% and 16%, respectively, of the triglyceride composition. Other novel oils compositions of interest might include trierucin (three erucic) or a triglyceride with medium chain fatty acids in each position of the triglyceride molecule.

Thus, a variety of plant oils modifications are desired, including alternative crop sources for certain oils products and/or means to provide novel fatty acid compositions for plant seed.

BRIEF DESCRIPTION OF THE FIGURES

FIGS. 1A, 1B, 1C, and 1D show the nucleic acid sequence (SEQ ID NO: 1) and translated amino acid sequence (SEQ ID NO: 2)of a safflower stearoyl-ACP desaturase cDNA clone. The mature protein sequence begins at the alanine residue at amino acid 34.

FIGS. 2A, 2B, 2C, and 2D show the nucleic acid sequence (SEQ ID NO: 3) and translated amino acid sequence (SEQ ID NO: 4) of a castor stearoyl-ACP desaturase cDNA clone.

FIGS. 3A, 3B, and 3C show the nucleic acid sequence (SEQ ID NO: 5) and translated amino acid sequence (SEQ ID NO: 6) of a *Brassica campestris* stearoyl-ACP desaturase cDNA clone.

FIG. 4. Preliminary nucleic acid sequence (SEQ ID NO: 7) and translated amino acid sequence (SEQ ID NO: 8) of a partial jojoba stearoyl-ACP desaturase cDNA clone are provided.

FIGS. 5A, 5B, 5C, 5D, and 5E show the nucleic acid sequence (SEQ ID NO: 9) and translated amino acid sequence (SEQ ID NO: 10) of a bay C12:0-ACP thioesterase cDNA clone. The mature protein sequence begins at the leucine residue at amino acid 84.

FIGS. 6A, 6B, 6C, 6D, and 6E show the nucleic acid sequence (SEQ ID NO: 11) and translated amino acid sequence (SEQ ID NO: 12) of a second bay thioesterase cDNA clone, bayD. This cDNA represents a second class of bay thioesterase genes.

FIGS. 7A, 7B, 7C, 7D, 7E, and 7F show the nucleic acid sequence (SEQ ID NO: 13) and translated amino acid sequence (SEQ ID NO: 14) of safflower thioesterase cDNA clone, 2-1.

FIGS. 8A, 8B, 8C, 8D, and 8E show the nucleic acid sequence (SEQ ID NO: 15) and translated amino acid sequence (SEQ ID NO: 16) of safflower thioesterase cDNA clone, 5-2.

FIGS. 9A, 9B, 9C, 9D, 9E, and 9F show the nucleic acid sequence (SEQ ID NO: 17) and translated amino acid sequence (SEQ ID NO: 18) of a camphor PCR-generated thioesterase encoding sequence.

FIGS. 10A, 10B, 10C, and 10D show the nucleic acid sequence (SEQ ID NO: 19) and translated amino acid sequence (SEQ ID NO: 20) of a *Brassica campestris* acyl-ACP thioesterase cDNA clone. Translated amino acid sequence is shown from the proposed methionine initiation codon.

FIG. 11. Preliminary nucleic acid sequence from the 5' end of a partial *Cuphea hookeriana* acyl-ACP thioesterase cDNA clone are provided (SEQ ID NO: 21). The underlined "CTT" codon indicates the position of the presumed mature protein N-terminal amino acid.

FIG. 12. Preliminary nucleic acid sequence from the 5' end of a partial elm acyl-ACP thioesterase cDNA clone is provided (SEQ ID NO: 22).

FIGS. 13A, 13B, 13C, 13D, and 13E show the nucleic acid sequence (SEQ ID NO: 23) and translated amino acid sequence (SEQ ID NO: 24) of a castor β-ketoacyl-Acp synthase factor B (50 kD) cDNA clone. The mature protein sequence begins at the asparagine residue at amino acid 61.

FIGS. 14A, 14B, 14C, 14D, 14E, and 14F show the nucleic acid sequence (SEQ ID NO: 25) and translated amino acid sequence (SEQ ID NO: 26) of a castor β-ketoacyl-ACP synthase factor A (46 kD) cDNA clone (SEQ ID NO: 17). The mature protein sequence begins at the lysine residue at amino acid 122.

FIGS. 15A, 15B, 15C, and 15D show the nucleic acid sequence (SEQ ID NO: 36) and translated amino acid sequence (SEQ ID NO: 37) of a *Brassica campestris* β-ketoacyl-ACP synthase factor B (50 kD) cDNA clone.

Figure 16D:
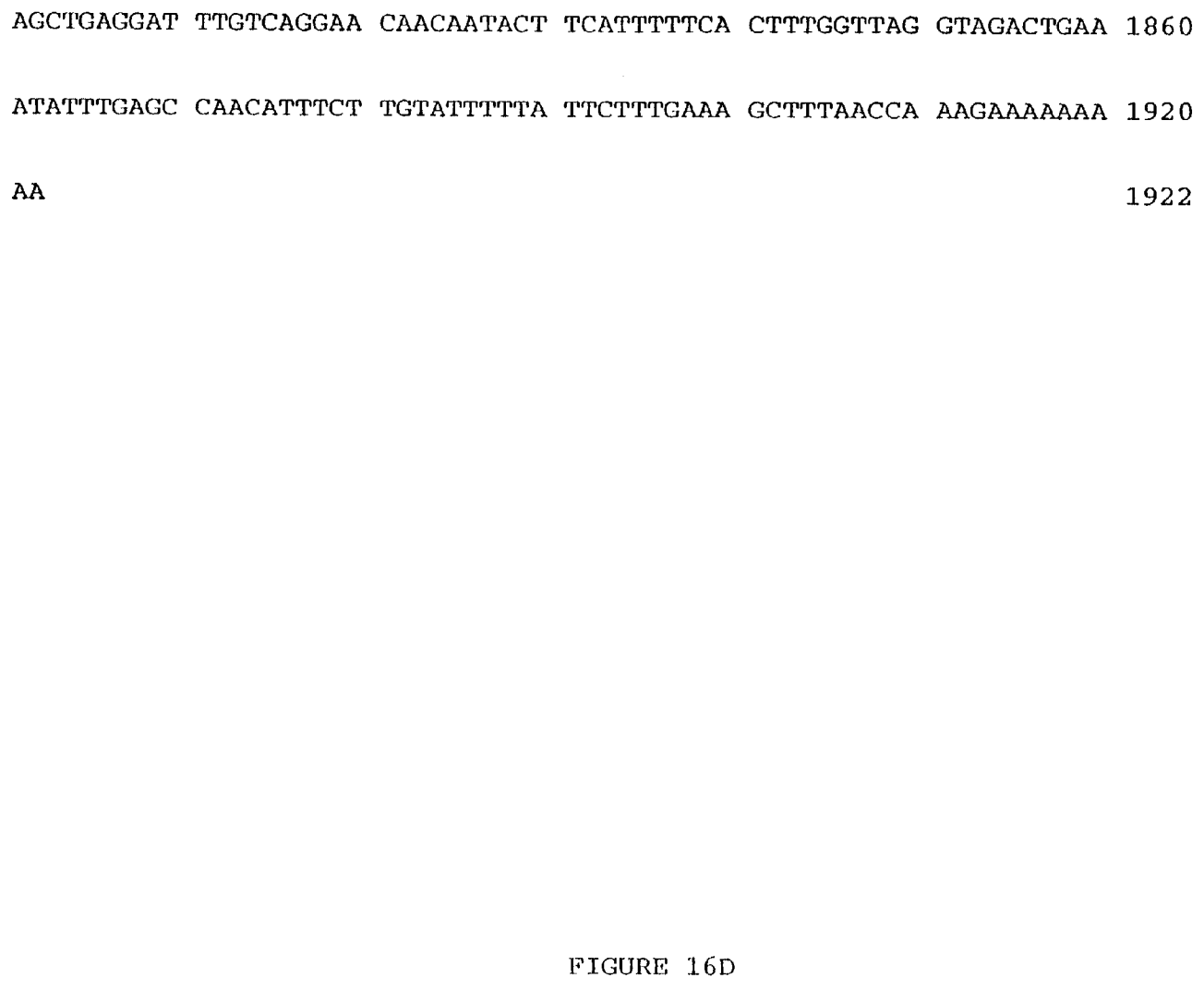

FIGS. 16A, 16B, 16C, and 16D show the nucleic acid sequence of a *Brassica campestris* β-ketoacyl-ACP synthase factor A (46 kD) cDNA clone (SEQ ID NO: 38). Comparison of the translated amino acid sequence to the castor β-ketoacyl-ACP synthase factor A amino acid sequence indicates a possible frame shift mutation in the region near nucleotide 1120.

FIGS. 17A, 17B, 17C, 17D, 17E, and 17F show the nucleic acid sequence (SEQ ID NO: 39) and translated amino acid sequence (SEQ ID NO: 40) of a jojoba fatty acyl reductase cDNA clone.

FIGS. 18A, 18B, 18C, 18D, 18E, and 18F show the nucleic acid sequence (SEQ ID NO: 41) and translated amino acid sequence (SEQ ID NO: 42) of a jojoba wax synthase cDNA clone (SEQ ID NO: 21).

FIGS. 19A, 19B, 19C, and 19D provide approximately 3.4 kb of genomic sequence of Bce4 (SEQ ID NO: 45).

FIG. 20A, 20B, 20C, 20D, 20E, and 20F provide approximately 4 kb of genomic sequence of Ecg 4-4 ACP sequence (SEQ ID NO: 46).

FIGS. 21A, 21B, 21C, 21D, 21E, 21F, 21G, 21H, 21I, 21J, 21K, 21L, and 21M provide a restriction map of cloned pCGN 1-2 (SEQ ID NO: 47) showing the entire napin coding region sequence (SEQ ID NO: 48) as well as extensive 5' upstream and 3' downstream sequences.

SUMMARY OF THE INVENTION

Figure 21B:
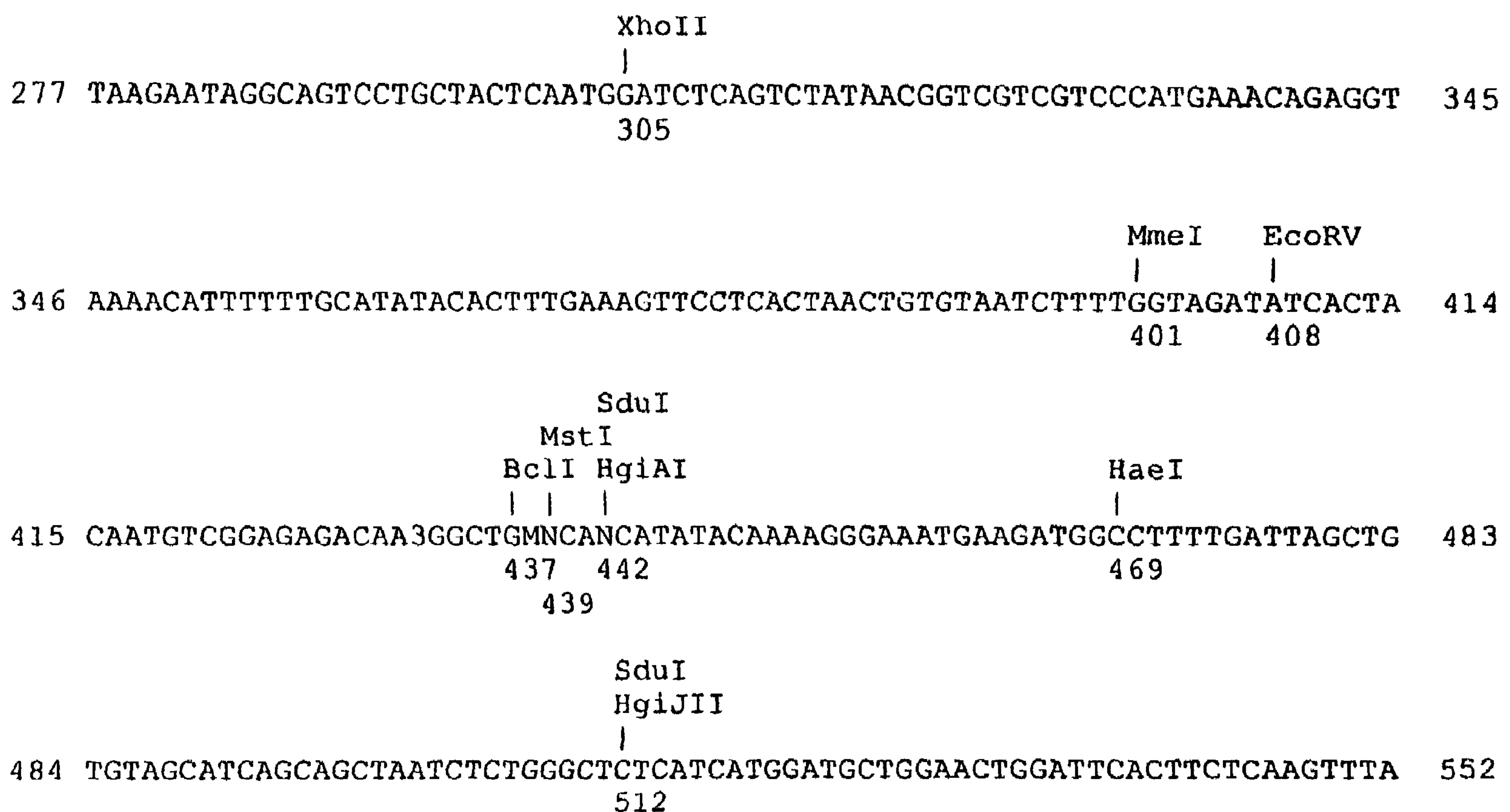

By this invention, modification of the fatty acid composition of a plant seed may be achieved as a result of the activity of a DNA sequence foreign to the plant species to be modified. In particular, it has been found that a plant oil having a modified fatty acid composition can be obtained upon the expression of genes derived from plants of different species than the host plant, upon the expression of genes derived from bacteria, and from the transcription of anti-sense sequences which are complementary to endogenous genes of the plant host cell. In a preferred embodiment, transcription of the fatty acid modifying foreign DNA sequence is restricted to the developing seed tissues.

In brief, the process involves growing plants to seed, where such plants have integrated into their genome a recombinant DNA sequence to be expressed, or in the case of an antisense sequence, to be transcribed, a given foreign fatty acid modifying DNA sequence. Plant seeds and plant seed oils having modified fatty acid compositions may be recovered therefrom, by harvesting mature plant seed and separating a modified oil from the meal of the plant seed. Examples of plant fatty acid modifying traits of interest include, but are not limited to, increase or decrease in level of saturation of the fatty acid, the positioning of any such double bonds, the length of the carbon backbone of the fatty acid, the production of free fatty alcohols and the production of long chain liquid waxes (LCLW). Upon expression in a plant seed, potential fatty acid modifying gene candidates can be verified. For some applications, the expression of more than one fatty acid modifying gene will be desired.

Thus, the present invention is useful for the production of modified plant oils fatty acid compositions including the production of plant oils having a novel fatty acid profile.

DETAILED DESCRIPTION OF THE INVENTION

Methods and compositions are provided for the modification of plant seed oil, particularly modification of the fatty acid composition of such a plant seed oil. The method involves the transcription or transcription and translation of DNA sequences which encode or are complementary to fatty acid modifying enzymes in a growing plant during the development of seed. By this means the oil composition of the resulting plant seed will contain a modified fatty acid profile as compared with a parent plant material which does not contain the fatty acid modifying sequence. In order to reduce effects of the fatty acid modifying sequence on lipid biosynthesis in other tissues outside of the seed storage lipids, the transcription of the DNA sequence may be limited to plant seed tissue.

The foreign DNA sequence shall include any sequence derived from a source different from, i.e., heterologous, to the plant species to be modified. Thus, a plant species which is not capable of sharing genetic material through sexual reproduction with the target plant species for fatty acid modification is a source for DNA sequence to encode a foreign fatty acid modifying enzyme of this invention. Fatty acid modifying genes may also be derived from bacteria. It is now found that the FAS pathway of plants and bacteria are remarkably similar. Despite the wide range of diversity in the composition of plant seed oils which has evolved over time between different plant species and the fundamental differences between fatty acid production and utilization between lower organisms and seed-bearing plants, fatty acid modifying activity may be observed when foreign DNA sequences which encode such traits are introduced and expressed in a plant cell of interest.

The foreign fatty acid modifying DNA sequence shall also include sequences, such as anti-sense, ribozyme or co-suppression (sense) sequences, which can function to modify fatty acid composition of plant seed oils by the reduction of a naturally-occurring plant fatty acid modifying enzyme endogenous to the target host cell. For such applications, the fatty acid modifying sequences may be derived from the plant species to be modified or from a different source so long as the sequence contains sufficient identity (co-suppression) complementarity (anti-sense or ribozyme) to the endogenous sequence. Given the importance of plant lipid biosynthesis to cell viability and the fact that many plant FAS enzymes are active in tissues outside of developing seed tissues, e.g., leaf tissue, certain modifications of endogenous enzyme levels in seed storage tissue may be impossible without the ability to selectively modify the activity of genes which encode such enzymes by tissue type. It is essential to this invention that the transcription of such enzyme reducing DNA sequences have limited impact on plant tissues outside of plant seed tissues. This may be accomplished through the use of weak transcriptional initiation regions or tissue and/or timing specific initiation regions which are discussed in more detail elsewhere.

Fatty acid modified traits of interest include, but are not limited to, chain length, degree of position of saturation and the production of novel fatty acid derivatives or oils. Examples of sources for fatty acid modifying sequences relating to chain length include plant thioesterases (TE) having enzyme specificity toward medium chain fatty acyl groups as shown in the table below:

TABLE 2

| | Plant |
|---|---|
| C8:0/C10:0 | *Cuphea hookeriana* |
| C10:0 | Elm |
| C12:0 | Bay |
| C14:0 | *Cuphea palnstris* |
| C16:0 | Chinese tallow |

Examples of sources for plant fatty acid modifying sequences related to fatty acid saturation are shown below:

TABLE 3

| | |
|---|---|
| Increase 18:1 | Safflower (desaturase) |
| Increase 18:0 | Safflower (oleoyl acyl-ACP thioesterase); Mango, Cacao, Shea nut (stearoyl acyl-ACP thioesterase) |

In addition, traits relating to yield (synthase factors from Castor Bean) or triglyceride position may be of interest. Preliminary results suggest that the #2 position in the triglyceride molecule may be susceptible to ready modification upon alteration of the fatty acyl-CoA pool available for integration. However, for some applications or in order to improve the final product, it may be useful to introduce a Lyso Phosphatidic Acid Acyl Transferase (LPAAT) enzyme activity into the target plant. Of special interest is a lauroyl-LPAAT found in coconut or an erucic-specific LPAAT found in Cuphea or meadowfoam.

Nucleotide sequences encoding or complementary to fatty acid modifying enzymes may be obtained from natural sources or, be partially or wholly artificially synthesized. They may directly correspond to an enzyme endogenous to a natural plant source or contain modified amino acid sequences, such as sequences which have been mutated, truncated, increased or the like. These enzymes and/or their sequences may be obtained by a variety of methods, including but not limited to, partial or homogenous purification of plant extracts, protein modeling, nucleic acid probes, antibody preparations and sequence comparisons. Typically a DNA sequence encoding a plant fatty acid modifying enzyme will be derived in whole or in part from a natural plant source.

Several sequences found in the plant FAS pathway, sequences encoding plant membrane-bound enzymes, and certain bacterial DNA sequences are provided herein. In particular, attention is drawn to the plant DNA sequences provided in FIGS. 1–18. Recombinant DNA constructs containing some of these sequences in binary vectors suitable for the use in the transformation of a plant cell via *Agrobacterium*-mediated transformation have been deposited at the American Type Culture Collection (ATCC), Manassas, Va.:

| | | | |
|---|---|---|---|
| pCGN3B1G | FIG. 5 | ATCC # | 69502 |
| pCGN3231 | FIG. 1 | ATCC # | 69507 |
| pCGN2797 | FIG. 13/FIG. 14 | ATCC # | 69505 |
| pCGN758G | FIG. 17 | ATCC # | 69504 |
| pCGN3242 | FIG. 3 | ATCC # | |
| pCGN3259 | FIG. 15 | ATCC # | |

In addition, a napin expression cassette, pCGN3223, having a napin 5'/convenient cloning sites/napin 3' as also been deposited at the ATCC and assigned accession No. #69503.

In order to express a fatty acid modifying enzyme or to reduce an endogenous fatty acid modifying enzyme by the activity of a foreign gene in a developing plant seed, a plant is grown to seed having a recombinant DNA construct integrated in its genome. The plant having the integrated, foreign DNA itself may have been produced via genetic engineering or may be the descendent of a prior genetically engineered plant. A recombinant construct will have regulatory elements capable of initiating and terminating transcription. Recombinant constructs include both expression cassettes and transcriptional cassettes.

An expression cassette for expression of fatty acid modifying enzyme of interest in a plant cell will include, in the 5' to 3' direction of transcription, a transcription and translation initiation control regulatory region (also known as a "promoter") functional in a plant cell, a nucleic acid sequence encoding the fatty acid modifying enzyme, which may include sequences to result in the reduction of an endogenous fatty acid modifying enzyme such as a sense sequence which results in cosuppression or ribozyme sequences, and a transcription termination region. Numerous transcription initiation regions are available which provide for a wide variety of constitutive or regulatable, e.g., inducible, transcription. Among transcriptional initiation regions used for plants are such regions associated with cauliflower mosaic viruses (35S, 19S), and structural genes such as for nopaline synthase or mannopine synthase or napin and ACP promoters, etc. The transcription/translation initiation regions corresponding to such structural genes are found immediately 5' upstream to the respective start codons. Thus, depending upon the intended use, different promoters may be desired.

Sequences found in an antisense orientation may be found in cassettes which at least provide for transcription of the sequence encoding the fatty acid modifying enzyme. By anti-sense is meant a DNA sequence in the 5' to 3' direction of transcription which encodes a sequence complementary to the sequence of interest. It is preferred that an anti-sense sequence be directly complementary to the plant host. Any transcription initiation region capable of expression in a plant host which causes initiation of high levels of transcription in all storage tissues during seed development is sufficient.

Of special interest in this invention, both in expression cassettes or in constructs designed for the transcription of an anti-sense message, are the use of transcriptional initiation regions which are capable of preferentially transcribing the fatty acid modifying enzyme in seed tissue, in particular, at early stages of seed oil formation. Selective modification of seed fatty acid/oils composition will reduce potential adverse effects to other plant tissues. Examples of such regions include the sequences immediately 5' upstream of a napin or seed ACP genes such as described in U.S. Pat. No. 5,110,728, desaturase genes such as described in Thompson et al (*Proc. Nat. Acad. Sci.* (1991) 88:2578–2582), co-pending U.S. application Ser. No. 07/762,762 filed 9/1691, or Bce-4 gene such as described in co-pending U.S. Ser. No. 494,722, filed Mar. 16, 1990. Alternatively, the use of the 5' regulatory region associated with the plant fatty acid modifying structural gene to be employed, i.e., the region immediately 5' upstream to the plant fatty acid modifying structural gene of interest and/or the transcription termination regions found immediately 3' downstream to the plant fatty acid modifying structural gene, may often be desired. In general, transcription initiation regions will be selected based upon their expression profile which may change given the particular application.

Briefly, Bce4 is found in immature embryo tissue at least as early as 11 days after anthesis (flowering), peaking about 6 to 8 days later or 17–19 days post-anthesis, and becoming undetectable by 35 days post-anthesis. The timing of expression of the Bce4 gene closely follows that of lipid accumulation in seed tissue. Bce4 is primarily detected in seed embryo tissue and to a lesser extent found in the seed coat. Bce4 has not been detected in other plant tissues tested, root, stem and leaves.

The Bcg 4-4 ACP message presents a similar expression profile to that of Bce4 and, therefore, also corresponds to lipid accumulation in the seed tissue. Bcg 4-4 is not found in the seed coat and may show some differences in expression level, as compared to Bce4, when the Bcg 4-4 5' non-coding sequence is used to regulate transcription or transcription and translation of a fatty acid modifying sequence of this invention.

The napin 1-2 message is found in early seed development and thus, also offers regulatory regions which can offer preferential transcriptional regulation of a desired DNA sequence of interest such as the plant desaturase DNA sequence of this invention during lipid accumulation. Napins are one of the two classes of storage proteins synthesized in developing *Brassica* embryos (Bhatty, et al., *Can J. Biochem.* (1968) 46:1191–1197) and have been used to direct tissue-specific expression when reintroduced into the *Brassica* genome (Radke, et al., Theor. Appl. Genet. (1988) 75:685–694). An example of a napin expression cassette, pCGN3223, has been deposited and assigned ATCC #69503.

Regulatory transcript termination regions may be provided in DNA constructs of this invention as well. Transcript termination regions may be provided by the DNA sequence encoding the plant desaturase or a convenient transcription termination region derived from a different gene source, especially the transcript termination region which is naturally associated with the transcript initiation region. The transcript termination region will contain at least about 1 kb, preferably about 3 kb of sequence 3' to the structural gene from which the termination region is derived.

In developing the DNA construct, the various components of the construct or fragments thereof will normally be inserted into a convenient cloning vector which is capable of replication in a bacterial host, e.g., *E. coil*. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species into which the expression construct or components thereof are introduced, one or more markers may be employed, where different conditions for selection are used for the different hosts.

In addition, one may choose to provide for the transcription or transcription and translation of one or more other sequences of interest in concert with the expression or anti-sense of fatty acid modifying sequence. When one wishes to provide a plant transformed for the combined effect of more than one nucleic acid sequence of interest, typically a separate nucleic acid construct will be provided for each. The constructs, as described above contain transcriptional or transcriptional and translational regulatory control regions. One skilled in the art will be able to determine regulatory sequences to provide for a desired timing and tissue specificity appropriate to the final product in accord with the above principles set forth as to the respective expression or anti-sense constructs. When two or more constructs are to be employed, whether they are both related to the same fatty acid modifying sequence or a different fatty acid modifying sequence, it may be desired that different regulatory sequences be employed in each cassette to reduce spontaneous homologous recombination between sequences. The constructs may be introduced into the host cells by the same or different methods, including the introduction of such a trait by crossing transgenic plants via traditional plant breeding methods, so long as the resulting product is a plant having both characteristics integrated into its genome.

Furthermore, in recombinant constructs designed for the expression of a foreign DNA, a transit peptide suitable for the translocation of the target enzyme to the plastid may be needed if the foreign DNA does not already provide for such a sequence or if a different transit peptide sequence is desired, for example, if the transit peptide normally associated with the transcriptional and translational initiation region is to be used.

Depending upon the method of plant transformation to be employed, various intermediates or techniques will be required which are well-known by those of skill in the art. *Agrobacterium*-mediated transformation, DNA particle bombardment, mircroinjection, chloroplast transformation, and the like, are examples of current techniques for the introduction of foreign DNA into a plant cell. The regeneration of whole plants, capable of producing seed, from such transformed tissue is also well known in the art.

In many instances, it will be desirable to have the construct bordered on one or both sides by T-DNA, particularly having the left and right borders, more particularly the right border. This is particularly useful when-the construct uses *A. tumefaciens* or *A. rhizogenes* as a mode for transformation, although the T-DNA borders may find use with other modes of transformation.

Where Agrobacterium is used for plant cell transformation, a vector may be used which may be introduced into the *Agrobacterium* host for homologous recombination with T-DNA or the Ti- or Ri-plasmid present in the *Agrobacterium* host. The Ti- or Ri-plasmid containing the T-DNA for recombination may be armed (capable of causing gall formation) or disarmed (incapable of causing gall formation), the latter being permissible, so long as the vir genes are present in the transformed *Agrobacterium* host. The armed plasmid can give a mixture of normal plant cell and gall.

A preferred method for the use of *Agrobacterium* as the vehicle for transformation of plant cells employs a vector having a broad host range replication system, at least one T-DNA boundary and the DNA sequence or sequences of interest. Commonly used vectors include pRK2 or derivatives thereof. See, for example, Ditta et al., *PNAS USA*, (1980) 77:7347–7351 and EP 0 120 515, which are incorporated herein by reference. Normally, the vector will be free of genes coding for opines, oncogenes and vir-genes. Included with the expression construct and the T-DNA will be one or more markers, which allow for selection of transformed *Agrobacterium* and transformed plant cells. A number of markers have been developed for use with plant cells, such as resistance to chloramphenicol, the aminoglycoside G418, hygromycin, or the like. The particular marker employed is not essential to this invention, one or another marker being preferred depending on the particular host and the manner of construction.

For example, binary plant transformation vectors containing the left and right T-DNA borders of *Agrobacterium tumefaciens* octopine Ti-plasmid pTiA6 (Currier and Nester, supra, the gentamycin resistance gene of pPH1JI (Hirsch and Beringer, supra), an *Agrobacterium rhizogenes* Ri plasmid origin of replication from pLJbB11 (Jouanin et al., supra), a 35S promoter-kanR-tm13' region capable of conferring kanamycin resistance to transformed plants, a ColE1 origin of replication from pBR322 (Bolivar et al., supra), and a lacZ' screenable marker gene from pUC18 (Yanish-Perron et al., supra) have been used successfully. (McBride and Summerfelt, *Plant Molecular Biology* (1990) 14(2): 269–276). The binary vector might then be transformed into *Agrobacterium tumefaciens* strain EHA101 (Hood, et al., *J. Bacteriol.* (1986) 168:1291–1301) as per the method of Holsters, et al., *Mol. Gen. Genet.* (1978) 163:181–187. The explants may be combined and incubated with the transformed *Agrobacterium* for sufficient time for transforipation, the bacteria killed, and the plant cells cultured in an appropriate selective medium. Once callus forms, shoot formation can be encouraged by employing the appropriate plant hormones in accordance with known methods, and the shoots transferred to rooting medium for regeneration of plants. The plants may then be grown to seed, and the seed used to establish repetitive generations and for isolation of vegetable oils compositions.

A variety of stable genetic lines having fixed levels of saturation may be obtained and integrated into a traditional breeding program. Hemizygous and heterozygous lines or homozygous lines may demonstrate different useful properties for oil production and/or breeding. For example, saturation levels may be increased up to 2-fold by the development of homozygous plants as compared with heterozygous (including hemizygous) plants.

For some applications, modified fatty acid compositions may be detected in developing seeds, whereas in other instances, such as for analysis of oil profile, for detection of fatty acid modifications occurring later in the FAS pathway, or for detection of minor modifications to the fatty acid composition, analysis of fatty acid or oil from mature seeds may be preferred. Furthermore, analysis of oil and/or fatty acid content of individual seeds may be desirable, especially in detection of oil modification in the segregating T1 seed populations. As used herein, T1 indicates the plant and seed arising from transformation/regeneration protocols described herein. T2 indicates plants and seeds generated from the transgenic T1 seed.

Once a transgenic plant is obtained which is capable of producing seed having a modified fatty acid composition, traditional plant breeding techniques, including methods of mutagensis, may be employed to further manipulate the fatty acid composition. Alternatively, additional foreign fatty acid modifying DNA sequence may be introduced via genetic engineering to further manipulate the fatty acid composition. It is noted that the method of transformation is not critical to this invention. However, the use of genetic engineering plant transformation methods, i.e., the power to insert a single desired DNA sequence, is critical. Heretofore, the ability to modify the fatty acid composition of plant oils was limited to the introduction of traits that could be sexually transferred during plant crosses or viable traits generated through mutagenesis. Through the use of genetic engineering techniques which permits the introduction of inter-species genetic information and the means to regulate the tissue-specific expression of endogenous genes, a new method is available for the production of plant seed oils with modified fatty acid compositions. In addition, there is the potential for the development of novel plant seed oils upon application of the tools described herein.

Any seed-bearing plant may be employed as the target plant species for fatty acid modification in accordance with this invention, including angiosperms, gymnosperms, monocotyledons, and dicotyledons. Plants of special interest are crops harvested for seed oils, including but not limited to, rapeseed (High Erucic Acid Rape and canola), corn, soybean, safflower, sunflower, cotton, peanut, oil palm and Cuphea.

As to sources for foreign fatty acid modifying DNA sequences, any plant, bacterial or fungal species is of interest. In some cases, a DNA sequence endogenous to the target plant species for fatty acid modification will be desired for the construction of a recombinant DNA construct having the sequence in an anti-sense orientation. In other cases, DNA sequences of interest will be derived from plant species other than the target crop for fatty acid seed oil modification. By "derived" is therefore included sequences found in recombinant DNA constructs since they are isolated from the native source of the DNA sequence. Also considered within the class of "derived" sequences are sequences which display greater than 70% base pair identity with the original sequence, without including conservative base changes, modifications and/or deletions of transit peptide regions, or the alteration of a DNA sequence from a non-plant source to reflect plant preferred codons.

Of particular interest are unusual fatty acids or unusual fatty acid profiles found in seed storage lipids. Such plant sources provide the opportunity to elucidate the mechanism involved in the production of such fatty acids and provide the means to obtain such a fatty acid modifying DNA sequence.

In addition, other organisms such as bacteria can provide access to DNA sequences which encode proteins having fatty acid modifying properties in plants as well. Although bacteria do not store lipid reserves, these organisms have evolved many genes encoding functions in fatty acid and lipid metabolism, i.e., membrane lipids. It has been known that some bacterial genes encode sequences which can interact in vitro with plant cell free extracts; however, by this invention bacterial derived fatty acid modifying DNA sequences may be able to interact with plant fatty acid synthesis enzyme systems, such that the various specialized activities provided by these sequences may be used in plant genetic engineering techniques to provide novel plant seed fatty acid compositions.

Bacteria have developed divergent pathways for biosynthesis of saturated and unsaturated fatty acids, as well as specialized genes for fatty acid modification. For example, the production of unsaturated fatty acids in *E. coli* is catalyzed by the action of β-hydroxydecanoyl thioester dehydrase. Sequence of the dehydrase has been published (Cronan, et al., *J. Biol. Chem.* (1988) 263:4641–4646). Thus, isolation of this gene and insertion into a target plant host for modification of the fatty acid elongation pathway is desired. Other bacterial genes of interest include those encoding acyl transferase activity, such as the *Vibrio harvei* luxD gene, which find use for production of C14 free fatty acids in plant cells (Miyamoto et al., *J. Biol. Chem.* (1988) 262:13393–13399). For methods to increase the overall content of fatty acids produced in plant cells, it is desired to increase the number fatty acid chain elongation events. The *E. coli* synthase III gene (Tsay et al., *J. Biol. Chem.* (1992) 267:6807–6814) may find use in this manner to provide an increase in the amount of fatty acid produced in the plant cell.

In addition, various species of bacteria, such as *Acinetobacter* (Fixter et al. (1986) *J. Gen. Microbiol.* 132:3147–3157) and *Micrococcus* (Lloyd (1987) *Microbios* 52:29–37), and also the unicellular organism, Euglena (Khan and Kolattukudy (1975) *Arch. Biochem. Biophys.* 170:400–408), are capable of modifying fatty acids by the action of a reductase enzyme to produce fatty alcohols. Such fatty alcohols may be further modified in conjunction with another fatty acid molecule for production of waxes by the action of the wax synthase enzymes found in such organisms. The genes encoding these reductase and wax synthase proteins may be obtained from the various organisms and transferred to plant cells for modification of plant fatty acids.

Once a putative plant fatty acid modifying candidate is identified, enzyme activity may be tested in a plant cell-free system to determine if any fatty acid modifying properties can be observed. In situations when the fatty acid modifying sequence is in hand, recombinant constructs can be provided to express the protein of interest in a readily transformable systems such as *E. coli*. Evidence of fatty acid modification in the *E. coli* and/or introducing the transformed cell system to a plant cell extract may provide information regarding fatty acid modifying properties of the sequence.

Desaturases

A plant desaturase of this invention includes any sequence of amino acids, such as a protein, polypeptide, or peptide fragment, obtainable from a plant source which is capable of catalyzing the insertion of a first double bond into a fatty acyl-ACP moiety in a plant host cell, i.e., in vivo, or in a plant cell-like environment, i.e. in vitro. "A plant cell-like environment" means that any necessary conditions are available in an environment (i.e., such factors as temperatures, pH, lack of inhibiting substances) which will permit the enzyme to function. In particular, this invention relates to enzymes which add such a first double bond at the ninth carbon position in a fatty acyl-ACP chain. There may be similar plant desaturase enzymes of this invention with different specificities, such as the Δ-12 desaturase of carrot.

By increasing the amount of desaturase available in the plant cell, an increased percentage of unsaturated fatty acids may be provided; by decreasing the amount of desaturase, an increased percentage of saturated fatty acids may be provided. (Modifications in the pool of fatty acids available for incorporation into triglycerides may likewise affect the composition of oils in the plant cell.) Thus, an increased expression of desaturase in a plant cell may result in increased proportion of fatty acids, such as one or more of palmitoleate (C16:1), oleate (C18:1), linoleate (C18:2) and linolenate (C18:3) are expected. In rapeseed, increased desaturase expression lowers stearate and total saturates. Of special interest is the production of triglycerides having increased levels of oleate. Using anti-sense technology, alternatively, a decrease in the amount of desaturase available to the plant cell is expected, resulting in a higher percentage of saturates such as one or more of laurate (C12:0), myristate (C14:0), palmitate (C16:0), stearate (C18:0), arachidate (C20:0), behenate (C22:0) and lignocerate (C24:0). In rapeseed reduced desaturase results in increased stearate levels and total saturates. Of special interest is the production of triglycerides having increased levels of stearate or palmitate and stearate. In addition, the production of a variety of ranges of such saturates is desired. Thus, plant cells having lower and higher levels of stearate fatty acids are contemplated. For example, fatty acid compositions, including oils, having a 10% level of stearate as well as compositions designed to have up to an appropriate 60% level of stearate or other such modified fatty acid(s) composition are contemplated.

Oils with increased percentages of stearate, especially rapeseed triglyceride oils, are provided herein. Increased stearate percentages (by weight) ranging from native up to 25 fold are described. By manipulation of various aspects of the DNA constructs (e.g., choice of promoters, number of copies, etc.) and traditional breeding methods, one skilled in the art may achieve even greater levels of stearate. By combination of the plant desaturase sequence in combination with other DNA sequences, a variety of other fatty acid compositions and triglycerides can be achieved in rapeseed and other plant species.

Oilseed containing stearate rich fatty acids having the majority incorporated into triglyceride oils will contain a certain percentage of triglycerides of the following formula:

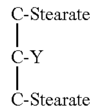

wherein Y is an unsaturated fatty acid. In certain triglycerides, Y shall be oleate. Triglyceride oils with stearate-unsaturate-stearate (S-U-S) and/or stearate-oleate-stearate (S-O-S) may be novel oils compositions, particularly in oilseed varieties which naturally contain low stearate levels. Such triglyceride oils may find special application in the production of non-hydrogenated margarines, for example. Edible oils having naturally low stearate levels include canola (rapeseed), sunflower, peanut, safflower, coconut and oil palm, (See, Table I.)

DNA sequence of *C. tinctorius* desaturase gene (FIG. 1) is provided, as well as DNA sequences of desaturase gene from a *Ricinus* (FIG. 2) a *Brassica* (FIG. 3) and a *Simmondsia* (FIG. 4) plant.

Thioesterases

A plant thioesterase of this invention includes any sequence of amino acids, such as a protein, polypeptide or peptide fragment obtainable from a plant source which demonstrates the ability to catalyze the production of free fatty acid(s) from fatty acyl-carrier substrates under plant enzyme reactive conditions. By "enzyme reactive conditions" is meant that any necessary conditions are available in an environment (i.e., such factors as temperature, pH, lack of inhibiting substances) which will permit the enzyme to function.

Preferential activity of a plant thioesterase toward a particular chain-length fatty acyl-carrier substrate is determined upon comparison of free fatty acid product amounts obtained per different chain length substrates. For example, by "C12 preferring" is meant that the hydrolytic activity of the enzyme preparation demonstrates a preference for lauroyl, and perhaps decanoyl, over other substrates of different acyl carbon lengths. In a like fashion, a plant thioesterase having "C10 preferring" activity will show higher levels of activity toward decanoyl substrates, and perhaps octanoyl, over other substrates of different acyl carbon lengths. It is noted that some activity, of a significantly lesser magnitude, may be observed against other chain-length fatty acyl substrates, i.e., the specificity will be substantial, but may not be absolute.

As noted above, a plant thioesterase of this invention will display activity toward fatty acyl-carrier substrates. During biosynthesis of lipids in a plant cell, fatty acids are typically covalently bound to ACP or coenzyme A (CoA) carriers. Plant thioesterases which display preferential activity toward acyl-ACP substrates are especially preferred because they are likely to be closely associated with the FAS pathway in immature embryo plastids. However, activity toward acyl-CoA substrates or other synthetic substrates, for example, is also contemplated herein.

Plant thioesterases exemplified herein include an *Umbellularia californica* (Bay), *Cuphea hookeriana* (Cuphea), *Brassica campestris* and elm and *Carthamus tinctorius* (safflower) thioesterases as found in FIGS. 5–12. These exemplified thioesterases may be used to obtain other plant thioesterases of this invention.

Synthases

A plant synthase of this invention includes any sequence of amino acids, polypeptide, peptide fragment or other protein preparation, whether derived in whole or in part from natural or synthetic sources which demonstrates the ability to catalyze a condensation reaction between an acyl-ACP or acyl-CoA having a chain length of $C_2$ to $C_{16}$ and malonyl-ACP in a plant host cell. A plant synthase will be capable of catalyzing a synthase reaction in a plant host cell, i.e., in vivo, or in a plant cell-like environment, i.e., in vitro. Typically, a plant synthase will be derived in whole or in part from a natural plant source.

In addition, synthase from other sources such as bacteria or lower plants, may also be useful in plants and thus be considered a plant synthase in this invention. For example, the *E. coli* synthase protein encoded by the fab B gene is shown herein to have homology to plant synthase proteins.

Synthase I demonstrates preferential activity towards acyl-ACPs having shorter carbon chains, $C_2$–$C_{14}$; synthase II demonstrates preferential activity towards acyl-ACPs having longer carbon chains, $C_{14}$–$C_{16}$. Synthase III demonstrates preferential activity towards acyl-CoAs having very short carbon chains, $C_2$ to $C_6$. Other plant synthases may also find applicability by this invention, including synthase III type activities. Differences between synthases I, II, and III are also observed in inhibition with cerulenin. Synthase I is most sensitive, synthase II less sensitive and synthase III the least sensitive to cerulenin.

Thus, over-expression of synthase I could serve to increase fatty acid yield, and/or the proportion of palmitic acids (C16:0) found in the system. Alternatively, as a critical enzyme in several fatty acid elongation steps, reducing endogenous synthase I might effectively provide low yields of fatty acids. As the last enzyme in the fatty acid elongation pathway, synthase II may be a critical factor to increase production of fatty acids. Increased availability of synthase II to FAS may in effect "drive" the rate of reaction forward and result in a larger pool of long chain fatty acids. In turn, the presence of an increased amount of fatty acids with 18 carbons may result ultimately, in the increased production of triglycerides. In a like manner, the decrease of synthase II may work to decrease one or both of these mechanisms. Because synthase II catalyzes final elongation steps, it may require support from other synthase factors to create the desired effect. In particular, the combined presence of synthase I and synthase II are contemplated for the generation of a high composition of oleic fatty acids and/or increased triglyceride production. In addition, the production of palmitate may be further enhanced by a combination of increased synthase I production and reduction in endogeous synthase II. Thus, various synthase factors may be combined in a like fashion to achieve desired effects.

Protein purification and *E. coli* expression studies indicate that two protein factors may be required to provide synthase II activity. In substantially purified castor synthase preparations, synthase II activity was found only when both the synthase 50 kD (factor B) and 46 kD (factor A) were present in the preparation. *E. coli* expression studies confirm the contribution of the factor A protein to synthase II activity. Analysis of similar castor preparations having synthase I activity, reveals the presence of a single malor 50 kD protein band. Thus, synthase I activity may require the presence of only the synthase factor B protein, or a combination of synthase factor B proteins (such as a dimer). Thus, transcription (either sense or antisense) of a single synthase factor sequence or a combination of synthase sequences are both desirable for modification of plant fatty acids.

One may wish to integrate nucleic acids encoding a desaturase sense sequence and synthase sense sequence into the genome of a host cell. A plant desaturase includes any enzyme capable of catalyzing the insertion of a first double bond into a fatty acid-ACP moiety, especially Δ-9 desaturase. Such a combination may be designed to modify the production of unsaturated fatty acids and thus either lead to significantly lower or higher saturated fat upon the expression of both enzymes in a plant host cell. As desaturase acts upon the longer chain fatty acyl-ACPs, the resulting product of synthase II activity, various applications are possible. Of interest is the combination of an enhanced production of both synthase II and Δ-9 desaturase for the production of fatty acids having little or no completely saturated chains. It may also be of interest to provide for the increased production of synthase II and a decreased production of desaturase for the production of high stearate (C18:0) fatty acid compositions. The modified pool of saturated/unsaturated fatty acids may be reflected in the composition of resulting triglycerides. In a different embodiment, it may be desired to combine the increased expression of a synthase, such as synthase I, with a medium-chain plant thioesterase. Plants containing a medium-chain plant thioesterase, an enzyme capable of having preferential hydrolase activity toward one or more medium-chain (C8 to C14) acyl-ACP substrates, are contemplated for the production of medium chain fatty acids, especially laurate (C12:0). In combination with an increased level of one or more synthases, these effects may be augmented.

Of special interest are synthases obtainable from *Ricinus communis* such as provided in FIGS. 13 and 14, and synthases from Brassica (FIGS. 15 and 16).

Reductases

A fatty acyl reductase of this invention includes any sequence of amino acids, such as protein, polypeptide or peptide fragment, which is active in catalyzing the reduction of a fatty acyl group to the corresponding alcohol. By fatty acyl group is intended any fatty acyl group, covalently bound to a carrier, such as ACP or coenzyme A.

Other enzymes may or may not be required for the reduction of the fatty acyl group to the alcohol, as this enzymatic reaction involves a 4 electron reduction which may be carried out in two steps. In the first step, the acyl group may be converted to an aldehyde, which would then be reduced to the corresponding alcohol. Thus, the reductase of this invention may be active through the entire 4 electron reduction, from acyl to alcohol, or may catalyze the reduction to the aldehyde, which is then further reduced to the alcohol by a second enzyme. The fatty acyl reductase of this invention is also referred to hereafter as "reductase."

Thus, this invention includes uses of seed-plant fatty acyl reductases which convert fatty acyl groups to alcohols. More particularly, this invention relates to NADPH-dependent reductases. In addition, it is noted that a plant fatty acyl reductase of this invention may have activity towards both fatty acyl-CoA or fatty acyl-ACP molecules, and the activity observed may depend upon the substrate available. However, preferential activity toward very long chain acyl-CoA substrates is desired for manipulation of the fatty acid synthetase (FAS) acyl-CoA elongation pathway. Sequence of a jojoba reductase having such long chain activity is provided in FIG. 17. Evidence indicates that this single reductase protein carries out the complete reduction of acyl CoA to alcohol.

Wax Synthases

A wax synthase or fatty acyl-CoA:fatty alcohol acyltransferase of this invention includes any sequence of amino acids, such as protein, polypeptide or peptide fragment, which is active in catalyzing the esterification of a fatty alcohol by a fatty acyl group to produce a wax ester. The acyl-CoA:alcohol acyltransferase of this invention is also referred to hereafter as "ligase" or "wax synthase."

Although typically referred to as an acyl-CoA:alcohol acyltransferase, the wax synthases of this invention may demonstrate activity towards a variety of acyl substrates, including fatty acyl-CoA and fatty acyl-ACP molecules. In addition, both the acyl and alcohol substrates acted upon by the wax synthase may have varying carbon chain lengths and degrees of saturation, although the wax synthase may demonstrate preferential activity towards certain molecules.

Many different organisms produce wax esters from alcohol and acyl substrates and are desirable sources of the fatty acyl reductase and wax synthase proteins of this invention. For example, plants produce epidermal, or cuticular wax (Kolattukudy (1980) in *The Biochemistry of Plants* (Stumpf, P. K. and Conn, E. E., eds.) Vol.4, p. 571–645), and the desert shrub, jojoba, produces a seed storage wax (Ohlrogge et al. *Lipids* (1978) 13:203–210). Wax synthesis has also been observed in various species of bacteria, such as *Acinetobacter* (Fixter et al. (1986) *J. Gen. Microbiol.* 132:3147–3157) and *Micrococcus* (Lloyd (1987) *Microbios* 52:29–37), and by the unicellular orgnanism, *Euglena* (Khan and Kolattukudy (1975) *Arch. Biochem. Biophys.* 170:400–408). In addition, wax production and wax synthase activity have been reported in microsomal preparations from bovine meibomian glands (Kolattukudy et al. (1986) *J. Lipid Res.* 27:404–411), avian uropygial glands, and various insect and marine organisms. Consequently, many different wax esters which will have various properties may be produced by the wax synthases of this invention, and the activity of the enzyme and type of wax ester produced may depend upon the available substrate or the substrate specificity of the particular wax synthase of interest.

Of particular interest is a jojoba wax synthase protein (E.C.2.3.1.75) of approximately 57 kD. Nucleic acid sequence and translated amino acid sequence of the jojoba wax synthase cDNA are provided in FIG. 18.

In conjunction with wax synthase sequences, it is desirable to provide the target host cell with the ability to produce fatty alcohols from the fatty acyl molecules present in the host cells. As discussed above, fatty acyl reductases are desirable for such uses. Thus, by providing the wax synthase and the fatty acyl reductase proteins to the host plant cell, wax esters may be produced from the fatty alcohol and fatty acyl substrates.

Other nucleic acid sequences "homologous" or "related" to DNA sequences encoding other fatty acid modifying sequences within the scope of this invention may be obtained from the sequences provided. "Homologous" or "related" includes those nucleic acid sequences which are identical or conservatively substituted as compared to the exemplified sequences of this invention or from an enzyme sequence which has in turn been obtained from a fatty acid modifying enzyme of this invention. By conservatively substituted is meant that codon substitutions encode the same amino acid, as a result of the degeneracy of the DNA code, or that a different amino acid having similar properties to the original amino acid is substituted. One skilled in the art will readily recognize that antibody preparations, nucleic acid probes (DNA and RNA) sequences encoding and the like may be prepared and used to screen and recover such enzymes from other plant sources. Typically, nucleic acid probes are labeled to allow detection, preferably with radioactivity although enzymes or other methods may also be used. For immunological screening methods, antibody preparations either monoclonal or polyclonal are utilized. Polyclonal antibodies, although less specific, typically are more useful in gene isolation. For detection, the antibody is labeled using radioactivity or any one of a variety of second antibody/enzyme conjugate systems that are commercially available. Examples of some of the available antibody detection systems are described by Oberfilder (Focus (1989) BRL Life Technologies, Inc., 11:1–5)

A "homologous" or "related" nucleic acid sequence will show at least about 60% homology, and more preferably at least about 70% homology, between the known desaturase sequence and the desired candidate enzyme of interest, excluding any deletions which may be present. Homology is determined upon comparison of sequence information, nucleic acid or amino acid, or through hybridization reactions. Amino acid sequences are considered homologous by as little as 25% sequence identity between the two complete mature proteins. (See generally, Doolittle, R. F., of URFS and ORFS, University Science Books, Calif.; 1986.)

Oligonucleotide probes can be considerably shorter than the entire sequence, but should be at least about 10, preferably at least about 15, more preferably at least 20 nucleotides in length. When shorter length regions are used for comparison, a higher degree of sequence identity is required than for longer sequences. Shorter probes are often particularly useful for polymerase chain reactions (PCR), especially when highly conserved sequences can be identified. (See, Gould, et al., *PNAS USA* (1989) 86:1934–1938.) Longer oligonucleotides are also useful, up to the full length of the gene encoding the polypeptide of interest. When longer nucleic acid fragments are employed (>100 bp) as probes, especially when using complete or large cDNA sequences, one would screen with low stringencies (for example 40–50° C. below the melting temperature of the probe) in order to obtain signal from the target sample with 20–50% deviation, i.e., homologous sequences. (See, Beltz, et al., *Methods in Enzymology* (1983) 100:266–285.) Both DNA and RNA probes can be used.

When the desired enzyme is from a plant source, a genomic library may be prepared and then probed with conserved sequences to identify homologously related sequences. Use of the entire cDNA may be employed if shorter probe sequences are not identified. Positive clones are then analyzed by restriction enzyme digestion and/or sequencing. When a genomic library is used, one or more sequences may be identified providing both the coding region, as well as the transcriptional regulatory elements of the fatty acid modifying gene from such plant source. In this general manner, one or more sequences may be identified providing both the coding region, as well as the transcriptional regulatory elements of the gene from such plant source.

In use, probes are typically labeled in a detectable manner (for example with $^{32}$P-labeled or biotinylated nucleotides) and are incubated with single-stranded DNA or RNA from the plant source in which the gene is sought, although unlabeled oligonucleotides are also useful. Hybridization is detected by means of the label after single-stranded and double-stranded (hybridized) DNA or DNA/RNA have been separated, typically using nitrocellulose paper or nylon membranes. Hybridization techniques suitable for use with oligonucleotides are well known to those skilled in the art.

Various oils modifications may be achieved in the practice of the present method. The ability to affect the position and/or number of double bonds in the fatty acid molecule or the length of the fatty acid molecules which are produced in the seed are of specific interest. Additionally, the positions in which such modified fatty acids are incorporated into the triglyceride backbone are also of interest. There is some evidence that incorporation into the triglyceride backbone is a function of the fatty acid pools; however, some enzymes have been identified which are associated with the insertion of a fatty acid into a particular sequence.

The invention now being generally described, it will be more readily understood by reference to the following examples which are included for purposes of illustration only and are not intended to limit the present invention.

EXAMPLES

Example 1

Identification of Fatty Acid Modification Sequences 1.1. Cell-Free Extracts

Cell-free extracts may be used to screen potential fatty acid modifying enzymes. One method is described in U.S. Pat. No. 5,147,792, issued Sep. 15, 1992, which is hereby incorporated by reference.

1.2 Expression in *E. coli*

Once a putative fatty acid modifying DNA sequence is obtained, expression in *E. coli* may be desired to verify that the sequence does in fact encode for the desired enzyme activity. In some instances, the desired activity of the enzyme will be recognizable from a modified phenotype in the *E. coli*. In some instances, further analysis will be required, for example, addition to a cell-free extract as described in 1.1, to verify the enzyme.

Example 2

Modified Fatty Acid Composition via Expression of a Foreign Plant Enzyme 2.1. Modification of Fatty Acid Chain Length 2.1.1. Produce C12:0—Bay MCFA A DNA sequence encoding for *Umbellularia californica*, also known as "Bay," C12:0-ACP thioesterase is found in FIG. 5.

pCGN3816 (ATTC #), a napin 5'/thioesterase/napin 3' binary vector construct was prepared and used to transform *Brassica napus* plants in accordance with methods known in the art.

Seeds from *Brassica napus* plants transformed with pCGN3816 are analyzed for total fatty acids. Analysis of single segregating seeds from T2 transformed plants reveals levels of C12:0 ranging from zero to 14.5%, as compared to zero percent in seeds from untransformed control plants. C12:0 levels correlate to C12:0-ACP thioesterase activities in corresponding immature seeds. In addition, C14:0 is also detected in these seeds at levels correlating with those of the C12:0, although C14:0 levels are lower.

2.1.2. Produce C8/C10:0—Cuphea MCFA

A partial DNA sequence encoding for *Cuphea hookeriana*, also known as "Cuphea," C8:0/C10:0-ACP thioesterase is found in FIG. 11. A complete DNA sequence may be obtained as follows:

For sequences 3' to the PCR fragment, the RACE procedure of Frohman et al., (*Proc. Nat. Acad. Sci.* (1988) 85:8998–9002) is utilized. Briefly, cDNA is generated from cuphea endosperm poly(A)+RNA using 200 ng of RNA, a poly(T) oligonucleotide (with 5' restriction recognition sites for EcoRI, XhoI and SalI) and reverse transcriptase. The product of this reaction is used in a PCR 3' RACE with an oligonucleotide encoding EcoRI, XhoI and SalI recognition sites and an oligonucleotide from the cuphea gene fragment. The reaction is run in a Biosycler oven with the following program:

| | |
|---|---|
| 1 cycle at: | 94° C. for 40 sec. |
| | 50° C. for 2 min. |
| | 72° C. for 40 min. |
| 40 cycles at: | 94° C. for 40 sec. |
| | 50° C. for 2 min. |
| | 72° C. for 3 min. |

In this manner, an approximately 700 bp fragment representing the 3' portion of the cuphea thioesterase gene sequence is obtained.

In addition, 5' sequence of the cuphea thioesterase encoding sequence may also be obtained using PCR. For this reaction, cDNA to cuphea endosperin poly(A)+RNA is generated using random hexamer oligonucleotide primers in a reverse transcription reaction essentially as described by Frohman et al. (supra). The cDNA product of this reaction is A-trailed using terminal deoxynucleotide transferase and used in PCR. The reaction is run in a Biosycler oven with the following program:

| | |
|---|---|
| 34 cycles at: | 94° C. for 1 min. |
| | 55° C. for 1.5 min. |
| | 72° C. for 2.5 min. |

In this manner, an approximately 450 bp fragment representing the 5' portion of the cuphea thioesterase gene sequence is obtained.

The various camphor thioesterase gene fragments are combined in a convenient cloning vector using restriction sites as inserted from the PCR procedures.

Once a sequence encoding an active enzyme is obtained, recombinant DNA construct capable of directing the expression of the cuphea thioesterase in a plant during seed development may be prepared. Transformation and regeneration of the target host plant is performed according to techniques known in the art. Seed is recovered from the transgenic plant and an increased amount of C8:0 and/or C10:0 is detected.

2.1.3. Produce C10:0—Elm MCFA

A partial DNA sequence encoding for Ulmaceae also known as "elm," C10:0-ACP thioesterase is found in FIG. 12. A complete DNA sequence may be obtained as described with respect to cuphea in 2.1.2.

Once a sequence encoding an active enzyme is obtained, recombinant DNA construct capable of directing the expression of the elm thioesterase in a plant during seed development may be prepared. Transformation and regeneration of the target host plant is performed according to techniques known in the art. Seed is recovered from the transgenic plant and an increased amount of C10:0 is detected.

2.2. Modification of Fatty Acid Saturation 2.2.1. Increase C18:1—Safflower Desaturase A DNA sequence encoding for *Carthamus tinctorius* (safflower) stearoyl-acyl ACP desaturase is found in FIG. 1.

pCGN3231 (ATCC #), a napin 5'/desaturase/napin 3' binary vector construct was prepared and used to transform *Brassica napus* plants (var. Delta) in accordance with methods known in the art.

Preliminary analysis of developing seeds indicated no significant change in fatty acid (total seed lipid) composition of the transformed pCGN3231 Delta plants with respect to the control plants. This result appeared consistent with the low levels of safflower mRNA observed in transgenic plants as compared to levels of endogenous Brassica desaturase. However, subsequent fatty acid analysis of individual mature seeds of Delta plants containing the pCGN3231 construct showed an average of 0.97±0.16% stearate compared with an average of 1.47±0.24% obtained from seed testing of 2 different Delta control plants. Individual seeds showed as little as 0.8% stearate and a saturate content (16:0+18:0) as low as 4.9%.

2.2.2. Increase C18:0'Safflower Long Chain Thioesterase

DNA sequences encoding for C18:0-preferring *Carthamus tinctorius* (safflower) acyl-ACP thioesterases are found in FIGS. 7 and 8. The safflower thioesterases demonstrate activity towards C18:1, as well as C18:0 ACP. Although C18:1 substrate is preferred by both enzymes, the 5-2 clone (FIG. 8) demonstrates a broader specificity for 16:0 and 18:0 substrates. A recombinant DNA construct capable of directing the expression of the long chain thioesterases in a plant during seed development may be prepared similar to the construct described in 2.2.1. Transformation and regeneration of the target host plant is performed according to techniques known in the art. Seed is recovered from the transgenic plant and an increased ratio of C18:0 as compared with C18:1 is detected.

2.2.3. Increase C18:1—Castor Synthases

DNA sequence encoding for βketoacyl-ACP synthase activities are in FIG. 14 (synthase factor A) and FIG. 13 (synthase factor B). pCGN2797 (ATCC #), a binary vector construct containing a napin 5'/synthase factor A/napin 3' and napin 5'/factor B/napin 3', was prepared and used to transform *Arabidposis thaliana* plants in accordance with methods known in the art.

Seeds from 15 *Arabidopsis* plants transformed with the pCGN2797 construct were analyzed for the presence of *R. communis* synthase proteins. Five of these plants test positive, by Western analysis, for expression of the 50 kD *R. communis* synthase factor B protein. Cross-reactivity of the *R. communis* synthase factor A polyclonal antibody with the corresponding *Brassica* synthase protein, prevents detection of this synthase protein by Western analysis.

Two of the plants which tested positive for expression of the 50 kD *R. communis* synthase protein, transformants #5 and #6 have been analyzed to determine the fatty acid composition of their seeds. Several non-expressing transformants and a non-transformed control were similarly analyzed. Seed fatty acid composition analysis is determined by the acid methanolysis method according essentially as described by Browse et al., *Anal. Biochem.* (1986) 152: 141–145. Briefly, 100 seeds of each sample are treated with 1 ml of 5% $H_2SO_4$ in MeOH and heated in a 90° C. water bath for two hours to convert the fatty acids to fatty acid methyl esters (FAMEs). An internal standard (C17:0) is added to each sample (250 ml of a 1 mg/ml solution in toluene) prior to the heating step. The samples are allowed to cool, after which 1 ml 0.9% NaCl in $H_2O$ is added to aid in phase separation. Hexane (250 ml to each vial) is added to extract the FAMEs, and the samples are then vortexed and centrifuged to separate the phases. The hexane layer is removed and transferred to a GC autosampler for injected on the GC. A useful GC temperature program for these analyses is as follows: 200° C. for zero minutes, followed by a 5 degrees per minute temperature ramp to a final temperature of 250° C., which is held for 6 minutes. Data is reported as % of total fatty acids in Table 4.

2.3. Production of Free Fatty Alcohols & LCLW 2.3.1. Produce Free Fatty Alcohols—Jojoba Reductase A DNA sequence encoding for jojoba fatty acyl reductase is found in FIG. 17. pCGN7586 (ATCC #), a napin 5'/reductase/napin 3' recombinant DNA construct was prepared and used to transform *Arabidopsis thaliana* plants in accordance with methods known in the art.

Developing seeds from *Arabidopsis* plants transformed with the pCGN7586 napin/reductase construct, are analyzed for reductase activity. Out of fifteen plants analyzed, eleven were found to have reductase enzyme activity, with specific activities ranging from 5 to 30 pmol/min/mg protein. Western analysis demonstrates that the amount of reductase present in transgenic *Arabidopsis* embryos is approximately 0.01% of total protein. Lipids are extracted from mature seeds, derivatized (Browse et al. supra) and analyzed for alcohol content by GC as described above. These analyses reveal the presence of 20:1 alcohol in 3 of the transformed Arabidopsis plants.

2.3.2. Produce LCLW—Jojoba Wax Synthase

A DNA sequence encoding for jojoba wax synthase enzyme (E.C. 2.3.1.75), also sometimes referred to as a "ligase," is found in FIG. 18. The translational start and stop codons are identified. A recombinant DNA construct capable of directing the expression of the wax synthase may be prepared similar to the construct described in 2.3.1. Transformation and regeneration of the target host plant is performed. Either through transformation or plant breeding, a transgenic plant is produced additionally containing a construct as described in 2.3.1. Seed is recovered from the dual construct containing transgenic plant and the presence of long chain liquid wax molecules are detected. Note, the substitution of a different seed-specific promoter, i.e., Bce-4, than as used for the regulatory control of the fatty acyl reductase may be desired.

TABLE 4

| | 12:0 % | 14:0 % | 16:0 % | 16:1 % | 18:0 % | 18:1 % | 18:2 % | 18:3 % | 20:0 % | 20:1 % | 20:2 % | 22:0 % | 22:1 % | 22:2 % | 24:0 % | SATS % |
|---|---|---|---|---|---|---|---|---|---|---|---|---|---|---|---|---|
| SAMPLE: | | | | | | | | | | | | | | | | |
| 1 | 0.03 | 0.08 | 6.22 | 0.24 | 3.11 | 18.10 | 25.36 | 18.56 | 2.44 | 21.16 | 1.81 | 0.34 | 2.21 | 0.10 | 0.23 | 12.44 |
| 3 | 0.08 | 0.09 | 6.08 | 0.24 | 3.02 | 18.62 | 25.21 | 18.75 | 2.26 | 21.21 | 1.70 | 0.31 | 2.09 | 0.12 | 0.21 | 12.06 |
| 5 | 0.09 | 0.07 | 3.95 | 0.20 | 2.77 | 17.68 | 27.99 | 18.82 | 2.30 | 20.58 | 2.13 | 0.35 | 2.69 | 0.16 | 0.21 | 9.74 |
| 6 | 0.01 | 0.07 | 4.59 | 0.18 | 3.15 | 20.95 | 25.30 | 17.71 | 2.28 | 21.33 | 1.75 | 0.32 | 2.04 | 0.09 | 0.22 | 10.64 |
| 9 | 0.01 | 0.08 | 5.85 | 0.25 | 2.89 | 19.24 | 25.98 | 17.46 | 2.23 | 21.43 | 1.80 | 0.33 | 2.14 | 0.14 | 0.19 | 11.57 |
| 10 | 0.11 | 0.12 | 6.63 | 0.33 | 3.14 | 16.48 | 27.66 | 17.07 | 2.71 | 20.59 | 2.16 | 0.38 | 2.24 | 0.14 | 0.24 | 13.33 |
| 11 | 0.07 | 0.08 | 6.01 | 0.24 | 3.04 | 19.43 | 24.93 | 17.86 | 2.36 | 21.47 | 1.81 | 0.32 | 2.07 | 0.09 | 0.21 | 12.10 |
| 12 | 0.01 | 0.08 | 5.91 | 0.21 | 3.09 | 19.98 | 24.28 | 18.84 | 2.23 | 21.16 | 1.59 | 0.33 | 2.02 | 0.09 | 0.18 | 11.83 |
| 15 | 0.01 | 0.07 | 5.88 | 0.20 | 3.22 | 20.85 | 24.05 | 18.72 | 2.30 | 20.83 | 1.59 | 0.30 | 1.75 | 0.06 | 0.16 | 11.94 |
| CONTROL: | | | | | | | | | | | | | | | | |
| | 0.01 | 0.09 | 6.33 | 0.28 | 3.12 | 18.15 | 25.77 | 19.37 | 2.35 | 19.85 | 2.00 | 0.35 | 2.00 | 0.11 | 0.21 | 12.47 |

Seeds from transformant #5 contain 3.95% C16:0, and seeds from #6 have a 4.59% C16:0. Seeds from the non-expressing transformants and the non-transformed control had C16:0 percentages ranging from 5.85 to 6.63%. Total saturated fatty acids in seeds from #5 were 9.74%, compared to 12.47% total saturated fatty acids for seeds from the non-transformed control and a range of 11.57%–13.33% total saturated fatty acids for seeds from the non-expressing transformants. The total saturated fatty acid level in transformant #6 is 10.64%.

2.4. Expression Cassettes with Seed-Specific Promoters

ACP Expression Cassette

In this example, the preparation of an ACP expression cassette containing a plant desaturase is described.

An expression cassette utilizing 5'- upstream sequences and 3'-downstream sequences obtainable from *B. campestris* ACP gene can be constructed as follows.

A 1.45 kb XhoI fragment of Bcg 4-4 (FIG. 20) containing 5'-upstream sequences is subcloned into the cloning/sequencing vector Bluescript+ (Stratagene Cloning Systems, San Diego, Calif.). The resulting construct, pCGN1941, is digested with XhoI and ligated to a chloramphenicol resistant Bluescript M13+ vector, pCGN2015 digested with XhoI pCGN2015 is prepared as described for pCGN2016 except that the EcoRI/HindIII "chloramphenicol" fragment isolated from pCGN2008 is ligated with the 2273 bp fragment of Bluescript KS+ (Stratagene; La Jolla, Calif.) isolated after digestion with DraI. This alters the antibiotic resistance of the plasmid from penicillin resistance to chloramphenicol resistance. The chloramphenicol resistant plasmid is pCGN1953.

3'-sequences of Bcg 4-4 are contained on an SstI/BglII fragment cloned in the SstI/BamHI sites of M13 Bluescript+ vector. This plasmid is named pCGN1940. pCGN1940 is modified by in vitro site-directed mutagenesis (Adelman et al., *DNA* (1983) 2:183–193) using the synthetic oligonucleotide 5'-CTTAAGAAGTAACCCGGGCTGCAGTTTTAGTATTAAGAG-3' (SEQ ID NO: 27) to insert SmaI and PstI restriction sites immediately following the stop codon of the reading frame for the ACP gene nucleotides from the SstI site. The 3'-noncoding sequences from this modified plasmid, pCGN1950, are moved as a PstI-SmaI fragment into pCGN1953 cut with PstI and SmaI. The resulting plasmid pCGN1977 comprises the ACP expression cassette with the unique restriction sites EcoRV, EcoRI and PstI available between the 1.45 kb 5' and 1.5 kb of 3'-noncoding sequences for the cloning of genes to be expressed under regulation of these ACP gene regions.

Desaturase cDNA sequences from pCGN2754 (*C. tinctorius*) are inserted in the ACP expression cassette, pCGN1977, as follows. pCGN2754 is digested with HindIII (located 160 nucleotides upstream of the start codon) and Asp718 located in the polylinker outside the poly(A) tails. The fragment containing the coding region for desaturase was blunt-ended using DNA polymerase I and ligated to pCGN1977 and digested with EcoRV. A clone containing the desaturase sequences in the sense orientation with respect to the ACP promoter is selected and called pCGN1895. This expression cassette may be inserted into a binary vector, for example, for *Agrobacterium*-mediated transformation, or employed in other plant transformation techniques.

Bce-4 Expression Cassette

In this example, the preparation of a Bce-4 expression cassette containing a plant desaturase is described.

The desaturase cDNA clone from pCGN2754 is modified by in vitro mutagenesis to insert restriction sites immediately upstream of the ATG start codon and downstream of the TGA stop codon. A single-stranded template DNA is prepared for the mutagenesis reaction from pCGN1894 (described in Example 6) as described by Messing (*Methods in Enzymol.* (1983) 101:20–79). Synthetic oligonucleotides are synthesized on an Applied Biosystems 380A DNA synthesizer. The oligonucleotides used are 5'-CCATTTTTGATCTTCCTCGAGCCCGGGCTGCAGTTCTTCTTCTTCTTG-3' (SEQ ID NO: 28) for the 5'mutagenesis and 5'-GCTCGTTTTTTTTTCTCTGCAGCCCGGGCTCGAGTCACAGCTTCACC-3' (SEQ ID NO 29) for the 3'-mutagenesis; both add PstI, SmaI and XhoI sites flanking the coding region. Both oligonucleotides are 5'-phosphorylated (BRL 5'-Terminus labelling kit) and used for mutagenesis with the pCGN1894 template by the procedure of Adelman et al. (*DNA* (1983) 2:183–193). Alternatively, the desired restriction sites may be inserted by PCR, using the 3' oligo described above and another oligo, 5' ACTGACTGCAGCCCGGGCTCGAGGAAGATCAAAAATGGCTCTTC 3' (SEQ ID NO: 30) for the 3' and 5' primers, respectively. The template in this polymerase chain reaction is DNA from pCGN1894. The XhoI fragment from the resulting clone can be subcloned into the Bce4 expression cassette, pCGN1870 at the unique XhoI site. This Bce4/desaturase expression cassette can then be inserted in a suitable binary vector, transformed into *Agrobacterium tumefaciens* and used to transform plants.

pCGN1870 is a Bce-4 expression cassette containing 5' and 3' regulatory regions of the Bce-4 gene and may be derived from the Bce-4 sequence found in pCGN1857, which was deposited with the ATCC on Mar. 9, 1990, and has designation 68251, or by methods known to one skilled in the art from the sequence provided in FIG. 19.

The Bce-4 gene may be isolated as follows: The ClaI fragment of pCGN1857, containing the Bce4 gene is ligated into ClaI digested Bluescript KS+ (Stratagene; La Jolla, Calif.), producing pCGN1864. Single stranded DNA is made from pCGN1864 and altered by in vitro mutagenesis using the oligonucleotides

```
BCE45P:                                  (SEQ ID NO:31)
5' GAGTAGTGAACTTCATGGATCCTCGAGGTCTTGAAAACCTAGA 3'
and

BCE43P:                                  (SEQ ID NO:32)
5' CAATGTCTTGAGAGATCCCGGGATCCTTAACAACTAGGAAAAGG 3'
```

as described by Adelman et al. (*DNA* (1983) 2:183–193). The oligonucleotide BSCP2 (5' GTAAGACACGACTTATCGCCACTG 3' (SEQ ID NO: 33)) complementary to a portion of Bluescript, is included in the reaction to improve the yield of double-stranded DNA molecules. The resulting plasmid, pCGN1866, contains XhoI and BamHI sites (from BCE45P) immediately 5' to the Bce-4 start codon and BamHI and SmaI sites (from BCE43P) immediately 3' to the Bce-4 stop codon. The ClaI fragment of pCGN1866, containing the mutagenized sequences, is inserted into the ClaI site of pCGN2016, producing pCGN1866C. The ClaI fragment of pCGN1866C is used to replace the corresponding wild-type ClaI fragment of pCGN1867 to produce pCGN1868. Bce-4 coding sequences are removed by digestion of pCGN1868 with BamHI and recircularization of the plasmid to produce pCGN1870. The Bce-4 expression cassette, pCGN1870, contains 7.4 kb of 5' regulatory sequence and 1.9 kb of 3' regulatory sequence derived from the Bce-4 genomic clone separated by the cloning sites, XhoI, BamHI, and SmaI. Desaturase sequences in sense or anti-sense orientation may be inserted into the cassette via the cloning sites and the resulting construct may be employed in a plant transformation technique.

Napin 1-2 Expression Cassette

In this example, the preparation of a napin 1-2 expression cassette containing a plant desaturase is described.

An expression cassette utilizing 5' upstream sequences r and 3' downstream sequences obtainable from *B. campestris* napin gene can be constructed as follows.

Figure 21F:
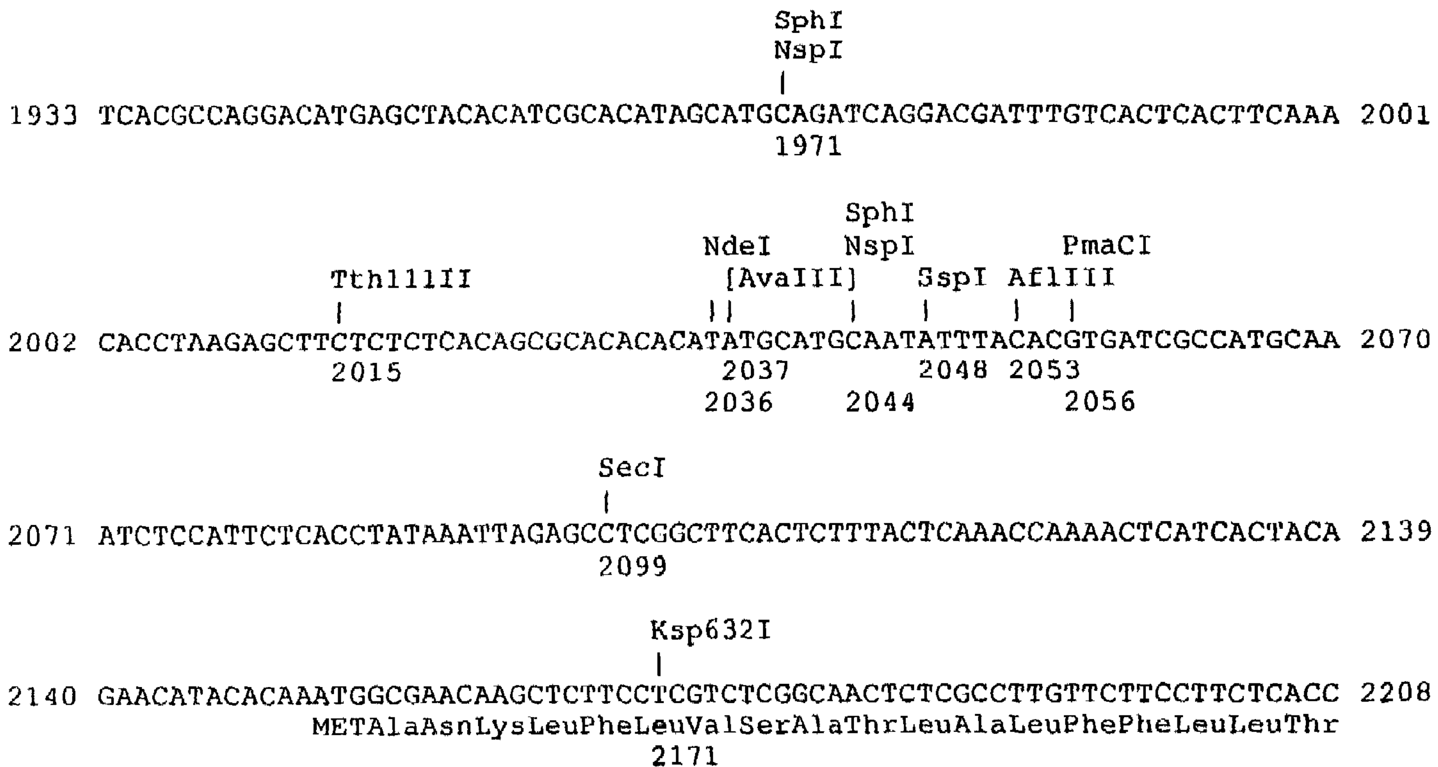
Figure 21I:
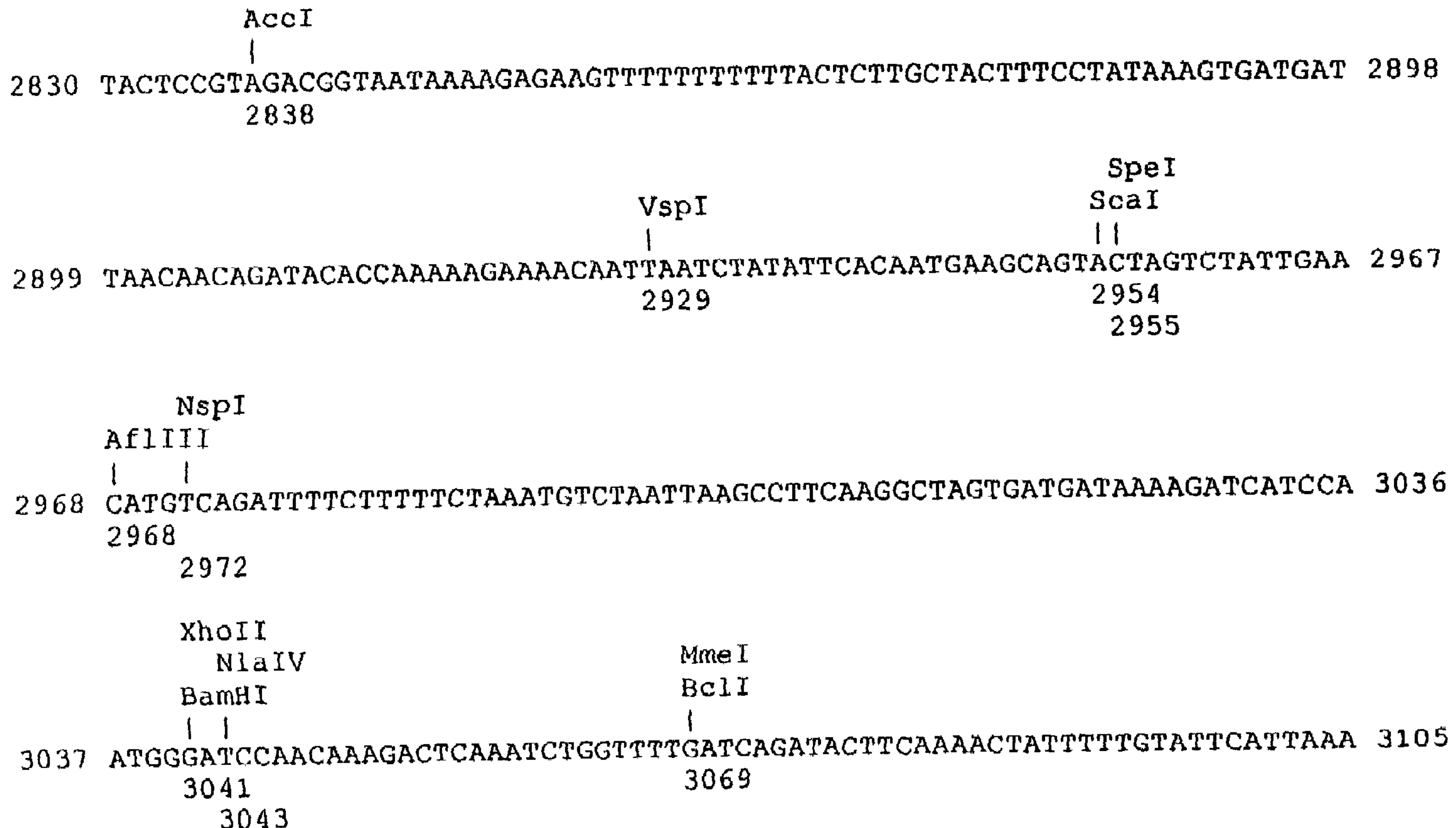
Figure 21M:
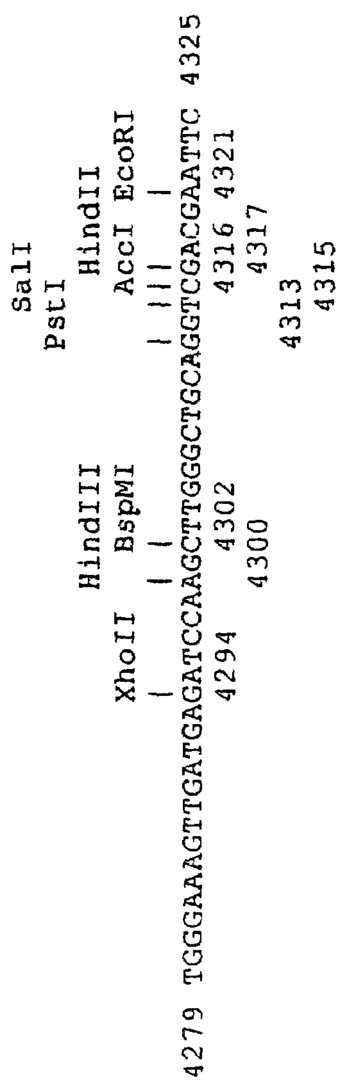

A 2.7 kb XhoI fragment of napin 1-2 (FIG. 21) containing 5' upstream sequences is subcloned into pCGN789, a pUC based vector the same as pUC119, with the normal polylinker replaced by the synthetic linker 5' GGAATTCGTCGACAGATCTCTGCAGCTCGAGGGATCCAAGCTT 3' (SEQ ID NO: 34), which represented the polylinker EcoRI, SalI, BglII, PstI, XhoI, BamHI, HindIII, and results in pCGN940. The majority of the napin coding region of pCGN940 was deleted by digestion with SalI and religation to form pCGN1800. Single-stranded DNA from pCGN1800 was used in an in vitro mutagenesis reaction (Adelman et al., *DNA* (1983) 2:183–193) using the synthetic oligonucleotide 5' GCTTGTTCGCCATG-CATATCTTCTGTATGTTC 3' (SEQ ID NO: 35). This oligonucleotide inserted an EcoRV and an NcoI restriction site at the junction of the promoter region and the ATG start codon of the napin gene. An appropriate mutant was identified by hybridization to the oligonucleotide used for the mutagenesis and sequence analysis and named pCGN1801.

A 1.7 kb promoter fragment was subcloned from pCGN1801 by partial digestion with EcoRV and ligation to pCGN786 (a pCGN566 chloramphenicol based vector with the synthetic linker described above in place of the normal polylinker) cut with EcoRI and blunted by filling in with DNA polymerase I Klenow fragment to create pCGN1802.

A 2.1 kb SalI fragment of napin 1-2 (FIG. 21) containing 3' downstream sequences is subcloned into pCGN789 (described above) and results in pCGN941. pCGN941 is digested with XhoI and HindIII and the resulting approximately 1.6 kb of napin 3' sequences are inserted into XhoI-HindIII digested pCGN1802 to result in pCGN1803. In order to remove a 326 nucleotide HindIII fragment inserted opposite to its natural orientation, as a result of the fact that there are 2 HindIII sites in pCGN1803, the pCGN1803 is digested with HindIII and religated. Following religation, a clone is selected which now contains only 1.25 kb of the original 1.6 napin 3' sequence. This clone, pCGN1808 is the napin 1-2 expression cassette and contains 1.725 kb of napin promoter sequences and 1.265 kb of napin 31 sequence with the unique cloning sites SalI, BglI, PstI and XhoI in between.

Alternatively, pCGN1808 may be modified to contain 25 flanking restriction sites to allow movement of only the expression sequences and not the antibiotic resistance marker to binary vectors such as pCGN1557 (McBride and Summerfelt, supra). Synthetic oligonucleotides containing KpnI, NotI and HindIII restriction sites are annealed and ligated at the unique HindIII site of pCGN1808, such that only one HindIII site is recovered. The resulting plasmid, pCGN3200 contains unique HindIII, NotI and KpnI restriction sites at the 3'-end of the napin 3'-regulatory sequences as confirmed by sequence analysis.

The majority of the napin expression cassette is subcloned from pCGN3200 by digestion with HindIII and SacI and ligation to HindIII and SacI digested pIC19R (Marsh, et al. (1984) *Gene* 32:481–485) to make pCGN3212. The extreme 5'-sequences of the napin promoter region are reconstructed by PCR using pCGN3200 as a template and two primers flanking the SacI site and the junction of the napin 5'-promoter and 15 the pUC backbone of pCGN3200 from the pCGN1808 construct.

The forward primer contains ClaI, HindIII, NotI, and KpnI restriction sites as well as nucleotides 408-423 of the napin 5'-sequence (from the EcoRV site) and the reverse primer contains the complement to napin sequences 718–739 which include the unique SacI site in the 5'-promoter. The PCR was performed using a Perkin Elmer/Cetus thermocycler according to manufacturer's specifications. The PCR fragment is subcloned as a blunt-ended fragment into pUC8 (Vieira and Messing (1982) *Gene* 19:259–268) and digested with HincII to give pCGN3217. Sequence of pCGN3217 across the napin insert verifies that no improper nucleotides were introduced by PCR. The napin 5'-sequences in pCGN3217 are ligated to the remainder of the napin expression cassette by digestion with ClaI and SacI and ligation to pCGN3212 digested with ClaI and SacI. The resulting expression cassette pCGN3221, is digested with HindIII and the napin expression sequences are gel purified away and ligated to pIC20H (Marsh, supra) digested with HindIII. The final expression cassette is pCGN3223, which contains in an ampicillin resistant background, essentially identical 1.725 napin 5' and 1.265 3' regulatory sequences as found in pCGN1808. The regulatory regions are flanked with HindIII, NotI and KpnI restriction sites and unique SalI, BglIII, PstI, and XhoI cloning sites are located between the 5' and 3' noncoding regions.

Desaturase sequences in sense or antisense orientation may be inserted into a napin expression cassette via the cloning sites. The resulting construct may be employed for plant transformation. For example, one of ordinary skill in the art could also use known techniques of gene cloning, mutations, insertion and repair to allow cloning of a napin expression cassette into any suitable binary vector, such as pCGN1557 (described above) or other similar vectors.

Example 3

Modified Fatty Acid Composition via Expression of a Non-Plant Enzyme 3.1. Modification of Chain Length 3.1.1. Increase C14:0—Vibrio Constructs for expression of the *Vibrio harvei* myristoyl ACP thioesterase in plant cells which utilize napin promoter regions are prepared as follows: Two 100 base oligos are synthesized:

```
HARV-S:                                   (SEQ ID NO:43)
5' CGG TCT AGA TAA CAA TCA ATG CAA GAC TAT TGC ACA
CGT GTT GCG TGT GAA CAA TGG TCA GGA GCT TCA CGT
CTG GGA AAC GCC CCC AAA AGA AAA CGT G 3'

HARV-A:                                   (SEQ ID NO:44)
5' ATA CTC GGC CAA TCC AGC GAA GTG GTC CAT TCT TCT
GGC GAA ACC AGA AGC AAT CAA AAT GGT GTT GTT TTT
AAA AGG CAC GTT TTC TTT TGG GGG CGT T 3'
```

The two oligos contain 20 bp of complementary sequence for annealing. A TAQ polymerase extension reaction utilizing the two oligos yields a 180 bp product. The oligos consist essentially of luxD gene sequence with sequence changes introduced to remove 3 potential poly A addition sites and to alter 5 nucleotides to change the codon preference from bacteria to plants. All changes are conservative; i.e. the amino acid sequence is not altered.

The 180 bp TAQ polymerase extension product is blunted and cloned into Bluescript. The approximately 180 bp luxD fragment is then removed from Bluescript by digestion with XbaI and EaeI and cloned in frame with the EaeI/XbaI fragment from the Vibrio CDNA clone, containing the remainder of the luxD gene, by 3-way ligation into XbaI/XhoI digested Bluescript SK. The luxD gene is removed, by digestion with XbaI and partial digestion with PstI and cloned in frame with the safflower thioesterase transit peptide encoding region into a napin expression cassette. The napin 5'/safflower transit:myristoyl ACP thioesterase/napin 3' fragment is cloned into KpnI/BamHI digested pCGN1557 (McBride and Summerfelt, supra) for plant transformation.

The resulting transgenic plants are grown to seed and analyzed to determine the percentage of C14 fatty acids produced as the result of insertion of the bacterial acyl transferase gene.

3.2. Modification of Fatty Acid Saturation 3.2.1.Increase Unsaturated Fatty Acids—Dehydrase The enzyme 3-hydroxydecanoyl-[acyl-carrier-protein] dehydratase (EC 4.2.1.60), also referred to herein as "dehydrase," catalyzes the dehydration of 3-hydroxydecanoyl-ACP (C10:0-ACP) to 2-decenoyl-ACP (C10:0-ACP), a key step in the production of unsaturated fatty acids in bacteria. Expression of this enzyme in plant seeds is useful for production of unsaturated medium-chain acyl-ACPs in plants. This gene may be used in conjunction with a plant medium-chain acyl-ACP thioesterase gene for the production of unsaturated medium-chain fatty acids. In the absence of such medium-chain thioesterases, the C10:1-ACP product may be elongated by the native plant fatty acid synthesis enzymes to provide increased amounts of unsaturated long-chain fatty acids.

A useful construct for expression of dehydrase in plants provides for expression of the enzyme in plant seed tissue under control of a napin promoter region. In addition, a transit peptide region is provided for translocation of the dehydrase enzyme into plastids.

A dehydrase nucleic acid sequence from the *E. coli* dehydrase gene (Cronan et al. (1988) *J. Biol. Chem.* 263: 4641–4646) is constructed, which encodes all but the initial Met amino acid of the dehydrase enzyme. A PCR DNA fragment which encodes the safflower thioesterase transit peptide and 6 amino acids of the mature safflower thioesterase (from clone 2-1) is inserted immediately 5' to the dehydrase such that the transit peptide and dehydrase sequences are in the same reading frame. The safflower thioesterase transit/dehydrase sequence is inserted into the napin expression cassette, pCGN3223 (ATTC # ), between the 5' and 3' napin regulatory sequences.

The dehydrase expression construct is transformed into a binary construct for plant transformation. Where re-transformation of transgenic plants which produce medium-chain acyl-ACP fatty acids as the result of an inserted bay thioesterase construct, a selectable marker other than that used in the initial transformation is preferred. For example, hygromycin or kanamycin binary vectors may be used.

Seeds of transgenic plants produced in this manner are analyzed to determine their fatty acid composition. When used in conjunction with a medium-chain thioesterase capable of hydrolyzing medium-chain unsaturated fatty acids, production of such fatty acids is observed. When used in transformation of wild-type oilseed plants, increased production of either medium- or long-chain fatty acids is observed.

3.3. Modification of Fatty Acid Yield 3.3.1. Increase Fatty Acid Elongation Events—Synthase III To increase the overall yield of fatty acids produced in plant cells, fusion constructs of the bacterial synthase III encoding sequence and various plant transit peptide encoding sequences are prepared. These constructs are then used for generation of transgenic plants, wherein the bacterial synthase is incorporated into the chloroplasts for increasing the amount of enzyme available for the first reaction leading to plant fatty acid synthesis.

A fusion of the *Brassica* ACP transit peptide encoding sequence from a *B. rapa* (formerly *campestris*) seed ACP cDNA (Rose et al. (1987) *Nuc. Acids Res.* 15:7197) and the β-ketoacyl-acyl carrier protein synthase III gene (fabH) from *E. coli* K-12 (Tsay et al. (1992) *J. Biol Chem.* 267: 6807–6814), is prepared as follows. The *B. rapa* ACP transit peptide encoding region plus the 5' untranslated sequence is obtained by PCR, wherein the oligonucleotide primers are designed such that an BamHI site is added immediately 5' to the XhoI site at the 5' end of the *B. rapa* cDNA clone, and an NheI site is inserted immediately 3' to the cysteine codon at the 3' end of the transit peptide encoding region. The fabH encoding region is obtained by PCR from *E. coli* DNA, with oligonucleotide primers designed such that an NheI site is inserted immediately 5' to the N-terminal methionine codon, and XhoI and SmaI sites are inserted immediately 3' to the TAG stop codon. The NheI site adds an alanine and serine encoding region immediately 5' to the fabH N-terminal methionine. An ACP transit:synthase III fragment is obtained by ligation at the inserted NheI restriction sites.

Additional ACP/synthase III fusion constructs may be prepared which include various portions of the ACP mature protein encoding region in addition to the ACP transit peptide encoding region. In addition to the ACP transit peptide, various other plant transit peptides are known in the art, and may be used in a similar manner. For example, transit peptides from the plant fatty acid biosynthesis genes described herein may be used.

The transit peptide:synthase III fusion constructs are inserted into an appropriate cassette in position for regulatory control under transcriptional initiation regions which function in plant cells, and in particular in plant seed embryo cells.

Example 4

Modified Fatty Acid Composition via Reduction of an Endogenous Plant Enzyme 4.1. Modification of Fatty Acid Saturation 4.1.1. Increase C18:0—Anti-Sense Brassica Desaturase A DNA sequence encoding for *Brassica campestris* stearoyl acyl-ACP desaturase is found in FIG. 3. pCGN3242 (ATCC #), a napin 5'/desaturase/napin 3' recombinant DNA construct was prepared and used to transform *Brassica campestris* plants (var. Tobin) and *Brassica napus* plants (var. A112) in accordance with methods known in the art.

Due to the self-incompatibility of *Brassica campestris* cv. Tobin, individual transgenic plants were pollinated using non-transformed Tobin pollen. Because of this, the T2 seeds of a transgenic plant containing the antisense desaturase at one locus would be expected to segregate in a 1:1 ratio of transformed to non-transformed seed. The fatty acid composition (total seed lipids) of ten individual seeds collected at 26 days post-anthesis from several pCGN3242-transformed plants and one non-transformed control was analyzed by gas chromatography according to the method of Browse, et al., *Anal. Biochem.* (1986) 152:141–145. One transformant, 3242-T-1, exhibits a fatty acid composition that differed distinctly from controls on preliminary analysis. The control Tobin seeds contained an average of 1.8% 18:0 (range 1.5%–2.0%) and 52.9% 18:1 (range 48.2%–57.1%). T2 seeds of 3242-T-1 segregated into two distinct classes. Five seeds contained levels of 18:0 ranging from 1.3% to 1.9% and levels of 18:1 ranging from 42.2% to 58.3%. The other five seeds contained from 22.9% to 26.3% 18:0 and from 19.9% to 26.1% 18:1.

Analysis of individual mature seeds containing pCGN3242 in T2 seed yielded seed having up to 45% stearate by weight. No changes in the level of palmitate, the precursor to stearate, are observed. Increased percentages of 18:3 are low, but increased levels of long chain (>18 carbon) saturated fatty acids are seen. Reductions in the average total oil content observed in these seed may account for noted decreases in germination rates.

A dramatic increase in stearate composition was observed in mature self-pollinated seeds of a transformed plant (3242-A-3), from 1.8% to 39.8%. Increased stearate was accompanied by a decreased percentage of 18:1 and an increased percentage of 18:1, 18:3 and long chain saturated fatty acids. T2 seed from the 3242-A-3 plant yielded a somewhat continuous range of percent stearate in individual seeds up to 45% stearate. Oil content of high stearate 3242-A112 seed is variable, some seeds having over 30% stearate also have an oil content comparable to control A112 seeds. Segregation and Southern analysis indicate that in 3242-A-3 three functional T-DNA inserts are seen. Independent segregation of multiple antisense genes displaying various levels of expression may account for the range of stearate levels observed.

Mature T2 seeds of *Brassica campestris* cv. Tobin containing pCGN3242 were crushed and 250 μg of C17:0 triglyceride in 250 μg of toluene was added as an internal standard. The seeds were extracted with 1 ml of a 3:2 hexane/isopropanol mixture, dried down, and resuspended in 100 μl to make uniform solvent concentrations in each sample. 20μl of each sample was placed on a silica gel TLC plate (Baker-flex Silica Gel 1B2, 20×20 cm, 200μm thick) and run to the top with 100 ml of a 60:40 hexane/diethyl ether/acetic acid solvent system. 50μg of standards containing tri-, di-, and monoglycerides, as well as free fatty acid were run in adjacent lanes, and can be visualized by spraying these lanes with 10% phoshomolybdic acid in methanol. After heating the spray lanes in an oven, these spots were used as a reference to cut out the non-visualized spots in the sample lane. The plant pieces containing TAG were extracted with 3 ml of 3:2 hexane/isopropanol, dried down and analyzed for fatty acid content by the acidic methanolysis method of Browse et al. (supra). The analyses demonstrated a triglycerol fatty acid composition substantially unchanged, including stearate content, from that observed in analysis of total seed lipids.

Some abnormalities have been observed in some transgenic *Brassica rapus* cv. Delta and Bingo and *Brassica campestris* cv. Tobin plants containing pCGN3234, a recombinant DNA construct having the antisense desaturase DNA sequence under the regulatory control of a constitutive promoter. Specifically, the construct contains a CaMV 35S 5' and a tml 3'. The results suggest that constitutively expressive anti-sense desaturase may interfere with plant growth. These effects could be due to the constitutive expression of antisense desaturase RNA from the 35S promoter (i.e., perhaps providing undesirable leaf lipid compositions) or could be due to the transformation/tissue culture regime the plants have been subjected to, as examples.

4.1.2. Increase C16:0—Anti-Sense Synthase "B"

A DNA sequence encoding for *Brassica campestris* β-keto acyl-ACP synthase factor B is found in FIG. 15. A binary vector construct containing a napin 5'/anti-sense synthase factor B/napin 3', pCGN3259 (ATCC #) was prepared and used to transform *Brassica campestris* (var. Tobin) according to techniques known in the art. Oil analysis of mature single seeds from the resulting plants (Browse et al., supra) reveals seed oil with reduced stearate content.

4.2.Modification of Fatty Acid Length 4.2.1. Produce C12:0—Anti-Sense Brassica Long Chain TE+Bay A DNA sequence encoding for a *Brassica campestris* long chain acyl-ACP thioesterase is found in FIG. 10. A DNA construct capable of directing the transcription of this sequence in an antisense orientation may be prepared similar to the construct described in 4.1.1. Transformation and regeneration of the target host plant is performed. Either through transformation or plant breeding, a transgenic plant is produced additionally containing a medium-chain fatty acyl-ACP thioesterase, for example as found in 2.1.1. Seed is recovered from the dual-construct containing transgenic plant and an increased amount of C12:0 is detected.

It is evident from the above results that it is possible to modify the fatty acid composition of plant seed oils through the expression of foreign enzymes or the reduction of endogenous enzymes. In this manner, various oils profiles may be achieved, including plant oils which were never before possible.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for obtaining a plant seed having a modified fatty acid saturation, said method comprising: growing a transgenic predominantly unsaturated temperate zone oilseed crop plant species to seed, wherein said plant comprises a recombinant DNA construct integrated into the genome of its cells, wherein said recombinant DNA construct comprises a transcriptional initiation region obtained from a plant gene which is expressed preferentially in plant seed tissue, and wherein said construct provides for a nucleic acid sequence encoding a bacterial or foreign plant fatty acid saturation modifying enzyme to be expressed in said plant seed; and harvesting a plant seed having a modified fatty acid saturation, as compared to the fatty acid saturation of seeds from an untransformed parent of said predominantly unsaturated temperate zone oilseed crop plant species, where said fatty acid saturation modifying enzyme is beta-ketoacyl-ACP synthase, wherein said predominantly unsaturated temperate zone oilseed crop plant is selected from the group consisting of corn, soybean, rapeseed, canola, safflower, sunflower, peanut, and cotton.

2. The method according to claim 1 wherein said plant seed tissue is developing plant seed tissue.

3. The method of claim 1 wherein said construct further comprises a selectable marker.

4. The method of claim 1 wherein said construct further comprises a T-DNA.

5. The method of claim 1 wherein said plant is a dicotyledenous plant.

6. The method of claim 1 wherein said plant is a *Brassica* plant.

7. The method of claim 6 wherein said *Brassica* plant is a *Brassica napus* or *Brassica campestris* plant.

8. A method for obtaining a plant seed oil having a modified fatty acid saturation said method comprising: growing a transgenic plant of a predominantly unsaturated temperate zone oilseed crop plant species to seed, wherein said plant comprises a recombinant DNA construct integrated into the genome of its cells, wherein said recombinant DNA construct comprises a transcriptional initiation region obtained from a plant gene which is expressed preferentially in plant seed, and wherein said construct provides for a nucleic acid sequence encoding a bacterial or foreign plant fatty acid saturation modifying enzyme to be expressed in said plant seed; harvesting mature plant seed; and separating a seed oil from meal of said plant seed whereby a plant seed oil having a modified fatty acid saturation as compared to the fatty acid saturation of seed oil from an untransformed parent of said temperate zone oilseed crop plant is obtained, where said fatty acid saturation modifying enzyme is beta-ketoacyl-ACP synthase wherein said predominantly unsaturated temperate oilseed crop plant is selected from the group consisting of corn, soybean, rapeseed, canola, safflower, sunflower, peanut, and cotton.

9. The method of claim 8 wherein said recombinant DNA construct comprises a transcriptional initiation region obtained from a plant gene which is expressed preferentially in developing plant seed tissue.

10. The method of claim 8 wherein said construct further comprises a selectable marker.

11. The method of claim 8 wherein said construct further comprises a T-DNA border.

12. The method of claim 8 wherein said plant is a dicotyledenous plant.

13. The method of claim 8 wherein said plant is a *Brassica* plant.

14. The method of claim 13 wherein said *Brassica* plant is a *Brassica napus* or *Brassica campestris* plant.

15. A plant seed of a predominantly unsaturated temperate zone oilseed crop plant species, wherein cells of said plant seed contain a recombinant DNA construct integrated into the cell genome, wherein said recombinant DNA construct comprises a transcriptional initiation region obtained from a plant gene which is expressed preferentially in plant seed tissue and a nucleic acid sequence encoding a bacterial or foreign plant fatty acid saturation modifying enzyme wherein said nucleic acid sequence is expressed in said plant seed cells, and wherein said plant seed comprises oil having a modified fatty acid saturation as compared to nontransformed seed of said predominantly unsaturated temperate zone oilseed crop plant species, where said fatty acid saturation modifying enzyme is beta-ketoacyl-ACP synthase, wherein said predominantly unsaturated temperate oilseed crop plant is selected from the group consisting of corn, soybean, rapeseed, canola, safflower, sunflower, peanut, and cotton.

16. The plant seed of claim 15 wherein said recombinant DNA construct comprises a transcriptional initiation region obtained from a plant gene which is expressed preferentially in developing plant seed tissue.

17. The plant seed of claim 15 wherein said recombinant DNA construct further comprises a selectable marker.

18. The plant seed of claim 15 wherein said recombinant DNA construct further comprises a T-DNA border.

19. The plant seed of claim 15 wherein said temperate zone oilseed crop plant is a dicotyledenous plant.

20. The plant seed of claim 15 wherein said temperate zone oilseed crop plant is a *Brassica* plant.

21. The plant seed of claim 20 wherein said *Brassica* plant is a *Brassica napus* or *Brassica campestris* plant.

22. The method according to any one of claims 1, 8, or 15, wherein said transcription initiation region obtained from a plant gene which is expressed preferentially in plant seed tissue is a seed specific promoter.

23. The method according to claim 22, wherein said seed specific promoter is selected from the group consisting of Bce 4, Bcg 4-4, seed ACP and napin 1-2.

24. The method according to claim 22, wherein said seed specific promoter is a napin promoter.

25. The method according to any one of claims 1, 8, or 15, wherein said nucleic acid sequence encoding a plant fatty acid saturation modifying enzyme is SEQ ID NO: 17.

26. The method of claim 1 wherein said plant is a soybean plant.

27. The method of claim 8 wherein said plant is a soybean plant.

28. The plant seed of claim 15 wherein said temperate zone oilseed crop plant is a soybean plant.

* * * * *